United States Patent
Liu et al.

(10) Patent No.: US 10,174,015 B2
(45) Date of Patent: Jan. 8, 2019

(54) SUBSTITUTED HETEROCYCLIC DERIVATIVE, PREPARATION METHOD AND USE THEREOF

(71) Applicant: Xiamen University, Xiamen, Fujian Province (CN)

(72) Inventors: Zuguo Liu, Xiamen (CN); Yan Qiu, Xiamen (CN); Jie Ren, Xiamen (CN); Yuhang Li, Xiamen (CN); Longhe Yang, Xiamen (CN); Chenggang Zhu, Xiamen (CN)

(73) Assignee: Xiamen University, Xiamen, Fujian Province (CN)

( * ) Notice: Subject to any disclaimer, the term of this patent is extended or adjusted under 35 U.S.C. 154(b) by 0 days.

(21) Appl. No.: 15/522,985

(22) PCT Filed: Oct. 29, 2015

(86) PCT No.: PCT/CN2015/093140
§ 371 (c)(1),
(2) Date: Apr. 28, 2017

(87) PCT Pub. No.: WO2016/066115
PCT Pub. Date: May 6, 2016

(65) Prior Publication Data
US 2017/0334896 A1    Nov. 23, 2017

(30) Foreign Application Priority Data

Oct. 31, 2014 (CN) .......................... 2014 1 0603721
Oct. 31, 2014 (CN) .......................... 2014 1 0604001

(51) Int. Cl.
| | | |
|---|---|---|
| C07D 263/26 | (2006.01) | |
| C07D 413/06 | (2006.01) | |
| C07D 413/14 | (2006.01) | |
| C07D 207/273 | (2006.01) | |
| C07D 207/28 | (2006.01) | |

(52) U.S. Cl.
CPC ....... *C07D 413/14* (2013.01); *C07D 207/273* (2013.01); *C07D 207/28* (2013.01); *C07D 263/26* (2013.01); *C07D 413/06* (2013.01)

(58) Field of Classification Search
CPC .............................. C07D 263/26; C07D 413/06
See application file for complete search history.

(56) References Cited

U.S. PATENT DOCUMENTS

| | | | |
|---|---|---|---|
| 2012/0245151 A1 | 9/2012 | Gavai et al. | |
| 2013/0102593 A1* | 4/2013 | Bilcer .................... | A61K 31/16 514/222.2 |
| 2014/0045869 A1 | 2/2014 | Charifson et al. | |
| 2015/0005352 A1* | 1/2015 | Cohen .................. | C07D 277/14 514/369 |

FOREIGN PATENT DOCUMENTS

| | | |
|---|---|---|
| CN | 103242262 A | 8/2013 |
| CN | 104352488 A | 2/2015 |
| CN | 104356082 A | 2/2015 |
| ES | 2405435 | 5/2013 |

OTHER PUBLICATIONS

PubChem CID 9837663—National Center for Biotechnology Information. PubChem Compound Database; CID=9837663, https://pubchem.ncbi.nlm.nih.gov/compound/9837663 (accessed Jan. 19, 2018), create date Oct. 25, 2006.*
Chemical Abstracts Registry No. 1659303-87-3, indexed in the Registry file on STN CAS Online Mar. 10, 2015.*
Wang et al., Organic Letters, 2006, 8(17), pp. 3821-3824 and the Supporting Information on pp. S1-S32.*
Yang et al., Scientific Reports, published online Aug. 27, 2015, 5:13565, pp. 1-10.*
PubChem CID 71098231 {National Center for Biotechnology Information. PubChem Compound Database; CID=71098231, https://pubchem.ncbi.nlm.nih.gov/compound/71098231 (accessed Mar. 23, 2018), create date Mar. 21, 2013.*
PubChem CID 71472806—National Center for Biotechnology Information. PubChem Compound Database; CID=71472806, https://pubchem.ncbi.nlm.nih.gov/compound/71472806 (accessed Jul. 19, 2018), create date Jun. 10, 2013. (Year: 2013).*
PubChem 13736386—National Center for Biotechnology Information. PubChem Compound Database; CID=13736386, https://pubchem.ncbi.nlm.nih.gov/compound/13736386 (accessed Jul. 19, 2018), create date Feb. 8, 2007. (Year: 2007).*
Falck et al., Bioorganic & Medicinal Chemistry Letters, 18, 2008, pp. 1768-1771. (Year: 2008).*
Orita et al., Synlett, (2001), No. 5, pp. 637-639. (Year: 2001).*
Translation of PCT Search Report, for PCT/CN2015/093140 dated Jan. 26, 2016 (5 pages).
Ho, Guo-Jie and Mathre, David J., "Lithium-Initiated Imide Formation. A Simple Method for N-Acylation of 2-Oxazolidinones and Bornane-2,10-Sultam", J. Org. Chem., 60(7):2271-2273, 1995.

* cited by examiner

*Primary Examiner* — Laura L Stockton
(74) *Attorney, Agent, or Firm* — Honigman Miler Schwartz and Cohn LLP; Thomas A. Wootton, Esq.; Jonathan P. O'Brien

(57) ABSTRACT

The present invention relates to a class of substituted heterocyclic derivative and preparation method thereof. The chemical structure of the substituted heterocyclic derivate is as follows,

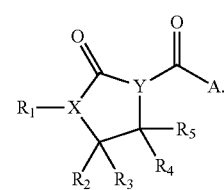

I

8 Claims, 4 Drawing Sheets

SUBSTITUTED HETEROCYCLIC DERIVATIVE, PREPARATION METHOD AND USE THEREOF

CROSS-REFERENCE TO RELATED APPLICATIONS

This application claims priority under 35 U.S.C. § 371 to Patent Cooperation Treaty application PCT/CN2015/093140, filed Oct. 29, 2015, which claims the benefit of Chinese Patent Application No. 201410603721.1, filed Oct. 31, 2014, and Chinese Patent Application No. 201410604001.7, filed Oct. 31, 2014.

TECHNICAL FIELD

The present invention belongs to medical and chemical engineering field, and relate to substituted heterocyclic derivatives, particularly a class of substituted heterocyclic derivatives capable of inhibiting the activity of endocannabinoid hydrolase NAAA and/or FAAH. The present invention further relates to a method for preparing this class of compounds, a pharmaceutical composition comprising this class of compounds, and a medical use of this class of compounds.

BACKGROUND ART

The receptor for tetrahydrocannabinol (THC) is cannabinoid receptor 1 or 2 (cannabinoid receptor 1/2, called $CB_1$ or $CB_2$ for short). The discovery promotes scientists to study endogenic ligands of cannabinoid receptor. It has been found now that N-arachidonoylethanolamine (anandamide, AEA), O-arachidonoylethanolamine (virodhamine), N-arachidonoyldopamine and the like are endocannabinoids acting on cannabinoid receptor. Like lipid transmitters such as prostaglandin, these endocannabinoids are synthesized in situ according to actual need rather than accumulated in vivo, are modulated by enzymes and receptors, and can be metabolized by the specific hydrolases into the corresponding substances such as fatty acid, ethanolamine and glycerol, thereby reducing their effects in vivo.

AEA is the first found endocannabinoid (Devane W A, Hanus L, Breuer A, et al., Science, 1992, 258:1946-1949; Di Marzo V, De Petrocellis L., Curr Med Chem, 2010, 17:1430-1449; Gasperi V, Dainese E, Oddi S, et al., Curr Med Chem, 2013, 20:64-78.), mainly activates $CB_1$ receptor, and can have pharmacological functions similar to those of Cannador such as THC. AEA is widely distributed in vivo, and is detectable in central nervous system, and organs such as liver, lung and gastrointestinal tract. AEA can have pharmacological actions such as anti-inflammatory effect and analgesic effect by direct activation of endocannabinoid receptor (CB). In addition, it has been reported that AEA also has relatively weak agonistic effects on transient receptor potential cation channel subfamily V member 1 (TRPVI) (Bouaboula M, Hilairet S, Marchand J, et al., Eur J Pharmacol, 2005, 517:174-181; Mechoulam R, Ben-Shabat S, Hanus L, et al., Biochem Pharmacol, 1995, 50:83-90; Sugiura T, Kondo S, Sukagawa A, et al., Biochem Biophys Res Commun, 1995, 215:89-97.), G protein coupled receptor 55 (GPR55) (Sugiura T, Waku K., Journal of Biochemistry, 2002, 132:7-12; Sigel E, Baur R, Racz I, et al., Proc Natl Acad Sci USA, 2011, 108:18150-18155; Guindon J, Hohmann A G., Cns & Neurological Disorders-Drug Targets, 2009, 8:403-421; Nomura D K, Long J Z, Niessen S, et al., Cell, 2010, 140:49-61; Fowler C J, Gustafsson S B, Chung S C, et al., Current Topics in Medicinal Chemistry, 2010, 10:814-827.), and peroxisome proliferator-activated receptor γ (PPAR-γ) (Arevalo-Martin A, Garcia-Ovejero D, Molina-Holgado E., Neurobiology of Disease, 2010, 38:304-312; Scotter E L, Abood M E, Glass M., British Journal of Pharmacology, 2010, 160:480-498; Cobellis G, Ricci G, Cacciola G, et al., Biology of Reproduction, 2010, 82:451-458; Guida M, Ligresti A, De Filippis D, et al., Endocrinology, 2010, 151:921-928.). AEA is one of the endocannabinoids widely studied now, and AEA is regarded as partial agonist of cannabinoid receptor.

Besides, some fatty acyl ethanolamine lipids, such as N-Oleoylethanolamide (OEA) and N-palmitoylethanolamide (PEA), which do not act on cannabinoid receptor directly, but have similar structures and similar functions in terms of endocrine regulation as AEA and 2-AG (2-arachidonoylglycerol), are called endocannabinoid-like substances. PEA and OEA act on peroxisome proliferator-activated receptor α (PPAR-α) to generate analgesic and anti-inflammatory effects and appetite-suppressing effects (Fu J, Gaetani S, Oveisi F, et al., Nature, 2003, 425:90-93.). Particularly, PEA is widely distributed in vivo, and PEA can act on multiple targets such as central and sensory nervous system, and immunocyte to show analgesic and anti-inflammatory effect. PEA can activate nuclear receptor peroxisome proliferator-activated receptor-α (PPAR-α), or partially activate GPG55 receptor and GPR119 receptor to generate multiple pharmacological actions such as anti-inflammatory effect and analgesic effect (Mol Pharmacol, 2005, 67, 15-19). N-stearoylethanolamine (SEA) can promote apoptosis of tumor cells (Maccarrone M, Pauselli R, Di Rienzo M, et al., Biochem J, 2002, 366:137-144) and suppress appetite (Terrazzino S, Berto F, Dalle Carbonare M, et al., FASEB J, 2004, 18:1580-1582); Oleamide (OA) has the effects such as sleep regulation (Huitron-Resendiz S, Gombart L, Cravatt B F, et al., Exp Neurol, 2001, 172:235-243).

AEA can be hydrolyzed to arachidonic acid and ethanolamine by specific fatty acid amide hydrolase (FAAH), and therefore lose activity. FAAH, obtained by clone in 1996, belongs to amidase signature family, is the first protein of this family found in mammal and presents in intracellular membrane, and has a segment of transmembrane alpha helix. FAAH protein consists of 579 amino acids, and the crystal structure of FAAH has been obtained now. The active center of hydrolysis substrate AEA consists of typical Ser-Ser-Lys (Ser241-Ser217-Lys142). The optimal hydrolytic condition for FAAH is a slightly alkaline pH (pH=8~9), and FAAH is highly selective for hydrolysis of AEA among fatty acid acyl ethanolamine substrate compounds. In addition, FAAH can also hydrolyze other fatty acid amides such as OEA, PEA, and OA (McKinney M K, Cravatt B F., Annu Rev Biochem, 2005, 74:411-432; Fezza F, De Simone C, Amadio D, et al., Subcell Biochem, 2008, 49:101-132), but with a relatively weak hydrolytic activity.

In FAAH gene-knockout mice, AEA level was significantly increased in central and peripheral tissues (Cravatt B F, Demarest K, Patricelli M P, et al., Proc Natl Acad Sci USA, 2001, 98:9371-9376). AEA level can also be significantly increased by inhibition of FAAH activity with small molecular compounds, however, animal exhibits cannabis-like side effects such as rigidity, reduced activity, and reduced body temperature. Now, FAAH inhibitors have certain effects against depression, anxiety, neuropathic pain and the like. Some FAAH inhibitors have been studied in clinic for the treatment of depression, arthritis pain and the like. FAAH inhibitors can be divided into the following four classes depending on their structures: early AEA substrate analogs, α-ketone heterocyclic compounds, carbamates and aromatic ureas.

The specific hydrolase for PEA, N-acylethanolamine acid amidase (NAAA), had not been found and cloned until 2005 (Tsuboi K, Sun Y X, Okamoto Y, et al., J Biol Chem, 2005, 280:11082-11092). Natuo Ueda research group found a cannabinoid hydrolase with the activity of hydrolyzing AEA in a human megakaryoblastic cell line (CMK) in 1999 (Ueda N, Yamanaka K, Terasawa Y, et al., FEBS Lett, 1999, 454:267-270). However, the enzyme is quite different from the known AEA hydrolase FAAH in the following aspects: (1) the enzyme has a high hydrolytic activity at acidic pH (pH 4.5), while FAAH enzyme has a high hydrolytic activity at basic condition (pH 9.0) (Linsenbardt D N, Boehm S L, 2nd., Neuroscience, 2009, 164:424-434); (2) the enzyme is much more active for the hydrolysis of PEA than for hydrolysis of AEA; and (3) the enzyme is not sensitive to serine inhibitors PMSF and MAFP that have good inhibitory effect on FAAH. Soon after, the research group found that NAAA enzyme was most active in lung among various tissues, was less active gradually in tissues such as spleen, thymus gland and small intestine, and was finally purified in lung tissues (Ueda N, Yamanaka K, Yamamoto S., J Biol Chem, 2001, 276:35552-35557). In 2005, the cDNA sequence of the enzyme was cloned from rat, mouse and human-derived cells, and the enzyme was denominated as N-Acylethanolamine-hydrolyzing Acid Amidase (NAAA) (Tsuboi K, Sun Y X, Okamoto Y, et al., J Biol Chem, 2005, 280:11082-11092). It was found in a subsequent research that NAAA was mainly expressed in lysosomes (Tsuboi K, Zhao L Y, Okamoto Y, et al., Biochim Biophys Acta, 2007, 1771:623-632). NAAA comprises 362 amino acid residues in rat and mouse with a molecular weight of 40.3 Kda (rat) and 40.1 kDa (mouse) respectively, and it also comprises 359 amino acid residues in human) with a molecular weight of 40.1 kDa. Among these amino acid sequences, rat NAAA is 90.1% identical to mouse NAAA, rat NAAA is 76.5% identical to human NAAA, and mouse NAAA is 76.7% identical to human NAAA. Human NAAA gene is on 4q21.1 chromosome. NAAA, which has no homology with FAAH but has a certain homology with acid ceramidases, is classified into choloylglycine hydrolase family, and is selective for hydrolysis of amide (Tsuboi K, Sun Y X, Okamoto Y, et al., J Biol Chem, 2005, 280:11082-11092).

Due to lack of crystal structure, the steric configuration for hydrolysis-catalyzing domain of NAAA is not clear yet, and there are few specific inhibitors. Limited researches show that topical administration of β-lactam type NAAA inhibitor S-OOPP ($IC_{50}$=420 nM) can inhibit the carrageenan-induced reduction in granulomatous leukocyte PEA content in rat as well as the LPS-induced reduction in cellular PEA content in RAW264.7, thereby inhibiting leukocyte migration and inflammatory exudation, and can also have good therapeutic effects in spinal injury model, the process was mediated by PPAR-α pathway (Solorzano C, Zhu C, Battista N, et al., Proc Natl Acad Sci USA, 2009, 106:20966-20971). Topical administration of a structural analog ARN077 ($IC_{50}$=127 nM) can significantly inhibit inflammatory pain induced by carrageenan and neuropathic pain caused by sciatic nerve ligation. In sciatic nerve ligation models, ARN077 (1%, 20 μL, epidermal administration) has better analgesic effects on allodynia than the positive control agent gabapentin (50 mg/kg, oral administration) (Sasso O, Moreno-Sanz G, Martucci C, et al., Pain, 2013, 154:350-360). This research demonstrated for the first time that NAAA inhibitors have analgesic effects, the main pharmacophore 4-membered lactone ring for this class of structures is unstable structurally and has poor biological stability, with a half-life of less than 1 min in animal, and thus cannot be applied by systemic administration.

Compared to the analgesics such as opioids, anti-epileptics, anti-depressive agents and local anaesthetics, endocannabinoid hydrolase inhibitors have less side effects on central nervous system, and have no addiction; compared to COX inhibitors as anti-inflammatory analgesics, such as ibuprofen, celecoxib and aspirin, endocannabinoid hydrolase inhibitors have better drug safety as they would not result in intestine and stomach bleeding and serious cardiovascular event (Biochem J, 2004, 380, 749-756; Journal of Medicinal Chemistry, 2008, 51, 7327-7343; PAIN, 2013, 154, 326-327).

The object of the invention is to provide a novel, more stable endocannabinoid hydrolase inhibitor, and a preparation method and a use thereof.

Contents of Invention

After paying creative work and carrying out a large number of tests, the inventors obtain a class of novel compounds, which can be used as endocannabinoid hydrolase inhibitors, and can be used in the treatment of pains, including, but not limited to neuropathic pain, inflammatory pain, and mixed pain. The inventors have also found surprisingly that this class of compounds have excellent stability and have a half-life of between 60 and 300 min in rats, i.e., have higher stability than the reported β-lactam type NAAA inhibitors. Therefore, the inventions are provided as follows.

In a first aspect, the invention relates to a compound of Formula I, or a pharmaceutically acceptable salt, a hydrate or a solvate thereof,

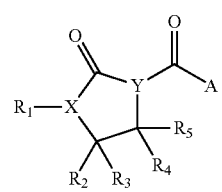

I wherein

X is selected from the group consisting of C, N and O;

Y is selected from the group consisting of C and N;

A is selected from the group consisting of $R_{12}$, $OR_6$, $NR_7R_8$ and $CR_9R_{10}R_{11}$; $R_1$, $R_2$, $R_3$, $R_4$, $R_5$, $R_6$, $R_7$, $R_8$, $R_9$, $R_{10}$, $R_{11}$ are independently selected from the group consisting of —H, =O, =NOR', halogen, halogenated group, polyhalogenated group, —(CH$_2$)$_n$CN, —(CH$_2$)$_n$NO$_2$, —(CH$_2$)$_n$R', —(CH$_2$)$_n$COOR', —(CH$_2$)$_n$CONR'$_2$, —(CH$_2$)$_n$OR', —(CH$_2$)$_n$SR', —(CH$_2$)$_n$SOR', —(CH$_2$)$_n$SO$_2$R', —(CH$_2$)$_n$NR'$_2$, —(CH$_2$)$_n$NR'COR' and —(CH$_2$)$_n$NR'SO$_2$R';

$R_{12}$ is —(CH$_2$)$_n$R$_{13}$;

$R_{13}$ is selected from the group consisting of H, a linear or branched $C_{1-10}$ alkyl, phenyl, thienyl, furyl, $C_{4-6}$cycloalkyl, biphenylyl, phenoxyphenyl, benzyloxyphenyl, phenylethoxyphenyl, piperidyl, N-benzylpiperidyl, naphthyl, indolyl and uracil group, $R_{13}$ is optionally substituted by one or two substituents selected from the group consisting of halogen, methyl, hydroxyl, $C_{1-6}$alkyl, $C_{1-6}$alkoxy, hydroxyl, nitro, trifluoromethyl, cyano, $C_{1-6}$alkyl monosubstituted or polysubstituted by halogen, and $C_{1-6}$alkoxyl monosubstituted or polysubstituted by halogen.

n is an integer selected from 0-10;

each R' is independently H or is a group with no more than 20 carbon atoms and selected from substituted or unsubstituted linear alkyl, branched alkyl, cycloalkyl, cycloheteroalkyl, alkenyl, alkynyl, linear heteroalkyl, branched heteroalkyl, heterocycloalkyl, heteroalkenyl, heteroalkynyl, heterocyclyl or aryl, which contains no more than 20 C atoms.

In an embodiment, the compound, or a pharmaceutically acceptable salt, a hydrate or a solvate thereof according to the first aspect of the invention, may be represented by Formula Ia,

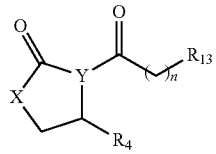

Ia wherein:

X is O or N;

Y is N;

n is an integer selected from 0~7;

$R_4$ is H, methyl, halogen, $C_{1-6}$alkyl, $C_{1-6}$alkoxy, hydroxyl, nitro, trifluoromethyl, cyano, $CH_3C(=O)CH_2-$ or $(CH_3)_2NCH_2-$;

$R_{13}$ is selected from the group consisting of H, a linear or branched $C_{1-10}$alkyl, phenyl, thienyl, furyl, $C_{4-6}$cycloalkyl, biphenylyl, phenoxyphenyl, benzyloxyphenyl, phenylethoxylphenyl, piperidyl, N-benzylpiperidyl, naphthyl, indolyl and uracil group, $R_{13}$ is optionally substituted by one or two substituents selected from the group consisting of halogen, methyl, hydroxyl, $C_{1-6}$alkyl, $C_{1-6}$alkoxy, hydroxyl, nitro, trifluoromethyl, cyano, $C_{1-6}$alkyl monosubstituted or polysubstituted by halogen, or $C_{1-6}$alkoxyl monosubstituted or polysubstituted by halogen.

In a second aspect, the invention relates to a method for preparing a compound of Formula Ia, or a pharmaceutically acceptable salt, a hydrate or a solvate thereof, comprising:

in a suitable solution, reacting a compound of Formula II with a compound of Formula III at a suitable temperature to obtain a compound of Formula Ia,

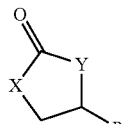

II

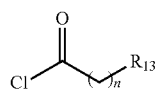

III wherein X, Y, $R_4$, $R_{13}$ and n are defined as described above. In an embodiment, the suitable solution is a solution containing n-butyl lithium, and the suitable temperature is −78° C.~0° C.

In a third aspect, the invention relates to a pharmaceutical composition, comprising at least the compound of Formula I or Ia, or a pharmaceutically acceptable salt, a hydrate or a solvate thereof according to the first aspect of the invention, and a pharmaceutically acceptable adjuvant.

In a fourth aspect, the invention relates to a method for treating a disease or disorder, or alleviating severity of said disease or disorder, comprising administering to a patient in need of the treatment a therapeutically effective amount of at least one compound of Formula I or Ia, or a pharmaceutically acceptable salt, a hydrate or a solvate thereof according to the first aspect of the invention, wherein said disease or disorder is pain.

In a fifth aspect, the invention relates to a use of the compound of Formula I or Ia, or a pharmaceutically acceptable salt, a hydrate or a solvate thereof according to the first aspect of the invention in manufacture of a medicament for treating a disease or disorder, or alleviating severity of said disease or disorder, wherein said disease or disorder is pain.

In a sixth aspect, the invention relates to the compound of Formula I or Ia, or a pharmaceutically acceptable salt, a hydrate or a solvate thereof, for use in treating a disease or disorder, or alleviating severity of said disease or disorder, wherein said disease or disorder is pain.

In the invention, said pain includes, but is not limited to neuropathic pain (including, but not limited to central neuropathic pain, and peripheral neuropathic pain), inflammatory pain (including, but not only limited to osteoarthritis pain, fibromyalgia syndrome, inflammatory pain of rheumatic and rheumatoid arthritis, inflammatory pain of endometriosis, inflammatory toothache, ankylosing spondylitis pain, gouty arthritis pain, and visceral inflammatory pain), mixed pain (including, but not only limited to lumbodynia, shoulder pain, burning mouth syndrome, complex regional pain syndrome, migraine, cluster headache, tension headache syndrome, and prosopodynia). Said peripheral neuropathic pain includes, but is not limited to post-herpetic neuralgia, pain caused by diabetic perineuropathy, neurothlipsis and exudation caused by tumor, lumbar surgery failure syndrome, neuropathic pain caused by lumbar disc protrusion, postpartum neuralgia, trigeminal neuralgia, chemotherapy-induced multiple neuropathic pain, post-radiotherapy plexopathy, and radicular neuralgia. Said central neuropathic pain includes, but is not limited to compression pain caused by spinal sclerosis, multiple sclerosis related pain, Parkinsonism related pain, dementia related pain, post-stroke pain, and pain following spinal cord injury. Said visceral inflammatory pain includes, but is not only limited to: appendicitis, gastritis, pancreatitis, prostatitis, myocarditis, interstitial cystitis, pain caused by hepatic, gall or kidney stone, irritable bowel syndrome, and chronic pelvic pain syndrome.

Definition of Substituents

The term "alkyl" used herein refers to a saturated linear or branched monovalent alkyl, preferably having 1-12 carbon atoms, more preferably having 1-10, 1-8, 1-6, 1-4 or 1-3 carbon atoms. Typical examples of "alkyl" include, but are not limited to methyl, ethyl, n-propyl, isopropyl, n-butyl, isobutyl, tert-butyl, n-pentyl, tert-amyl, neopentyl, hexyl, heptyl, octyl, etc.

The term "alkenyl" used herein refers to a linear or branched ethylenically unsaturated monovalent alkyl containing at least one carbon-carbon double bond (—C=C—), having 2-12 carbon atoms, preferably 2-10, 2-8, 2-6, 2-4 or 2-3 carbon atoms. Typical examples of"alkenyl" include, but are not limited to vinyl, acryl, allyl, buten-1-yl, buten-2-yl, penten-1-yl, penten-2-yl, 1,3-pentadienyl, hexen-1-yl, hexen-2-yl, 1,3-hexadienyl, heptenyl, octenyl, etc.

The term "alkynyl" used herein refers to a linear or branched acetylenically unsaturated monovalent alkyl containing at least one carbon-carbon triple bond (—C≡C—), having 2-12 carbon atoms, preferably 2-10, 2-8, 2-6, 2-4 or 2-3 carbon atoms. Typical examples of "alkynyl" include, but are not limited to acetenyl, propinyl, propargyl, butynyl, pentynyl, hexynyl, heptynyl, octynyl, etc.

The term "amino" used herein refers to —$NH_2$.
The term "hydroxyl" used herein refers to —OH.
The term "cyano" used herein refers to —CN.
The term "carboxyl" used herein refers to —C(O)OH.
The term "cycloalkyl" used herein refers to a saturated cyclic alkyl having 3-12 carbon atoms and having a single ring, two rings or multiple fused rings (including fused and bridged ring system), preferably having 3-10, 3-8, 5-8, 4-6 or 5-6 carbon atoms, particularly preferably having 4-6 carbon atoms. Typical examples of "cycloalkyl" include, but are not limited to monocyclic structure, such as cyclopropyl, cyclobutyl, cyclopentyl, cyclohexyl, cycloheptyl, cyclooctyl, 1-methylcyclopropyl, 2-methylcyclopentyl, 2-methylcycloheptyl, etc.

The term "heterocycloalkyl" used herein refers to cycloalkyl as defined above, which contains one, two or more heteroatoms independently selected from N, O and S. Typical examples of "heterocycloalkyl" include, but are not limited to tetrahydrofuryl, tetrahydrothienyl, pyrrolidinyl, piperazinyl, thiazinyl, piperidyl, morpholinyl, etc.

The terms "heteroalkyl", "heteroalkenyl", "heteroalkynyl" used herein refer to "alkyl", "alkenyl", "alkynyl" having a certain C atom thereof substituted by a heteroatom N, O or S, wherein these heteroatom-containing groups comprise at least one C atom and one heteroatom.

Any hydrogen of these groups can be substituted by halogen, particularly F-substituted group and Cl-substituted group, and can also be substituted by other groups.

The term "aryl" used herein refers to a monovalent substituent of any monocyclic, bicyclic or fused ring system which has aromatic characteristics in terms of electronic distribution for the whole ring system, or combinations thereof. Typical structures include benzene ring, thiophene, furane, pyrrole, thiazole, pyrazolec, imidazole, pyridine, pyrane, pyrimidine, pyrazine, quinoline, isoquinoline, indole, purine or a group resulted from fusion of said aromatic groups in any form. Any hydrogen of these groups can be substituted by halogen, particularly F-substituted group and Cl-substituted group, and can also be substituted by other groups.

The term "alkoxyl" used herein refer to group —$OR_{14}$, wherein $R_{14}$ is alkyl or cycloalkyl as defined herein. Typical examples of "alkoxyl" include, but are not limited to methoxyl, ethoxyl, n-propoxyl, isopropoxyl, n-butoxyl, t-butoxyl, sec-butoxyl, n-pentyloxyl, n-hexyloxy, 1,2-dimethyl butoxyl, cyclohexyloxy, cyclopropyloxy, etc.

The term "halogen" used herein refers to F, Cl, Br or I. The preferred halogen is F, Cl or Br.

The groups defined by the terms used herein may be optionally monosubstituted or polysubstituted by —CN, —OH, —$NH_2$, $C_{1-4}$alkyl, $C_{1-4}$alkoxyl or halogen.

If the name of a compound used herein is not consistent with its chemical formula, the chemical formula shall prevail.

In a preferred embodiment, in the Formula Ia of the invention, X may be O, may also be N.

In a preferred embodiment, in the Formula Ia of the invention, X is O.
In a preferred embodiment, in the Formula Ia of the invention, X is N.
In a preferred embodiment, in the Formula Ia of the invention, Y may be N.
In a preferred embodiment, in the Formula Ia of the invention, n is 0 or 1.
In another preferred embodiment, in the Formula Ia of the invention, n may be 0, may also be 1.
In a preferred embodiment, in the Formula Ia of the invention, n is 4, 5, 6 or 7.
In a preferred embodiment, in the Formula Ia of the invention, n is 5, 6 or 7.
In another preferred embodiment, in the Formula Ia of the invention, n may be 5, may also be 6, may also be 7.
In a preferred embodiment, in the Formula Ia of the invention, $R_4$ is H, methyl, halogen, $C_{1-6}$alkyl, $C_{1-6}$alkoxy, hydroxyl, nitro, trifluoromethyl, cyano, $CH_3C(=O)CH_2$— or $(CH_3)_2NCH_2$—.
In another preferred embodiment, in the Formula Ia of the invention, $R_4$ is H, methyl, halogen, $C_{1-4}$alkyl, $C_{1-4}$alkoxy, hydroxyl, nitro, trifluoromethyl, cyano, $CH_3C(=O)CH_2$— or $(CH_3)_2NCH_2$—.
In another preferred embodiment, in the Formula Ia of the invention, $R_4$ is H, methyl, halogen, hydroxyl, nitro, trifluoromethyl, cyano, $CH_3C(=O)CH_2$— or $(CH_3)_2NCH_2$—.
In another preferred embodiment, in the Formula Ia of the invention, $R_4$ is H, methyl, halogen, $CH_3C(=O)CH_2$— or $(CH_3)_2NCH_2$—.
In another preferred embodiment, in the Formula Ia of the invention, $R_4$ is H, methyl, $CH_3C(=O)CH_2$— or $(CH_3)_2NCH_2$—.
In another preferred embodiment, in the Formula Ia of the invention, $R_4$ is H, methyl or $CH_3C(=O)CH_2$.
In another preferred embodiment, in the Formula Ia of the invention, $R_4$ is H or $(CH_3)_2NCH_2$—.
In a preferred embodiment, in the Formula Ia of the invention, $R_{13}$ is selected from the group consisting of H, a linear or branched $C_{1-10}$ alkyl, phenyl, thienyl, furyl, $C_{4-6}$cycloalkyl, biphenylyl, phenoxyphenyl, benzyloxyphenyl, phenylethoxylphenyl, piperidyl, N-benzylpiperidyl, naphthyl, indolyl, and uracil group, $R_{13}$ is optionally substituted by one or two of the following substituents selected from the group consisting of halogen, methyl, hydroxyl, $C_{1-6}$alkyl, $C_{1-6}$alkoxy, hydroxyl, nitro, trifluoromethyl, cyano, $C_{1-6}$alkyl monosubstituted or polysubstituted by halogen, or $C_{1-6}$alkoxyl monosubstituted or polysubstituted by halogen.

In another preferred embodiment, in the Formula Ia of the invention, $R_{13}$ is selected from the group consisting of H, a linear or branched $C_{1-8}$alkyl, phenyl, thienyl, furyl, cyclohexyl, biphenylyl, phenoxyphenyl, benzyloxyphenyl, phenylethoxylphenyl, piperidyl, N-benzylpiperidyl, naphthyl, indolyl, and uracil group, $R_{13}$ is optionally substituted by one or two of the following substituents selected from the group consisting of halogen, methyl, hydroxyl, $C_{1-4}$alkyl, $C_{1-4}$alkoxy, hydroxyl, nitro, trifluoromethyl, cyano, $C_{1-4}$alkyl monosubstituted or polysubstituted by halogen, or $C_{1-4}$alkoxyl monosubstituted or polysubstituted by halogen.

In another preferred embodiment, in the Formula Ia of the invention, $R_{13}$ is selected from the group consisting of H, a linear or branched alkyl containing 8 carbon atoms,

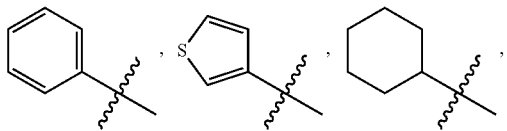

In another preferred embodiment, in the Formula Ia of the invention, $R_{13}$ is selected from the group consisting of H, a linear alkyl containing 8 carbon atoms,

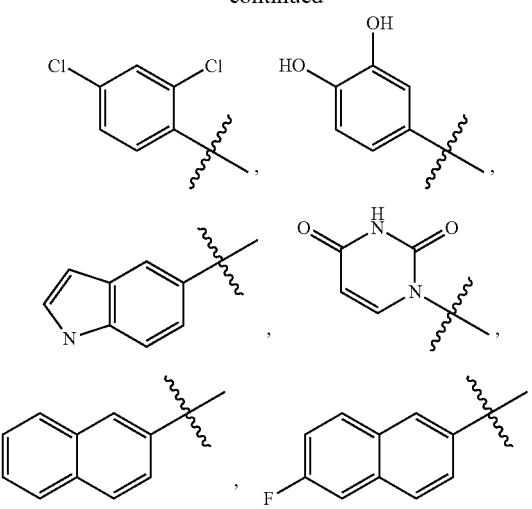

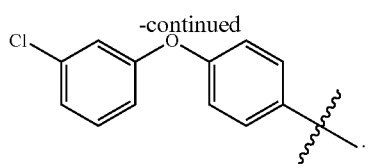

In another preferred embodiment, in the Formula Ia of the invention, R$_{13}$ is selected from the group consisting of H, a linear or branched alkyl containing 8 carbon atoms,

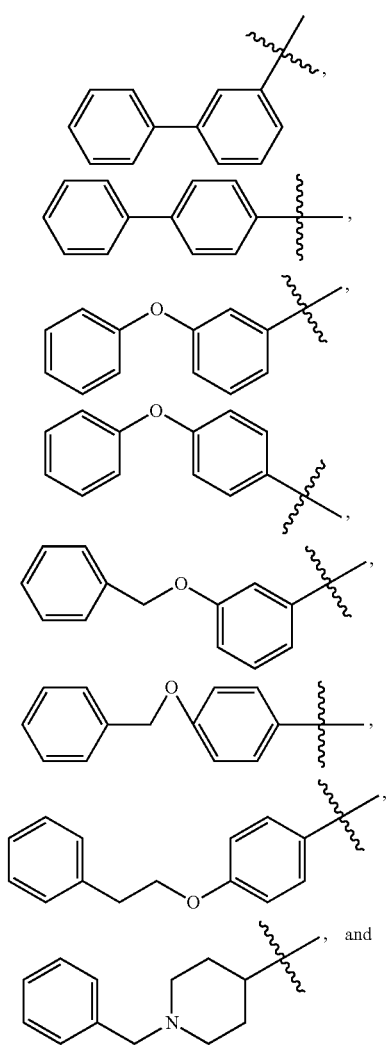

and

In a preferred embodiment, a compound of Formula Ia, or a pharmaceutically acceptable salt, a hydrate or a solvate thereof, wherein:

X is O or N;
Y is N;
n is an integer selected from 0-7;
R$_4$ is H, methyl, halogen, C$_{1-4}$alkyl, C$_{1-4}$alkoxy, hydroxyl, nitro, trifluoromethyl, cyano, CH$_3$C(=O)CH$_2$— or (CH$_3$)$_2$NCH$_2$—;
R$_{13}$ is selected from the group consisting of H, a linear or branched C$_{1-8}$alkyl, phenyl, thienyl, furyl, cyclohexyl, biphenylyl, phenoxyphenyl, benzyloxyphenyl, phenylethoxyphenyl, piperidyl, N-benzylpiperidyl, naphthyl, indolyl, and uracil group, R$_{13}$ is optionally substituted by one or two of the following substituents selected from the group consisting of halogen, methyl, hydroxyl, C$_{1-4}$alkyl, C$_{1-4}$alkoxy, hydroxyl, nitro, trifluoromethyl, cyano, C$_{1-4}$alkyl monosubstituted or polysubstituted by halogen, C$_{1-4}$alkoxyl monosubstituted or polysubstituted by halogen.

In another preferred embodiment, a compound of Formula Ia, or a pharmaceutically acceptable salt, a hydrate or a solvate thereof, wherein:

X is O or N;
Y is N;
n is 0, 1, 2, 3, 4, 5, 6 or 7;
R$_4$ is H, methyl, halogen, C$_{1-4}$alkyl, C$_{1-4}$alkoxy, hydroxyl, nitro, trifluoromethyl, cyano, CH$_3$C(=O)CH$_2$— or (CH$_3$)$_2$NCH$_2$—;
R$_{13}$ is selected from the group consisting of H, a linear or branched alkyl containing 8 carbon atoms,

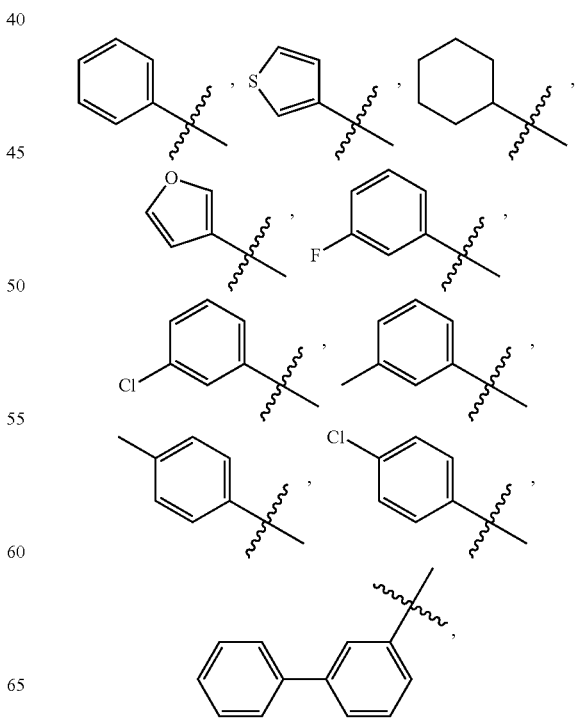

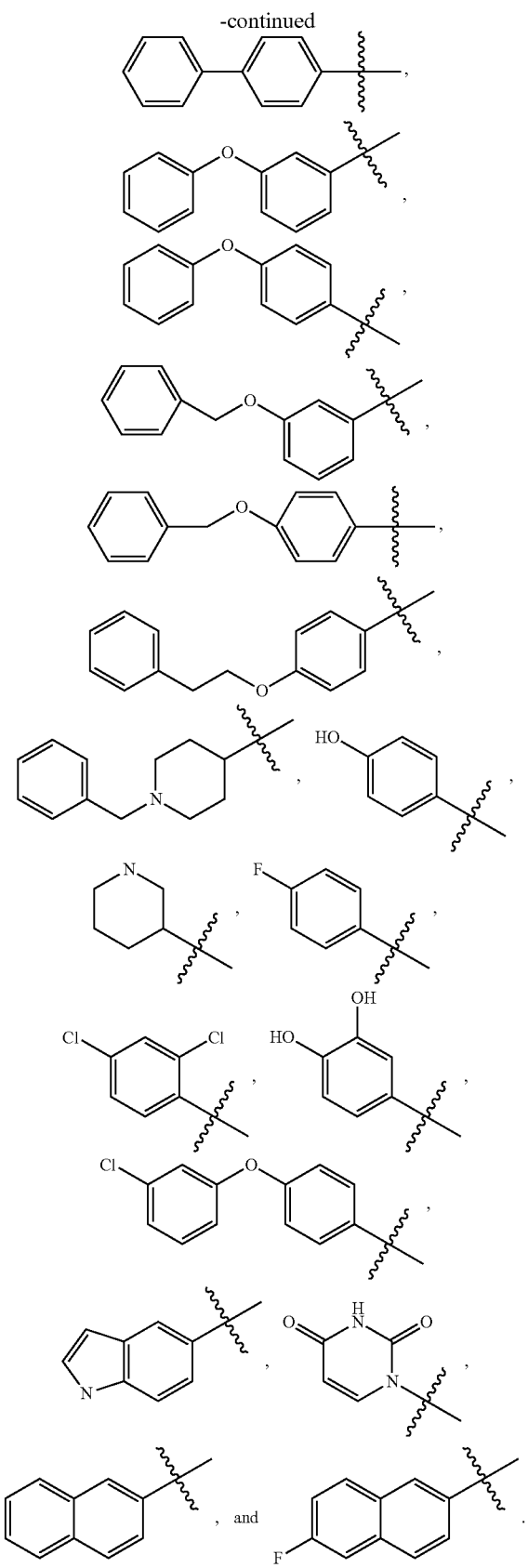

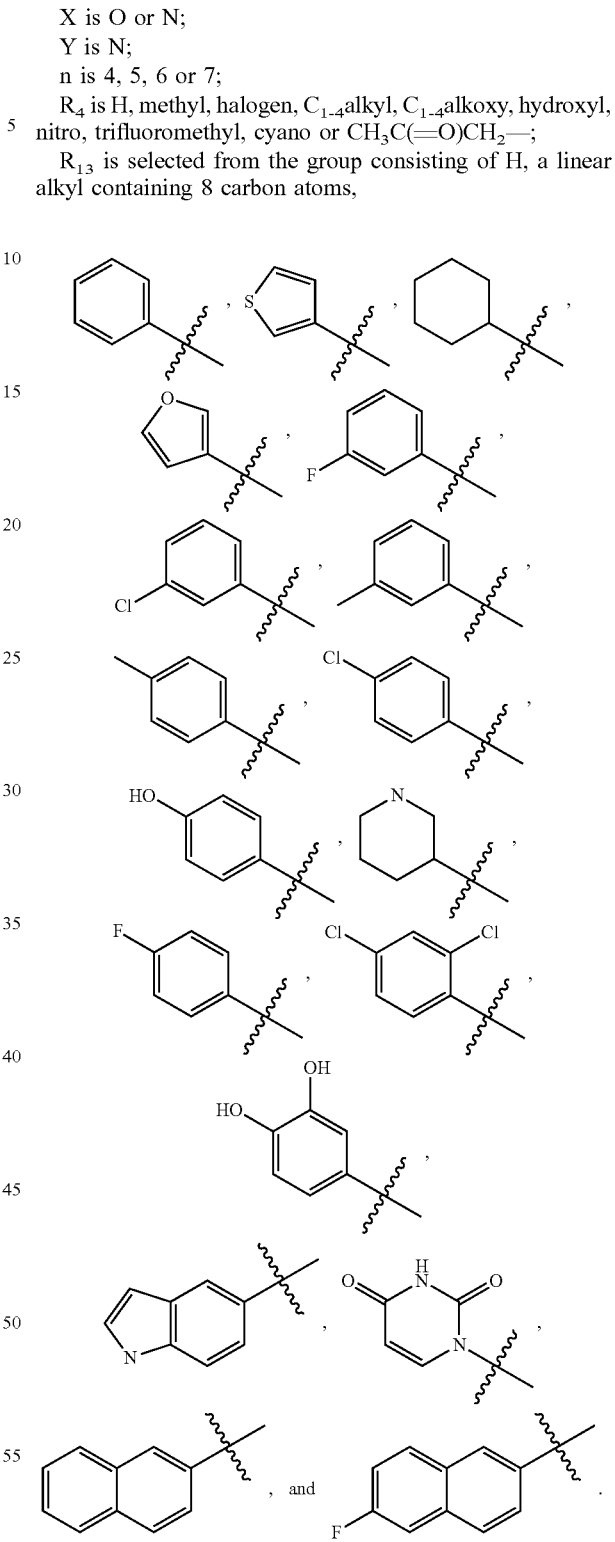

X is O or N;
Y is N;
n is 4, 5, 6 or 7;
$R_4$ is H, methyl, halogen, $C_{1-4}$alkyl, $C_{1-4}$alkoxy, hydroxyl, nitro, trifluoromethyl, cyano or $CH_3C(=O)CH_2-$;
$R_{13}$ is selected from the group consisting of H, a linear alkyl containing 8 carbon atoms, In another preferred embodiment, a compound of Formula Ia, or a pharmaceutically acceptable salt, a hydrate or a solvate thereof, wherein:

In another preferred embodiment, a compound of Formula Ia, or a pharmaceutically acceptable salt, a hydrate or a solvate thereof, wherein:
X is O or N;
Y is N;
n is 4, 5, 6 or 7;
$R_4$ is H, methyl or $CH_3C(=O)CH_2-$;

$R_{13}$ is selected from the group consisting of H, a linear alkyl containing 8 carbon atoms,

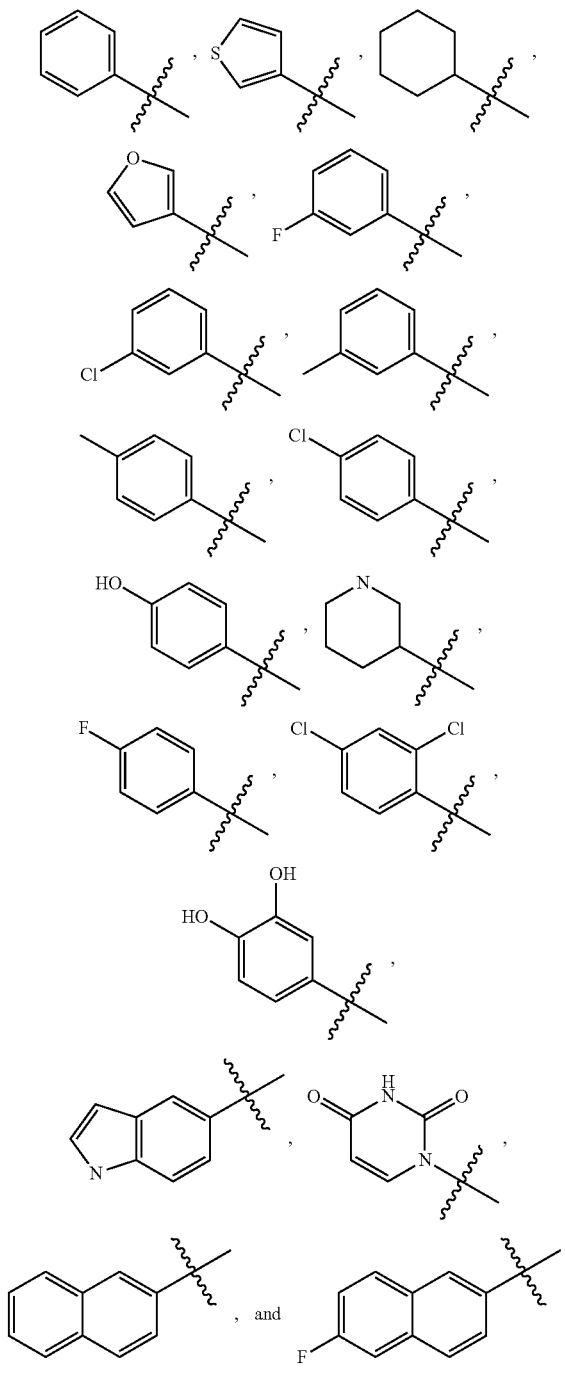

, and .

In another preferred embodiment, a compound of Formula Ia, or a pharmaceutically acceptable salt, a hydrate or a solvate thereof, wherein:

X is O;

Y is N;

n is 4, 5, 6 or 7;

$R_4$ is H, methyl, halogen, $C_{1-4}$alkyl, $C_{1-4}$alkoxy, hydroxyl, nitro, trifluoromethyl, cyano or $CH_3C(=O)CH_2$—;

$R_{13}$ is selected from the group consisting of H, a linear alkyl containing 8 carbon atoms,

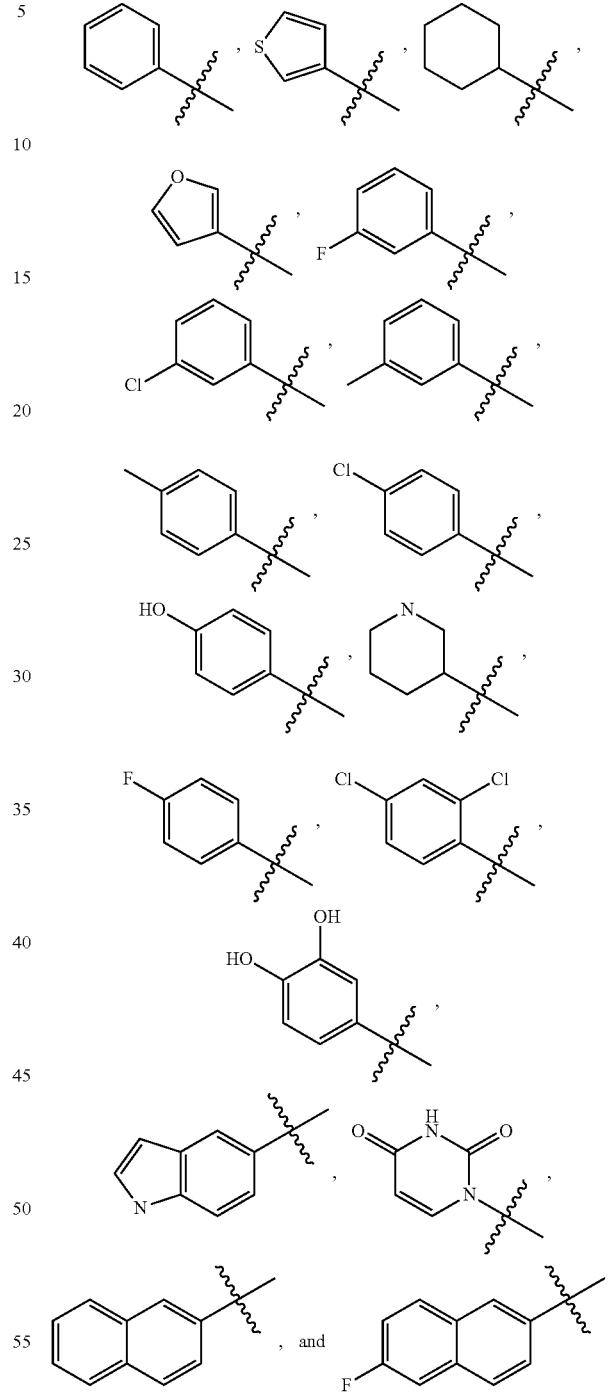

, and .

In another preferred embodiment, a compound of Formula Ia, or a pharmaceutically acceptable salt, a hydrate or a solvate thereof, wherein:

X is O;

Y is N;

n is 4, 5, 6 or 7;

$R_4$ is H, methyl or $CH_3C(=O)CH_2$—;

R13 is selected from the group consisting of H, a linear alkyl containing 8 carbon atoms,

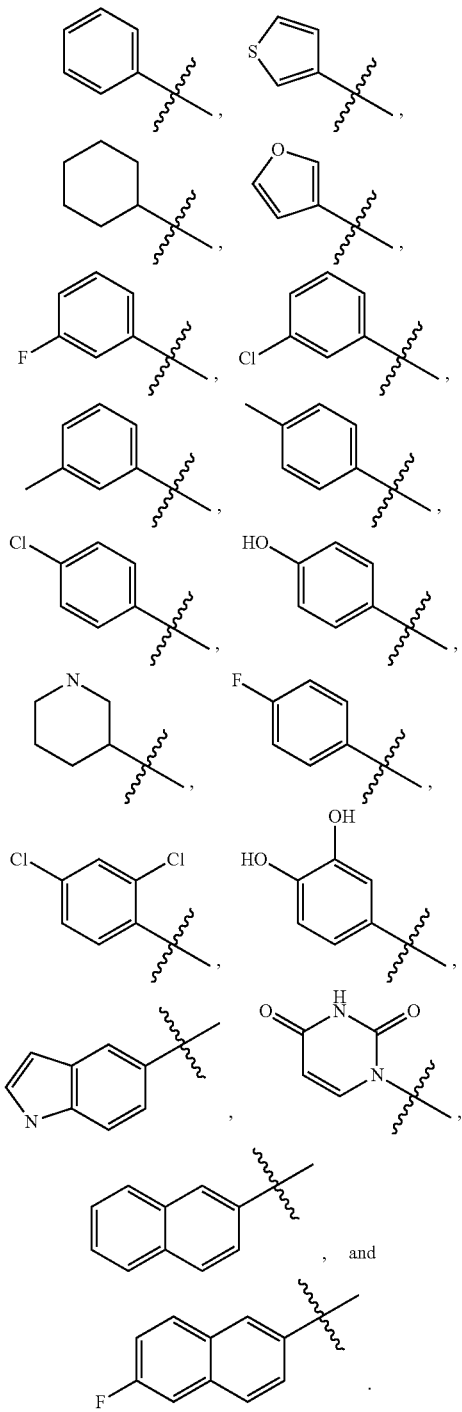

and

In another preferred embodiment, a compound of Formula Ia, or a pharmaceutically acceptable salt, a hydrate or a solvate thereof, wherein:
X is O;
Y is N;
n is 0 or 1;
R4 is H, methyl, halogen, $C_{1-4}$alkyl, $C_{1-4}$alkoxy, hydroxyl, nitro, trifluoromethyl, cyano or $(CH_3)_2NCH_2$—;

R13 is selected from the group consisting of H, a linear or branched alkyl containing 8 carbon atoms,

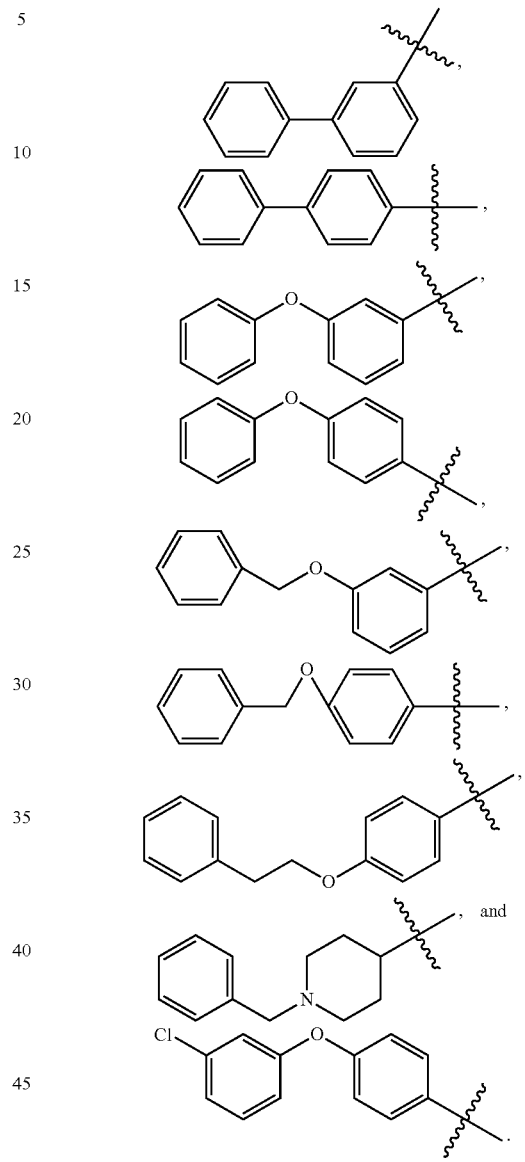

In another preferred embodiment, a compound of Formula Ia, or a pharmaceutically acceptable salt, a hydrate or a solvate thereof, wherein:
X is O;
Y is N;
n is 0 or 1;
R4 is H or $(CH_3)_2NCH_2$—;
R13 is selected from the group consisting of H, a linear or branched alkyl containing 8 carbon atoms,

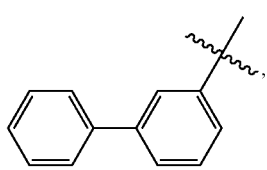

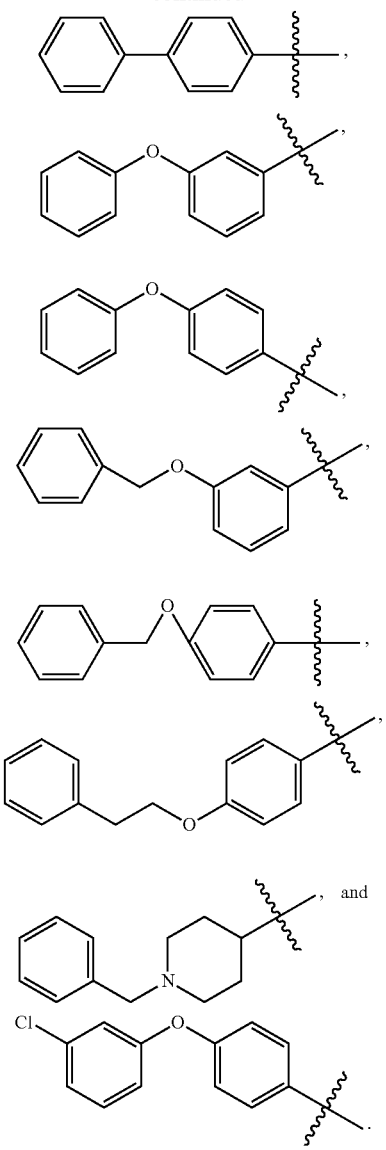
In another preferred embodiment, a compound of Formula I or Formula Ia, or a pharmaceutically acceptable salt, a hydrate or a solvate thereof, is selected from the group consisting of:
Compound 1
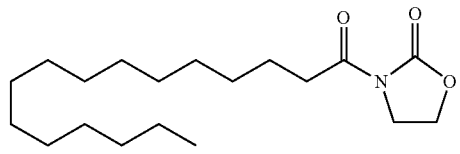
Compound 2
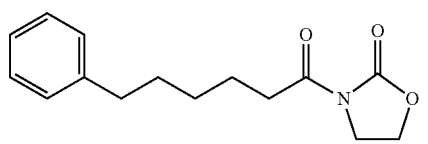
Compound 3
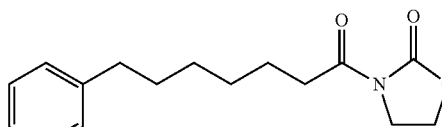
Compound 4
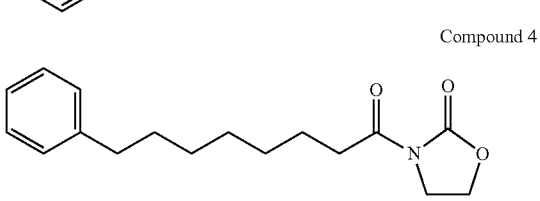
Compound 5
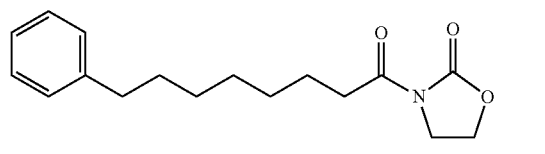
Compound 6
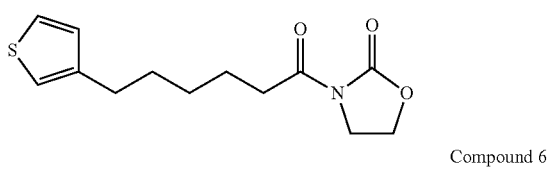
Compound 7
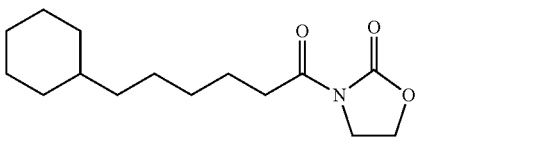
Compound 8
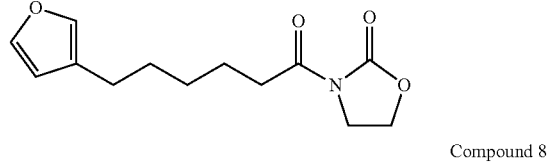
Compound 9
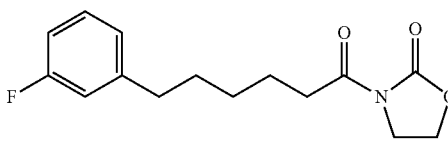
Compound 10
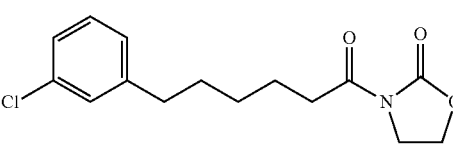
Compound 11
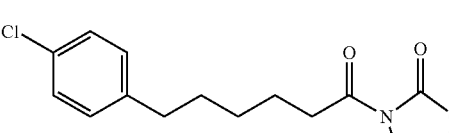
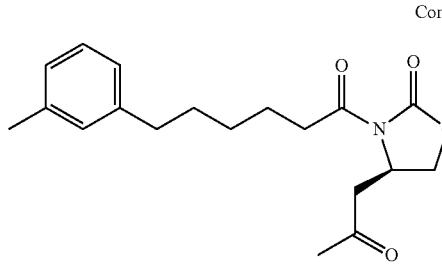

Compound 12
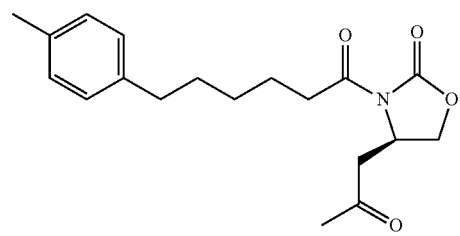
Compound 13
Compound 14
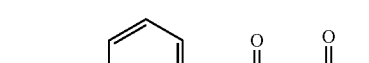
Compound 15
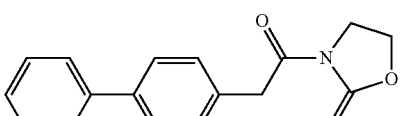
Compound 16
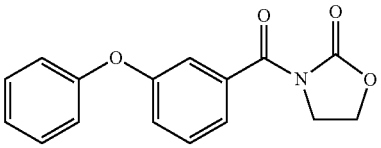
Compound 17
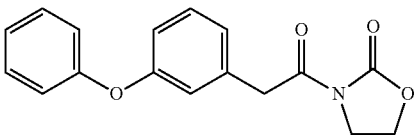
Compound 18
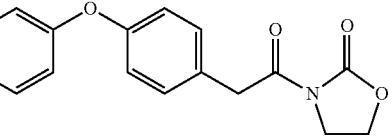
Compound 19
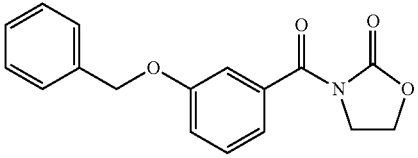
Compound 20
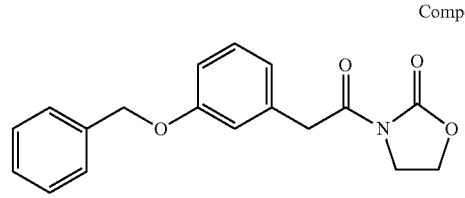
Compound 21
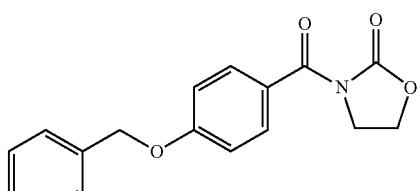
Compound 22
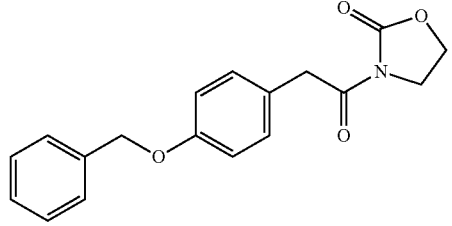
Compound 23
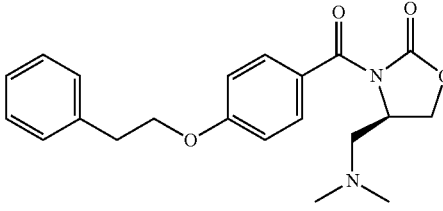
Compound 25
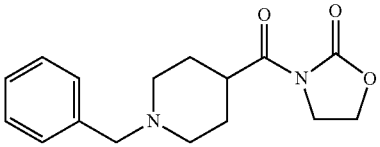
Compound 27
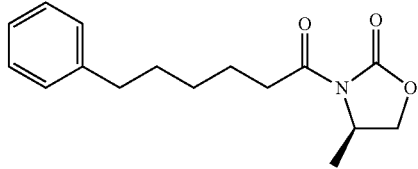
Compound 31
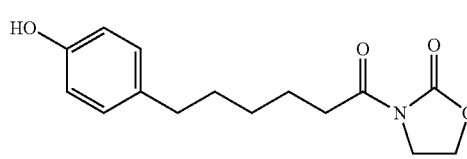
Compound 32
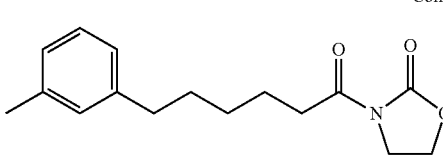
Compound 33
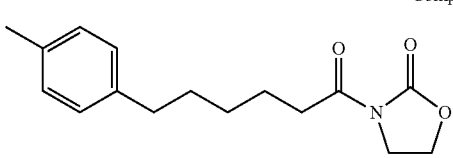

Compound 34
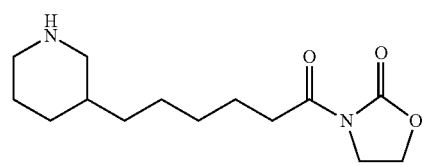

Compound 35
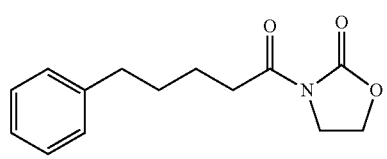

Compound 36
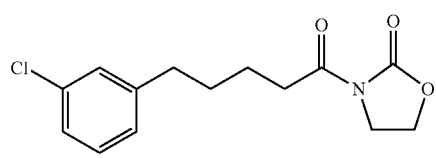

Compound 37
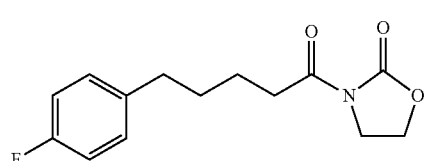

Compound 38
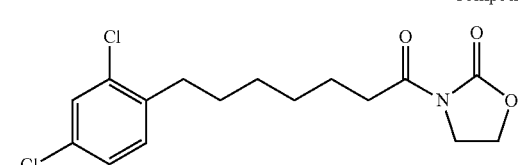

Compound 39
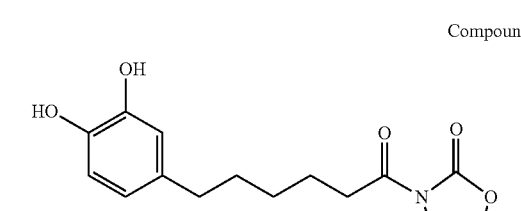

Compound 40
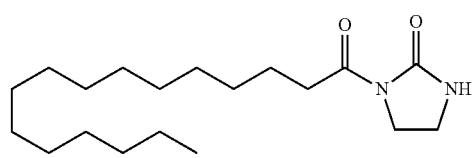

Compound 41
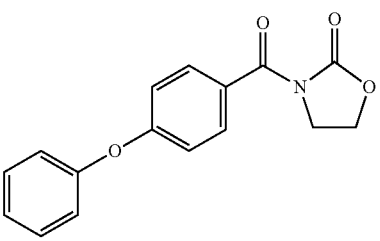

Compound 42
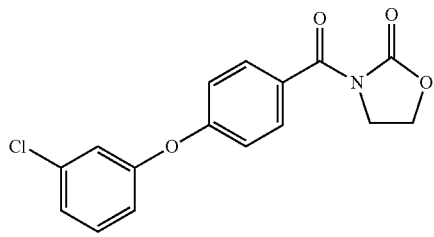

Compound 43
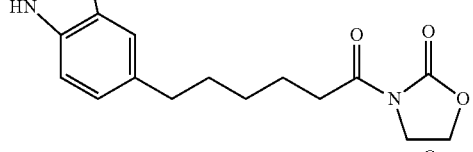

Compound 44
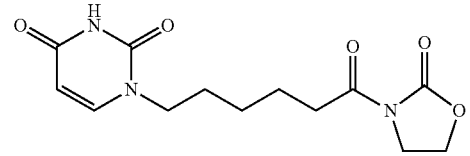

Compound 45
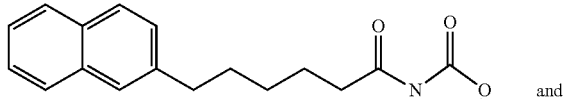

and

Compound 46
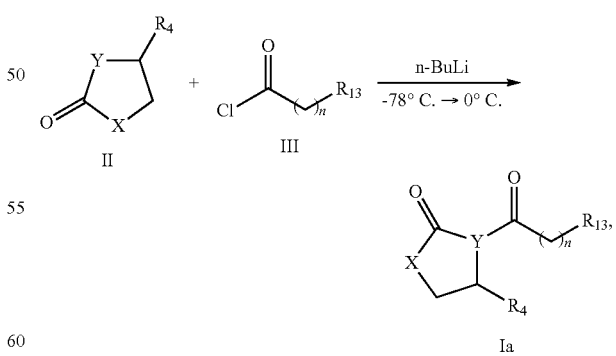

In a preferred embodiment, the compound of Formula Ia according to the invention may be synthesized by the following scheme:

wherein X, Y, $R_4$, $R_{13}$, n are defined as described in the description.

When in the Formula Ia, X is O, Y is N, and $R_4$ is $CH_3C(=O)CH_2$—, the compound of Formula Ia may be prepared by the following scheme:

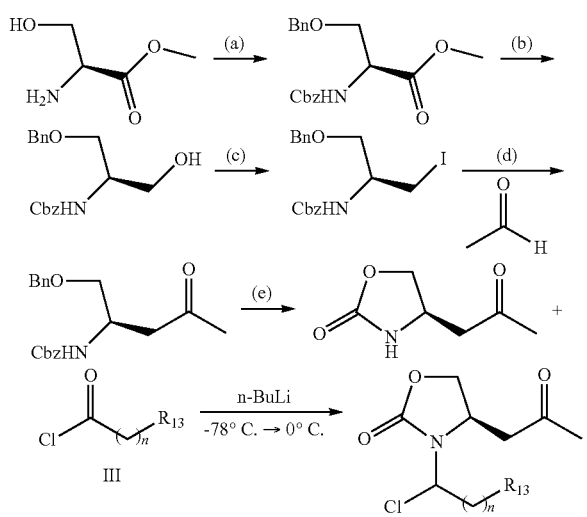

(a) (i) CbzCl, Et₃N, EtOAc, (ii) BnBr, NaH, THF;
(b) DIBAL—H, THF, 0° C.;
(c) I₂, PPh₃, 0° C.;
(d)(i) SmI₂, THF, -78° C., (ii) DMP, CH₂Cl₂, 0° C.;
(e)(i) H₂, Pd/C, (ii) CDI or BTC.

wherein: n, $R_{13}$ are defined as described in the description.

When in the Formula Ia, X is O, Y is N, and $R_4$ is $(CH_3)_2NCH_2$—, the compound of Formula Ia may be prepared by the following scheme:

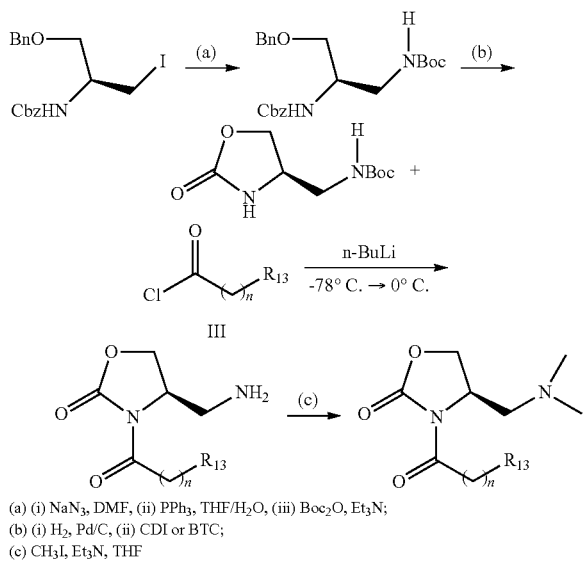

(a) (i) NaN₃, DMF, (ii) PPh₃, THF/H₂O, (iii) Boc₂O, Et₃N;
(b) (i) H₂, Pd/C, (ii) CDI or BTC;
(c) CH₃I, Et₃N, THF wherein: n, $R_{13}$ are defined as described in the description.

In a particular embodiment, the compound of Formula Ia according to the invention is synthesized by the following method: at −78° C., to a tetrahydrofuran (THF) solution containing Oxazolidinone (44 mg, 0.5 mmol), a hexane solution containing n-butyl lithium (0.55 mmol, 0.2 mL) is slowly added dropwisely. After stirring for 10 min at the temperature, a tetrahydrofuran solution containing acyl chloride (0.55 mmol, 1 mL) is added dropwisely to the reaction solution. The reaction solution is stirred at −78° C. for 0.5 h, the temperature is increased slowly to room temperature within 4 h, and the reaction solution was stirred at room temperature for 1 h. After the reaction, saturated NH₄Cl solution (5 mL) is added dropwisely to the reaction solution, ethyl acetate is used to extract the water phase for three times, the ethyl acetate phases are combined, and dried with anhydrous sodium sulfate, ethyl acetate is removed by evaporation under reduced pressure, and the residue is purified by silica gel chromatography to obtain the corresponding compound, wherein the solvent for purification is a mixture of ethyl acetate and petroleum ether, the ratio of which by volume is ethyl acetate:petroleum ether=1:5~1:1.

The compound of Formula I or Ia according to the invention achieves the treatment of pain by inhibiting endocannabinoid hydrolase activity.

The endocannabinoid hydrolases described herein include Fatty Acid Amide Hydrolase (FAAH) and N-acylethanolamide hydrolyzing acid amidase (NAAA).

Inhibition of endocannabinoid hydrolase activity as described herein refers to selective inhibition of NAAA activity or selective inhibition of FAAH activity or inhibition of both NAAA and FAAH activity.

The term "a pharmaceutically acceptable salt" used herein refers to a salt, a prodrug or a solution of the compound according to the invention, which is suitable for contact with human and animal tissue within the correct medical judgment range, without excessive toxicity, excessive emergency response to stimulation, and the like, and has a reasonable benefit/risk ratio.

The term "selective inhibition of NAAA activity" used herein means that the compound in a given administration concentration (e.g., in an effective amount) can inhibit the hydrolysis of a substrate with NAAA in organism, without inhibiting the hydrolysis of a substrate with FAAH in organism.

The term "selective inhibition of FAAH activity" used herein means that the compound in a given administration concentration (e.g., in an effective amount) can inhibit the hydrolysis of a substrate with FAAH in organism, without inhibiting the hydrolysis of a substrate with NAAA in organism.

The term "inhibition of both NAAA and FAAH activity" used herein means that the compound in a given administration concentration (e.g., in an effective amount) can inhibit both the hydrolysis of a substrate with FAAH in organism and the hydrolysis of a substrate with NAAA in organism.

The compound of Formula I or Ia according to the invention may be used directly or in a form of its pharmaceutically acceptable salt, hydrate or solvate. The pharmaceutically acceptable salt of the compound of Formula I or Ia include a salt formed by the reaction with a pharmaceutically acceptable inorganic or organic acid, or a pharmaceutically acceptable inorganic or organic base. Examples of suitable acid addition salts include salts formed with hydrochloric acid, hydrobromic acid, sulphuric acid, phosphoric acid, nitric acid, perchloric acid, fumaric acid, acetic acid, propionic acid, succinic acid, glycolic acid, formic acid, lactic acid, maleic acid, tartaric acid, citric acid, pamoic acid, malonic acid, hydroxymaleic acid, phenylacetic acid, glutamic acid, benzoic acid, salicylic acid, fumaric acid, toluene sulfonic acid, mesilate, naphthalene-2-sulfonic acid, benzenesulfonic acid, naphtholcarboxylic acid, hydriodic acid, malic acid, tannic acid, etc. Examples of suitable base addition salts include salts formed with Na, Li, K, Mg, Al, Ca, Zn, N,N'-dibenzylethylenediamine, chloroprocaine, choline, diethanolamine, ethylenediamine, N-methylglucamine, procaine, etc. When the compound according to the invention is mentioned herein, it includes the compound of Formula I or Ia, and a pharmaceutically acceptable salt, a hydrate or a solvate thereof.

According to the invention, a pharmaceutical composition comprises at least one compound of Formula I or Ia according to the invention, and a conventional pharmaceutical carrier or excipient. The pharmaceutical composition may be administered by routes such as oral or parenteral route. The pharmaceutical composition according to the invention may be prepared into various dosage forms by conventional methods in the art, including, but not limited to tablets, capsules, solutions, suspensions, granules or injections, etc., and may be administered, for example by oral or parenteral route.

In addition, it should be pointed out that the dosage of and method of using the compound according to the invention depend on many factors, including age, body weight, gender, and natural health condition of patient, nutritional status, activity of the compound, administration period, metabolic rate, severity of disease, and subjective judgment made by physician. The preferred dosage is between 0.01 and 100 mg/kg body weight/day.

Beneficial Technical Effects of the Invention

The compound of Formula I or Ia according to the invention achieves the treatment of pains by inhibiting endocannabinoid hydrolase activity. Experiments show that the compound of Formula I or Ia according to the invention can inhibit NAAA and/or FAAH activity, significantly inhibit central neuropathic pain in mice, significantly inhibit celiac inflammatory pain in mice, significantly inhibit headache caused by nitroglycerin in mice, and significantly inhibit osteoarthritis pain in rats.

Furthermore, the compound of Formula I or Ia according to the invention has good stability, has a half-life of above 24 h at acidic or basic conditions, has a half-life of above 120 min in rat plasma, and is much more stable than the reported β-lactam type NAAA inhibitor (β-lactam type NAAA inhibitors has a half-life of below 15 min in rat plasma). The compound of Formula I or Ia according to the invention has a metabolic half-life of 60-300 min in rats, which is much more stable than the reported β-lactam type NAAA inhibitor (β-lactam type NAAA inhibitor of has a metabolic half-life of below 5 min in rats).

In addition, the compound of Formula I or Ia according to the invention has a low inhibition rate on hERG potassium channel, and has a better cardiac safety than the commercially available analgesics COX2 selective inhibitor celecoxib.

SPECIFIC MODES FOR CARRYING OUT THE INVENTION

Figure 1:
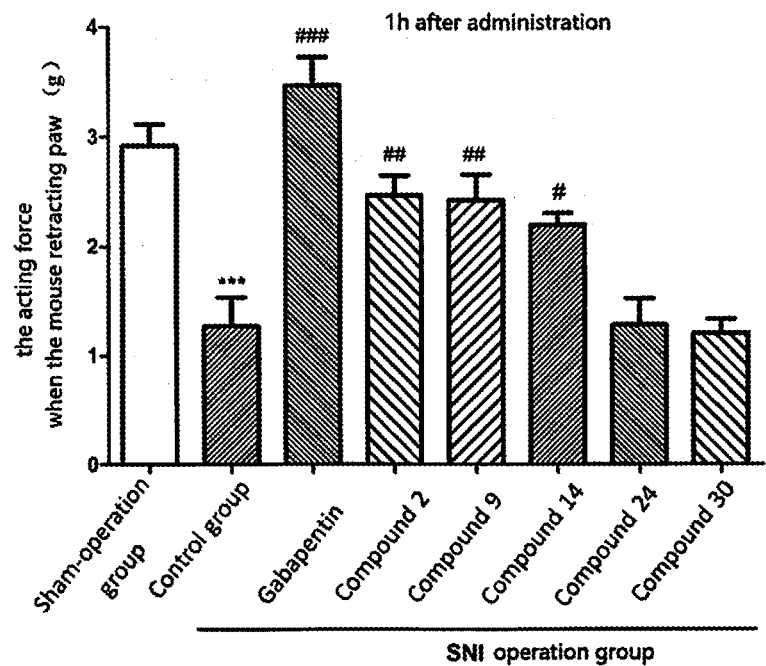
FIG. 1 illustrates the effects of Compounds 2, 9, 14, 24, 30 and the positive control drug gabapentin on SNI neuropathic pain at 1 h after administration.

The embodiments of the invention are described in detail by combining the following examples. However, a person skilled in the art understands that the following examples are only intender to illustrate the invention, and shall not be regarded as defining the scope of the invention. When the particular techniques or conditions are not indicated in Examples, the invention is carried out according to the techniques or conditions described in the prior art documents or according to the product instruction. The reagents or apparatuses, the manufacturers of which are not indicated, are the conventional products that are commercially available.

EXAMPLES

Preparation of Compounds 1-46 by the Following General Synthetic Method

At −78° C., to a tetrahydrofuran (THF) solution containing Oxazolidinone (44 mg, 0.5 mmol), a hexane solution containing n-butyl lithium (0.55 mmol, 0.2 mL) (0.55 mmol, 0.2 mL) was slowly added dropwisely. After stirring for 10 min at the temperature, a tetrahydrofuran solution containing acyl chloride (0.55 mmol, 1 mL) was added dropwisely to the reaction solution. The reaction solution was stirred at −78° C. for 0.5 h, the temperature was increased slowly to room temperature within 4 h, and the reaction solution was stirred at room temperature for 1 h. After the reaction, saturated NH$_4$Cl solution (5 mL) was added dropwisely to the reaction solution, ethyl acetate was used to extract the water phase for three times, the ethyl acetate phases were combined, and dried with anhydrous sodium sulfate, ethyl acetate was removed by evaporation under reduced pressure, and the residue was purified by silica gel chromatography to obtain the corresponding compound, wherein the solvent for purification was a mixture of ethyl acetate and petroleum ether, the ratio of which by volume was ethyl acetate:petroleum ether=1:5~1:1.

Palmitoyl Oxazolidinone (1)

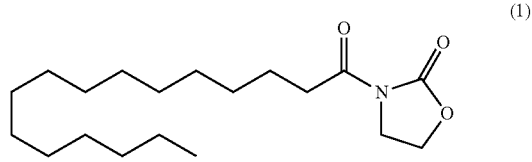 [SMILES: CCCCCCCCCCCCCCCC(=O)N1CCOC1=O]

By the general synthetic method 1 (solvent for purification: ethylacetate:petroleum ether=1:5, the acyl chloride was palmitoyl chloride), the reaction was carried out to obtain product 1 (83 mg; yield: 51%, amorphous white powder).

IR (film) vmax: 2914, 2846, 1765, 1699, 1386 cm−1; 1H NMR (400 MHz, CDCl3) δ 0.88 (t, J=7.2 Hz, 3H), 1.26-1.32 (m, 24H), 1.62-1.69 (m, 2H), 2.91 (t, J=7.6 Hz, 2H), 4.02 (t, J=8.0 Hz, 2H), 4.41 (t, J=8.0 Hz, 2H) ppm; 13C NMR (100 MHz, CDCl3) δ 14.0, 22.6, 24.2, 29.1, 29.3, 29.4, 29.5, 29.6, 29.6, 31.8, 35.0, 42.5, 61.9, 153.5, 173.5 ppm; MS (ESI, m/z): 326 (M+H)+; Anal. calcd for C19H35NO3:C, 70.11; H, 10.84; N, 4.30. Found: C, 70.13; H, 10.86; N, 4.32.

Phenylhexanoyl Oxazolidinone (2)

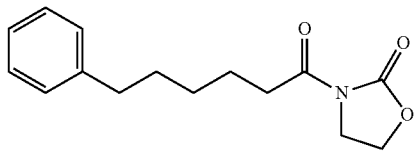

(2)

By the general synthetic method 1 (solvent for purification: ethylacetate:petroleum ether=1:4, the acyl chloride was phenylhexanoyl chloride), the reaction was carried out to obtain product 2 (41 mg; yield: 31%, amorphous white powder).

IR (film) vmax: 2920, 2858, 1780, 1700, 1388, 1225, 1111, 1039 cm−1; 1H NMR (400 MHz, CDCl3) δ 1.36-1.44 (m, 2H), 1.61-1.73 (m, 4H), 2.61 (t, J=7.6 Hz, 2H), 2.90 (t, J=7.6 Hz, 2H), 3.97 (t, J=8.4 Hz, 2H), 4.36 (t, J=8.4 Hz, 2H), 7.16-7.18 (m, 3H), 7.24-7.28 (m, 2H) ppm; 13C NMR (100 MHz, CDCl3) δ 24.0, 28.6, 31.1, 34.9, 35.6, 42.4, 61.9, 125.5, 128.2, 128.3, 142.4, 153.4, 173.3 ppm; MS (ESI, m/z): 262 (M+H)+; HRMS (ESI) calcd for [C15H20NO3]+ (M+H+): 262.1438; found: 262.1451; Anal. calcd for C15H19NO3:C, 68.94; H, 7.33; N, 5.36. Found: C, 68.70; H, 7.31; N, 5.38.

Phenylheptanoyl Oxazolidinone (3)

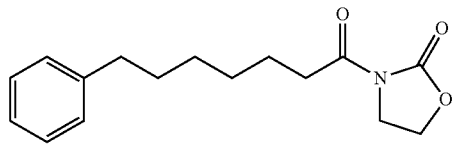

(3)

By the general synthetic method 1 (solvent for purification: ethylacetate:petroleum ether=1:4, the acyl chloride was phenylheptanoyl chloride), the reaction was carried out to obtain product 3 (61 mg; yield: 44%, amorphous white powder).

IR (film) vmax: 2918, 2850, 1781, 1703, 1386, 1225, 1039 cm−1; 1H NMR (400 MHz, CDCl3) δ 1.35-1.42 (m, 4H), 1.58-1.69 (m, 4H), 2.60 (t, J=7.6 Hz, 2H), 2.90 (t, J=7.6 Hz, 2H), 3.98 (t, J=8.4 Hz, 2H), 4.36 (t, J=8.4 Hz, 2H), 7.16-7.17 (m, 3H), 7.24-7.28 (m, 2H) ppm; 113C NMR (100 MHz, CDCl3) δ 24.1, 28.9, 28.9, 31.2, 35.0, 35.8, 42.4, 61.9, 125.5, 128.1, 128.3, 142.6, 153.5, 173.4 ppm; MS (ESI, m/z): 276 (M+H)+; Anal. calcd for C16H21NO3:C, 69.79; H, 7.69; N, 5.09. Found: C, 69.83; H, 7.68; N, 5.10.

Phenyloctanoyl Oxazolidinone (4)

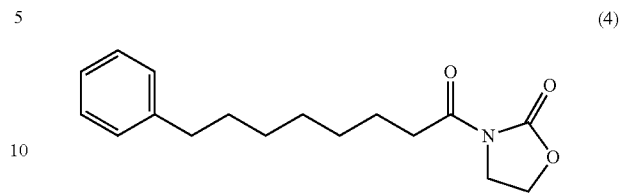

(4)

By the general synthetic method 1 (solvent for purification: ethylacetate:petroleum ether=1:4, the acyl chloride was phenyloctanoyl chloride), the reaction was carried out to obtain product 4 (61 mg; yield: 44%, amorphous white powder).

IR (film) vmax: 2920, 2848, 1780, 1703, 1386, 1225, 1020 cm−1; 1H NMR (400 MHz, CDCl3) δ 1.35-1.42 (m, 4H), 1.58-1.69 (m, 4H), 2.60 (t, J=7.6 Hz, 2H), 2.90 (t, J=7.6 Hz, 2H), 3.98 (t, J=8.4 Hz, 2H), 4.36 (t, J=8.4 Hz, 2H), 7.16-7.17 (m, 3H), 7.24-7.28 (m, 2H) ppm; 113C NMR (100 MHz, CDCl3) 24.1, 28.9, 28.9, 31.2, 35.0, 35.8, 42.4, 61.9, 125.5, 128.1, 128.3, 142.6, 153.5, 173.4 ppm; MS (ESI, m/z): 290 (M+H)+; Anal. calcd for C17H23NO3:C, 70.56; H, 8.01; N, 4.84. Found: C, 70.61; H, 7.99; N, 4.85.

3-Thienylhexanoyl Oxazolidinone (5)

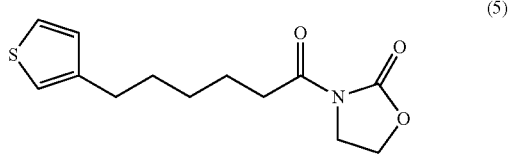 [SMILES: O=C(CCCCCc1ccsc1)N1CCOC1=O]

(5)

By the general synthetic method 1 (solvent for purification: ethylacetate:petroleum ether=1:3, the acyl chloride was 3-thienylhexanoyl chloride); the reaction was carried out to obtain product 5 (57 mg; yield: 43%, amorphous white powder).

IR (film) vmax: 2917, 2849, 1777, 1697, 1386, 1222 cm−1; 1H NMR (400 MHz, CDCl3) δ 1.36-1.44 (m, 2H), 1.62-1.73 (m, 4H), 2.63 (t, J=7.6 Hz, 2H), 2.90 (t, J=7.6 Hz, 2H), 3.98 (t, J=8.0 Hz, 2H), 3.37 (t, J=8.0 Hz, 2H), 6.91-6.92 (m, 2H), 7.21-7.23 (m, 1H) ppm; 13C NMR (100 MHz, CDCl3) δ 23.9, 28.6, 29.9, 30.1, 34.9, 42.4, 61.9, 119.8, 125.0, 128.1, 142.7, 153.4, 173.3 ppm; MS (ESI, m/z): 268 (M+H)+; Anal. calcd for C13H17NO3S:C, 58.40; H, 6.41. Found: C, 58.57; H, 6.40.

Cyclohexylhexanoyl Oxazolidinone (6)

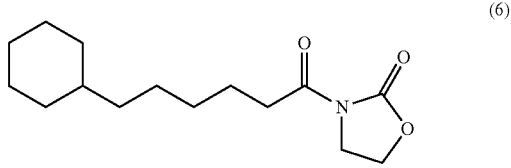 [SMILES: O=C(CCCCCC1CCCCC1)N1CCOC1=O]

(6)

By the general synthetic method 1 (solvent for purification: ethylacetate:petroleum ether=1:5, the acyl chloride was cyclohexylhexanoyl chloride), the reaction was carried out to obtain product 6 (57 mg; yield: 43%, amorphous white powder).

IR (film) vmax: 2917, 2849, 1577, 1541, 1468, 1384, 1068, 1023 cm−1; 1H NMR (400 MHz, CDCl3) δ 0.82-0.90 (m, 2H), 1.15-1.23 (m, 6H), 1.32-1.34 (m, 4H), 1.63-1.70 (m, 7H), 2.92 (t, J=7.6 Hz, 2H), 4.03 (t, J=8.0 Hz, 2H), 4.42 (t, J=8.0 Hz, 2H) ppm; 13C NMR (100 MHz, CDCl3) δ 24.3, 26.4, 26.5, 26.7, 29.4, 33.4, 25.0, 37.3, 37.6, 42.5, 61.9, 153.5, 173.6 ppm; MS (ESI, m/z): 268 (M+H)+; Anal. calcd for C15H25NO3:C, 67.38; H, 9.42; N, 5.24. Found: C, 67.15; H, 9.41; N, 5.25.

3-Furylhexanoyl Oxazolidinone (7)

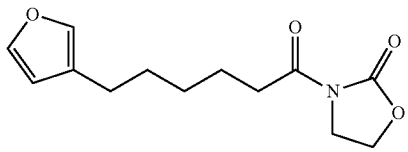 [SMILES: O=C(CCCCCc1ccoc1)N1CCOC1=O]

(7)

By the general synthetic method 1 (solvent for purification: ethylacetate:petroleum ether=1:3, the acyl chloride was 3-furylhexanoyl chloride), the reaction was carried out to obtain product 7 (6.3 mg; yield: 5%, white oily substance).

1H NMR (400 MHz, CDCl3) δ 1.34-1.43 (m, 2H), 1.52-1.73 (m, 4H), 2.61 (t, J=7.6 Hz, 2H), 2.90 (t, J=7.6 Hz, 2H), 3.98 (t, J=8.0 Hz, 2H), 3.37 (t, J=8.0 Hz, 2H), 6.25 (br, 1H), 7.19 (br, 1H), 7.33 (t, J=1.4 Hz, 1H) ppm; 13C NMR (100 MHz, CDCl3) δ 24.3, 24.0, 28.6, 31.1, 34.9, 42.4, 61.9, 110.9, 124.8, 138.7, 142.6, 153.4, 173.3 ppm; MS (ESI, m/z): 252 (M+H)+

3-Fluorophenylhexanoyl Oxazolidinone (8)

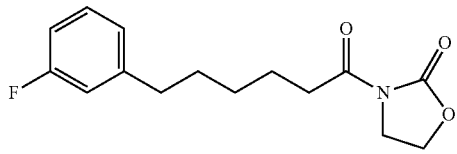 [SMILES: O=C(CCCCCc1cccc(F)c1)N1CCOC1=O]

(8)

By the general synthetic method 1 (solvent for purification: ethylacetate:petroleum ether=1:5, the acyl chloride was 3-fluorophenylhexanoyl chloride), the reaction was carried out to obtain product 8 (57 mg; yield: 51%, amorphous white powder).

IR (film) vmax: 2918, 2850, 1779, 1699, 1617, 1585, 1387, 1223, 1044 cm−1; 1H NMR (400 MHz, CDCl3) 1.36-1.44 (m, 2H), 1.61-1.74 (m, 4H), 2.61 (t, J=7.6 Hz, 2H), 2.92 (t, J=7.6 Hz, 2H), 4.00 (t, J=8.4 Hz, 2H), 4.40 (t, J=8.4 Hz, 2H), 6.84-6.88 (m, 2H), 6.94 (d, J=7.5 Hz, 1H), 7.19-7.24 (m, 1H) ppm; 13C NMR (100 MHz, CDCl3) δ 24.0, 28.6, 30.8, 34.9, 35.4, 42.5, 61.9, 112.4, 112.6, 115.1, 115.3, 124.0, 124.1, 145.0, 145.1, 153.5, 161.7, 164.1, 173.4 ppm; MS (ESI, m/z): 280 (M+H)+; Anal. calcd for C15H18FNO3:C, 64.50; H, 6.50; N, 5.01. Found: C, 64.37; H, 6.49; N, 5.00.

3-Chlorophenylhexanoyl Oxazolidinone (9)

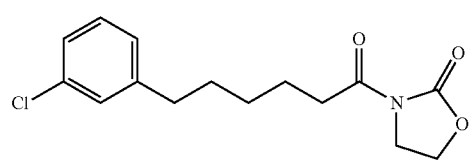 [SMILES: O=C(CCCCCc1cccc(Cl)c1)N1CCOC1=O]

(9)

By the general synthetic method 1 (solvent for purification: ethylacetate:petroleum ether=1:3, the acyl chloride was 3-chlorophenylhexanoyl chloride), the reaction was carried out to obtain product 9 (57 mg; yield: 51%, amorphous white powder).

IR (film) vmax: 2917, 2849, 1777, 1692, 1573, 1537, 1468, 1383, 1202, 1066, 1036 cm−1; 1H NMR (400 MHz, CDCl3) δ 1.35-1.43 (m, 2H), 1.60-1.73 (m, 4H), 2.59 (t, J=7.6 Hz, 2H), 2.90 (t, J=7.6 Hz, 2H), 3.99 (t, J=8.3 Hz, 2H), 4.39 (t, J=8.3 Hz, 2H), 7.04 (d, J=7.3 Hz, 1H), 7.13-7.20 (m, 3H) ppm; 13C NMR (100 MHz, CDCl3) δ 23.9, 28.5, 30.8, 34.9, 35.3, 43.4, 61.9, 125.7, 126.6, 128.4, 129.4, 133.8, 144.5, 153.5, 173.3 ppm; MS (ESI, m/z): 296 (M+H)+; Anal. calcd for C15H18ClNO3:C, 60.91; H, 6.13; N, 4.74. Found: C, 60.77; H, 6.15; N, 4.73.

4-Chlorophenylhexanoyl Oxazolidinone (10)

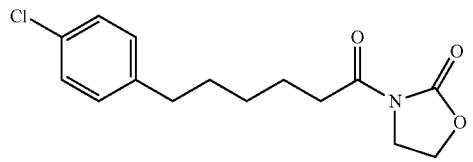 [SMILES: O=C(CCCCCc1ccc(Cl)cc1)N1CCOC1=O]

(10)

By the general synthetic method 1 (solvent for purification: ethylacetate:petroleum ether=1:3, the acyl chloride was 4-chlorophenylhexanoyl chloride), the reaction was carried out to obtain product 10 (55 mg; yield: 49%, amorphous white powder).

IR (film) vmax: 2917, 2849, 1782, 1709, 1579, 1495, 1384, 1222, 1091, 1040 cm−1; 1H NMR (400 MHz, CDCl3) δ 1.35-1.42 (m, 2H), 1.59-1.71 (m, 4H), 2.58 (t, J=7.6 Hz, 2H), 2.90 (t, J=7.6 Hz, 2H), 4.00 (t, J=8.0 Hz, 2H), 4.39 (t, J=8.0 Hz, 2H), 7.09 (d, J=8.2 Hz, 2H), 7.23 (d, J=8.2 Hz, 2H) ppm; 13C NMR (100 MHz, CDCl3) δ 224.0, 24.4, 28.5, 31.0, 34.9, 42.4, 61.9, 128.3, 129.7, 140.9, 153.5, 173.4 ppm; MS (ESI, m/z): 296 (M+H)+; Anal. calcd for C15H18ClNO3:C, 60.91; H, 6.13; N, 4.74. Found: C, 60.83; H, 6.14; N, 4.75.

5-Acetonyl-3'-methylphenylhexanoyl Oxazolidinone (11)

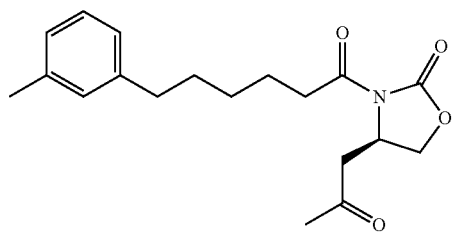 [SMILES: CC(=O)C[C@@H]1COC(=O)N1C(=O)CCCCCc1cccc(C)c1]

(11)

By the general synthetic method 1 (solvent for purification: ethylacetate:petroleum ether=1:3, the acyl chloride was 3-methylphenylhexanoyl chloride, the reaction material oxazolidinone was replaced by 5-acetonyloxazolidinone), the reaction was carried out to obtain product 11 (72 mg; yield: 52%, amorphous white powder).

IR (film) vmax: 2955, 2917, 2849, 1776, 1701, 1571, 1541, 1465, 1384, 1069 cm−1; 1H NMR (400 MHz, CDCl3) δ 1.36-1.44 (m, 2H), 1.60-1.73 (m, 4H), 2.32 (s, 1H), 2.57 (t, J=7.6 Hz, 2H), 2.91 (t, J=7.6 Hz, 2H), 4.00 (t, J=8.2 Hz, 2H), 4.38 (t, J=8.2 Hz, 2H), 6.95-6.98 (m, 3H), 7.16 (dd, J=7.3, 7.3 Hz, 1H) ppm; 13C NMR (100 MHz, CDCl3) δ 21.4, 24.0, 28.7, 31.2, 34.9, 35.6, 42.5, 61.9, 125.4, 126.3, 128.1, 129.2, 137.7, 142.5, 153.5, 173.4 ppm; MS (ESI, m/z): 332 (M+H)+; Anal. calcd for C19H25NO4.

5-Acetonyl-4'-methylphenylvaleryl Oxazolidinone (12)

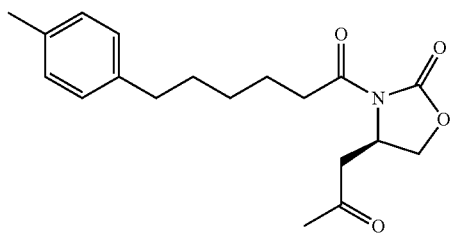 [SMILES: CC(=O)C[C@@H]1COC(=O)N1C(=O)CCCCCc1ccc(C)cc1]

By the general synthetic method 1 (solvent for purification: ethylacetate:petroleum ether=1:3, the acyl chloride was 3-methylphenylhexanoyl chloride, the reaction material oxazolidinone was replaced by 5-acetonyloxazolidinone), the reaction was carried out to obtain product 12 (76 mg; yield: 55%, amorphous white powder).

IR (film) vmax: 2953, 2917, 2849, 1776, 1701, 1579, 1537, 1468, 1384, 1069, 1024 cm-1; 1H NMR (400 MHz, CDCl3) δ 1.35-1.43 (m, 2H), 1.59-1.73 (m, 4H), 2.31 (s, 1H), 2.57 (t, J=7.7 Hz, 2H), 2.90 (t, J=7.7 Hz, 2H), 4.00 (t, J=7.8 Hz, 2H), 4.38 (t, J=7.8 Hz, 2H), 7.04-7.09 (m, 4H) ppm; 13C NMR (100 MHz, CDCl3) δ 20.9, 24.0, 28.7, 31.2, 34.9, 35.2, 42.4, 61.9, 128.2, 128.9, 134.9, 139.4, 153.5, 173.4 ppm; MS (ESI, m/z): 332 (M+H)+; Anal. calcd for C19H25NO4.

3-Bibenzoyl Oxazolidinone (13)

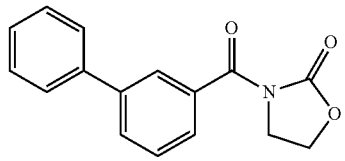 [SMILES: O=C1OCCN1C(=O)c1cccc(-c2ccccc2)c1]

By the general synthetic method 1 (solvent for purification: ethylacetate:petroleum ether=1:2, the acyl chloride was 3-bibenzoyl chloride), the reaction was carried out to obtain product 13 (81 mg; yield: 61%, amorphous white powder).

IR (film) vmax: 2916, 2848, 1633, 1565, 1406, 1107, 1037 cm−1; 1H NMR (400 MHz, CDCl3) δ 4.19-4.20 (m, 2H), 4.52 (br, 2H), 7.36-7.38 (m, 1H), 7.44 (br, 2H), 7.50-7.52 (m, 1H), 7.59-7.61 (m, 3H), 7.77-7.78 (br, 1H), 7.87 (s, 1H) ppm; 13C NMR (100 MHz, CDCl3) δ 43.7, 48.0, 48.2, 48.4, 48.6, 48.9, 62.6, 127.0, 127.6, 128.3, 128.7, 130.8, 140.0, 140.9, 153.9, 170.0 ppm; MS (ESI, m/z): 268 (M+H)+; Anal. calcd for C16H13NO3:C, 71.90; H, 4.90; N, 5.24. Found: C, 71.74; H, 4.89; N, 5.25.

3-Biphenylacetyl Oxazolidinone (14)

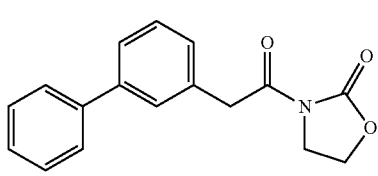 [SMILES: O=C(Cc1cccc(-c2ccccc2)c1)N1CCOC1=O]

By the general synthetic method 1 (solvent for purification: ethylacetate:petroleum ether=1:3, the acyl chloride was 3-biphenylacetyl chloride), the reaction was carried out to obtain product 14 (63 mg; yield: 45%, amorphous white powder).

IR (film) vmax: 2916, 2848, 1776, 1697, 1598, 1478, 1387, 1366, 1223, 1180, 1109 cm-1; 1H NMR (400 MHz, CDCl3) δ 4.02 (t, J=8.0 Hz, 2H), 4.35 (s, 2H), 4.39 (t, J=8.0 Hz, 2H), 7.31 (d, J=7.2 Hz, 1H), 7.34 (d, J=7.2 Hz, 1H), 7.38-7.44 (m, 3H), 7.50 (d, J=7.6 Hz, 1H), 7.55-7.60 (m, 1H) ppm; 13C NMR (100 MHz, CDCl3) δ 41.1, 42.7, 61.9, 126.0, 127.2, 127.3, 128.6, 128.6, 128.7, 128.9, 134.0, 140.8, 141.5, 153.5, 171.2 ppm; MS (ESI, m/z): 282 (M+H)+; Anal. calcd for C17H15NO3:C, 72.58; H, 5.37; N, 4.98. Found: C, 72.71; H, 5.39; N, 4.96.

4-Biphenylacetyl Oxazolidinone (15)

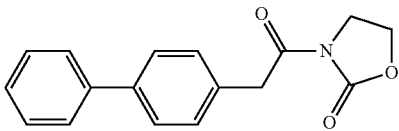

By the general synthetic method 1 (solvent for purification: ethylacetate:petroleum ether=1:3, the acyl chloride was 4-biphenylacetyl chloride), the reaction was carried out to obtain product 15 (65 mg; yield: 46%, amorphous white powder).

IR (film) vmax: 2914, 2844, 1776, 1697, 1578, 1386, 1366, 1025 cm−1; 1H NMR (400 MHz, CDCl3) δ 4.00 (t, J=8.4 Hz, 2H), 4.31 (s, 2H), 4.36 (t, J=8.4 Hz, 2H), 7.33 (t, J=7.6 Hz, 1H), 7.37-7.44 (m, 4H), 7.54-7.58 (m, 4H) ppm; 13C NMR (100 MHz, CDCl3) δ 40.7, 42.6, 61.9, 127.0, 127.2, 128.7, 130.1, 132.5, 140.0, 140.7, 153.4, 171.1 ppm; MS (ESI, m/z): 282 (M+H)+; Anal. calcd for C17H15NO3: C, 72.58; H, 5.37; N, 4.98. Found: C, 72.67; H, 5.38; N, 4.97.

3-Phenoxybenzoyl Oxazolidinone (16)

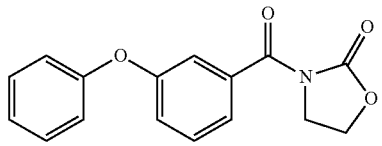 [SMILES: O=C1OCCN1C(=O)c1cccc(Oc2ccccc2)c1]

(16)

By the general synthetic method 1 (solvent for purification: ethylacetate:petroleum ether=1:2, the acyl chloride was 3-phenoxybenzoyl chloride), the reaction was carried out to obtain product 16 (65 mg; yield: 48%, amorphous white powder).

IR (film) vmax: 2917, 2845, 1783, 1682, 1577, 1483, 1436, 1322, 1200 cm-1; 1H NMR (400 MHz, CDCl3) δ 4.14 (t, J=8.0 Hz, 2H), 4.46 (t, J=8.0 Hz, 2H), 7.04 (dd, J=8.6, 1.0 Hz, 2H), 7.12 (dd, J=7.4, 0.9 Hz, 1H), 7.18 (dddd, J=7.2, 7.2, 2.0, 2.0 Hz, 1H), 7.26 (br, 1H), 7.33-7.39 (m, 4H) ppm; 13C NMR (100 MHz, CDCl3) δ 43.6, 62.2, 119.1, 119.1, 122.6, 123.6, 123.7, 129.4, 129.9, 134.3, 153.0, 156.6, 156.8, 169.1 ppm; MS (ESI, m/z): 284 (M+H)+; Anal. calcd for C16H13NO4:C, 67.84; H, 4.63; N, 4.94. Found: C, 68.01; H, 4.64; N, 4.93.

3-Phenoxyphenylacetyl Oxazolidinone (17)

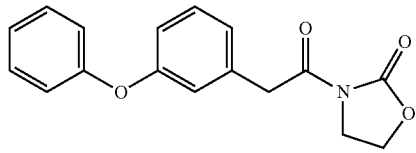 [SMILES: O=C(Cc1cccc(Oc2ccccc2)c1)N1CCOC1=O]

(17)

By the general synthetic method 1 (solvent for purification: ethylacetate:petroleum ether=1:2, the acyl chloride was 3-phenoxyphenylacetyl chloride), the reaction was carried out to obtain product 17 (86 mg; yield: 53%, amorphous white powder).

IR (film) vmax: 2914, 2844, 1777, 1701, 1583, 1486, 1387, 1366, 1269, 1246, 1211 cm-1; 1H NMR (400 MHz, CDCl3) δ 3.99 (t, J=8.0 Hz, 2H), 4.24 (s, 1H), 4.37 (t, J=8.0 Hz, 2H), 6.89 (d, J=7.8 Hz, 1H), 6.96 (s, 1H), 7.01 (dd, J=8.4, 8.4 Hz, 3H), 7.09 (dd, J=7.8 Hz, 1H), 7.25 (d, J=7.8 Hz, 1H), 7.31 (dd, J=8.4, 8.4 Hz, 2H) ppm; 13C NMR (100 MHz, CDCl3) δ 40.9, 42.6, 61.9, 117.4, 118.9, 120.1, 123.2, 124.5, 129.7, 135.3, 153.4, 156.9, 157.2, 170.8 ppm; MS (ESI, m/z): 298 (M+H)+; Anal. calcd for C17H15NO4:C, 68.68; H, 5.09; N, 4.71. Found: C, 68.51; H, 5.08; N, 4.72.

4-Phenoxyphenylacetyl Oxazolidinone (18)

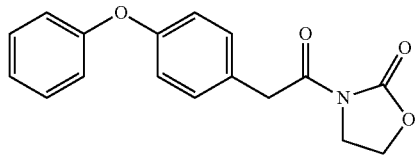 [SMILES: O=C(Cc1ccc(Oc2ccccc2)cc1)N1CCOC1=O]

(18)

By the general synthetic method 1 (solvent for purification: ethylacetate:petroleum ether=1:2, the acyl chloride was 4-phenoxyphenylacetyl chloride), the reaction was carried out to obtain product 18 (88 mg; yield: 59%, amorphous white powder).

IR (film) vmax: 2916, 2848, 1777, 1577, 1537, 1486, 1467, 1385, 1237, 1108, 1040 cm-1; 1H NMR (400 MHz, CDCl3) δ 4.02 (t, J=8.0 Hz, 2H), 4.25 (s, 2H), 4.39 (t, J=8.0 Hz, 2H), 6.95 (d, J=8.4 Hz, 2H), 7.00 (d, J=7.6 Hz, 2H), 7.09 (t, J=7.6 Hz, 1H), 7.27 (d, J=8.4 Hz, 2H), 7.32 (t, J=7.6 Hz, 2H) ppm; 13C NMR (100 MHz, CDCl3) δ 40.3, 42.6, 62.0, 118.8, 118.9, 123.3, 128.2, 129.7, 131.0, 153.4, 156.4, 157.0, 171.3 ppm; MS (ESI, m/z): 298 (M+H)+; Anal. calcd for C17H15NO4:C, 68.68; H, 5.09; N, 4.71. Found: C, 68.73; H, 5.10; N, 4.72.

3-Benzyloxybenzoyl Oxazolidinone (19)

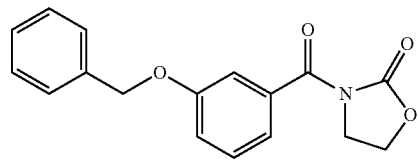 [SMILES: O=C1OCCN1C(=O)c1cccc(OCc2ccccc2)c1]

(19)

By the general synthetic method 1 (solvent for purification: ethylacetate:petroleum ether=1:2, the acyl chloride was 3-benzyloxybenzoyl chloride), the reaction was carried out to obtain product 19 (82 mg; yield: 55%, amorphous white powder).

IR (film) vmax: 2916, 2849, 1785, 1679, 1634, 1579, 1436, 1383, 1325, 1244, 1217, 1196, 1145, 1098, 1037 cm-1; 1H NMR (400 MHz, CDCl3) δ 4.16 (t, J=7.6 Hz, 2H), 4.48 (t, J=7.6 Hz, 2H), 5.08 (s, 2H), 7.14-7.44 (m, 9H) ppm; 13C NMR (100 MHz, CDCl3) δ 43.7, 62.2, 70.3, 115.1, 119.3, 121.7, 127.6, 128.1, 128.6, 129.0, 133.9, 136.5, 153.1, 158.3, 169.5 ppm; MS (ESI, m/z): 298 (M+H)+; Anal. calcd for C17H15NO4:C, 68.68; H, 5.09; N, 4.71. Found: C, 68.81; H, 5.11; N, 4.71.

3-Benzyloxyphenylacetyl Oxazolidinone (20)

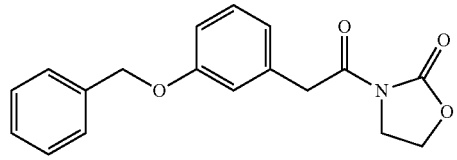 [SMILES: O=C(Cc1cccc(OCc2ccccc2)c1)N1CCOC1=O]

(20)

By the general synthetic method 1 (solvent for purification: ethylacetate:petroleum ether=1:2, the acyl chloride was 3-benzyloxyphenylacetyl chloride), the reaction was carried out to obtain product 20 (76 mg; yield: 49%, amorphous white powder).

IR (film) vmax: 2916, 2849, 1777, 1698, 1583, 1489, 1449, 1387, 1365, 1272, 1224, 1158, 1109, 1039 cm-1; 1H NMR (400 MHz, CDCl3) δ 3.97 (t, J=8.1 Hz, 2H), 4.25 (s, 2H), 4.35 (t, J=8.1 Hz, 2H), 5.04 (s, 2H), 6.88 (d, J=7.9 Hz, 1H), 6.91 (d, J=7.9 Hz, 1H), 6.96 (s, 1H), 7.22 (dd, J=7.9, 7.9 Hz, 1H), 7.30 (dd, J=7.2, 7.2 Hz, 1H), 7.37 (dd, J=7.2, 7.2 Hz, 2H), 7.42 (d, J=7.2 Hz, 2H) ppm; 13C NMR (100 MHz, CDCl3) δ 41.0, 42.6, 61.9, 69.9, 113.7, 116.2, 122.3, 127.5, 127.9, 128.5, 129.5, 135.0, 137.0, 153.4, 158.9, 171.0 ppm; MS (ESI, m/z): 312 (M+H)+; Anal. calcd for C18H17NO4:C, 69.44; H, 5.50; N, 4.50. Found: C, 69.20; H, 5.49; N, 4.51.

4-Benzyloxybenzoyl Oxazolidinone (21)

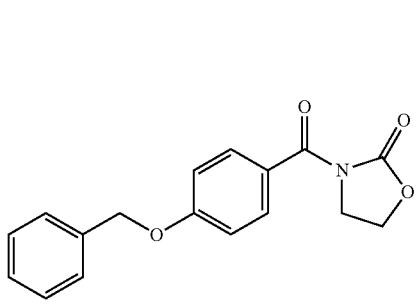 [SMILES: O=C1OCCN1C(=O)c1ccc(OCc2ccccc2)cc1]

By the general synthetic method 1 (solvent for purification: ethylacetate:petroleum ether=1:2, the acyl chloride was 4-benzyloxybenzoyl chloride), the reaction was carried out to obtain product 21 (108 mg; yield: 73%, amorphous white powder).

IR (film) νmax: 2916, 2849, 1774, 1670, 1607, 1512, 1378, 1338, 1249, 1194, 1108, 1024 cm−1; 1H NMR (400 MHz, CDCl3) δ 4.14 (t, J=8.0 Hz, 2H), 4.47 (t, J=8.0 Hz, 2H), 5.11 (s, 2H), 6.99 (d, J=8.8 Hz, 2H), 7.34-7.43 (m, 5H), 7.69 (d, J=8.8 Hz, 2H) ppm; 13C NMR (100 MHz, CDCl3) δ 43.9, 62.2, 70.1, 114.0, 124.7, 127.5, 128.2, 128.6, 131.8, 136.2, 153.5, 162.4, 169.0 ppm; MS (ESI, m/z): 298 (M+H)+; Anal. calcd for C17H15NO4:C, 68.68; H, 5.09; N, 4.71. Found: C, 68.90; H, 5.11; N, 4.69.

4-Benzyloxyphenylacetyl Oxazolidinone (22)

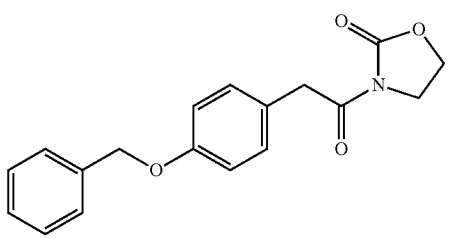 [SMILES: O=C(Cc1ccc(OCc2ccccc2)cc1)N1CCOC1=O]

By the general synthetic method 1 (solvent for purification: ethylacetate:petroleum ether=1:2, the acyl chloride was 4-benzyloxyphenylacetyl chloride), the reaction was carried out to obtain product 22 (77 mg; yield: 50%, amorphous white powder).

IR (film) νmax: 2916, 2849, 1777, 1698, 1607, 1511, 1387, 1365, 1240, 1177, 1111, 1040, 1016 cm−1; 1H NMR (400 MHz, CDCl3) δ 3.96 (t, J=8.0 Hz, 2H), 4.20 (s, 2H), 4.33 (t, J=8.0 Hz, 2H), 5.03 (s, 2H), 6.92 (d, J=8.4 Hz, 2H), 7.22 (d, J=8.4 Hz, 2H), 7.30 (t, J=7.2 Hz, 1H), 7.35-7.42 (m, 4H) ppm; 13C NMR (100 MHz, CDCl3) δ 40.1, 42.6, 61.9, 69.9, 114.8, 125.8, 127.4, 127.9, 128.5, 130.7, 136.9, 153.4, 157.9, 171.5 ppm; MS (ESI, m/z): 312 (M+H)+; Anal. calcd for C18H17NO4:C, 69.44; H, 5.50; N, 4.50. Found: C, 69.65; H, 5.51; N, 4.50.

5-N, N-dimethyl methylamino-4'-phenylethoxylbenzoyl Oxazolidinone (23)

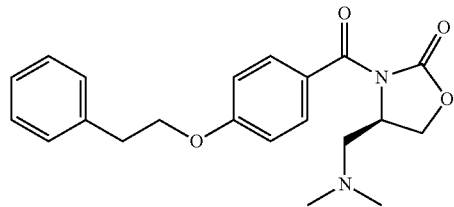 [SMILES: CN(C)C[C@@H]1COC(=O)N1C(=O)c1ccc(OCCc2ccccc2)cc1]

By the general synthetic method 1 (solvent for purification: ethylacetate:petroleum ether=1:1, the acyl chloride was 4-phenylethoxylbenzoyl chloride, the reaction material oxazolidinone was replaced by 5-N,N-dimethyl methylaminooxazolidinone), the reaction was carried out to obtain product 23 (84 mg; yield: 54%, amorphous white powder).

IR (film) νmax: 2916, 2849, 1777, 1672, 1605, 1508, 1384, 1324, 1307, 1254, 1168, 1094, 1029 cm−1; 1H NMR (400 MHz, CDCl3) δ 3.11 (t, J=7.2 Hz, 2H), 4.14 (t, J=8.0 Hz, 2H), 4.22 (t, J=7.2 Hz, 2H), 4.46 (t, J=8.0 Hz, 2H), 6.90 (d, J=8.4 Hz, 2H), 7.23-7.34 (m, 5H), 7.67 (d, J=8.4 Hz, 2H) ppm; 13C NMR (100 MHz, CDCl3) δ 35.6, 43.9, 62.2, 68.8, 113.7, 124.4, 126.6, 128.5, 129.0, 131.8, 137.8, 153.5, 162.5, 169.0 ppm; MS (ESI, m/z): 312 (M+H)+; Anal. calcd for C21H24N2O4:C, 68.46; H, 6.57; N, 7.60; O, 17.37. Found: C, 68.23; H, 6.44; N, 7.78; O, 17.45.

4-Benzylcyclohexanoyl Oxazolidinone (24)

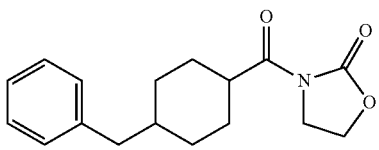

By the general synthetic method 1 (solvent for purification: ethylacetate:petroleum ether=1:5, the acyl chloride was 4-benzylcyclohexanoyl chloride), the reaction was carried out to obtain product 24 (84 mg; yield: 54%, amorphous white powder).

1H NMR (400 MHz, CDCl3) δ 1.53-1.68 (m, 6H), 1.77-1.90 (m, 3H), 2.61-2.63 (m, 2H), 3.60-3.66 (t, 1H), 3.99-4.03 (t, J=8.0 Hz, 2H), 4.36-4.40 (t, J=8.0 Hz, 2H), 7.11-7.19 (m, 3H), 7.25-7.28 (m, 2H) ppm; 13C NMR (100 MHz, CDCl3) δ 25.2, 28.6, 36.4, 39.8, 40.1, 42.8, 61.8, 125.6, 128.1, 129.0, 141.3, 153.1, 176.6 ppm.

N-benzylpiperidine-4-carbonyl Oxazolidinone (25)

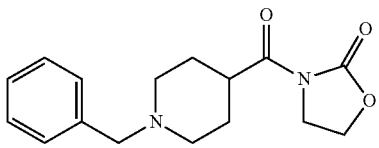 [SMILES: O=C1OCCN1C(=O)C1CCN(Cc2ccccc2)CC1]

By the general synthetic method 1 (solvent for purification: ethylacetate:petroleum ether=1:3, the acyl chloride was N-benzylpiperidine-4-carbonyl chloride), the reaction was carried out to obtain product 25 (27 mg; yield: 46%, amorphous white powder).

1H NMR (400 MHz, CDCl3) δ 1.72-1.83 (m, 4H), 2.64 (m, 1H), 3.92-4.05 (m, 8H), 4.39 (t, J=8.0 Hz, 2H), 7.21-7.25 (m, 3H), 7.28-7.30 (m, 2H) ppm; 13C NMR (100 MHz, CDCl3) δ 27.9, 28.3, 34.7, 38.6, 42.6, 42.8, 60.3, 125.7, 128.4, 130.6, 140.7, 153.1, 176.6 ppm; MS (ESI, m/z): 289 (M+H)+; Anal. calcd for C16H20N2O3:C, 66.65; H, 6.99; N, 9.72; O, 16.65.

Phenylhexanoyl-5-methyl-Oxazolidinone (27)

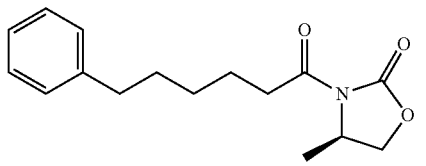 [SMILES: C[C@@H]1COC(=O)N1C(=O)CCCCCc1ccccc1]

(27)

By the general synthetic method 1 (solvent for purification: ethylacetate:petroleum ether=1:4, the acyl chloride was phenylhexanoyl chloride, the reaction material oxazolidinone was replaced by 5-methyloxazolidinone), the reaction was carried out to obtain product 27 (57 mg; yield: 42%, amorphous white powder).

IR (film) vmax: 2937, 2872, 1764, 1725, 1683, 1363, 1231, 1058 cm−1; 1H NMR (400 MHz, CDCl3) δ 0.97 (d, J=5.6 Hz, 3H), 1.32-1.40 (m, 2H), 1.58-1.62 (m, 4H), 2.63 (t, J=7.5 Hz, 2H), 2.87 (t, J=7.5 Hz, 2H), 4.05 (m, 1H), 4.42 (dd, J=10.6, 8.4 Hz, 2H), 7.15-7.18 (m, 3H), 7.24-7.29 (m, 2H) ppm; MS (ESI, m/z): 276 (M+H)+; C16H21NO3, C, 69.79; H, 7.69; N, 5.09; O, 17.43.

4-Hydroxyphenylhexanoyl Oxazolidinone (31)

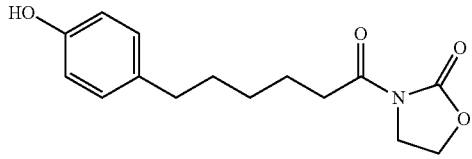 [SMILES: O=C(CCCCCc1ccc(O)cc1)N1CCOC1=O]

(31)

By the general synthetic method 1 (solvent for purification: ethylacetate:petroleum ether=11:2, the acyl chloride was p-hydroxyphenylhexanoyl chloride), the reaction was carried out to obtain product 31 (53 mg; yield: 68%, amorphous white powder).

IR (film) vmax: 3362, 3130, 2837, 1764, 1717, 1538, 1519, 1267, 1243, 1075 cm−1; 1H NMR (400 MHz, CDC3) δ 1.38 (m, 2H), 1.62-1.68 (m, 4H), 2.27 (s, 1H), 2.54 (t, J=7.0 Hz, 2H), 2.96 (t, J=7.0 Hz, 2H), 4.07 (t, J=7.2 Hz, 2H), 4.29 (t, J=7.2 Hz, 2H), 6.82 (d, J=6.9 Hz, 2H), 7.43 (d, J=6.9 Hz, 2H) ppm; 13C NMR (100 MHz, CDCl3) δ 21.7, 23.8, 26.7, 30.5, 31.3, 35.6, 41.7, 60.8, 114.7, 134.9, 136.4, 162.8, 172.4 ppm; MS (ESI, m/z): 278 (M+H)+; Anal. calcd for C15H19NO4:C, 64.97; H, 6.91; N, 5.05; O, 23.08.

3-Methylphenylhexanoyl Oxazolidinone (32)

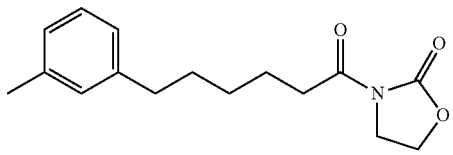 [SMILES: Cc1cccc(CCCCCC(=O)N2CCOC2=O)c1]

(32)

By the general synthetic method 1 (solvent for purification: ethylacetate:petroleum ether=1:5, the acyl chloride was 3-methylphenylhexanoyl chloride), the reaction was carried out to obtain product 32 (72 mg; yield: 52%, amorphous white powder).

IR (film) vmax: 2955, 2917, 2849, 1776, 1701, 1571, 1541, 1465, 1384, 1069 cm−1; 1H NMR (400 MHz, CDCl3) δ 1.36-1.44 (m, 2H), 1.60-1.73 (m, 4H), 2.32 (s, 3H), 2.57 (t, J=7.6 Hz, 2H), 2.91 (t, J=7.6 Hz, 2H), 4.00 (t, J=8.2 Hz, 2H), 4.38 (t, J=8.2 Hz, 2H), 6.95-6.98 (m, 3H), 7.16 (dd, J=7.3, 7.3 Hz, 1H) ppm; 13C NMR (100 MHz, CDCl3) δ 21.4, 24.0, 28.7, 31.2, 34.9, 35.6, 42.5, 61.9, 125.4, 126.3, 128.1, 129.2, 137.7, 142.5, 153.5, 173.4 ppm; MS (ESI, m/z): 276 (M+H)+; Anal. calcd for C16H21NO3:C, 69.79; H, 7.69; N, 5.09. Found: C, 69.61; H, 7.67; N, 5.10.

4-Methylphenylhexanoyl Oxazolidinone (33)

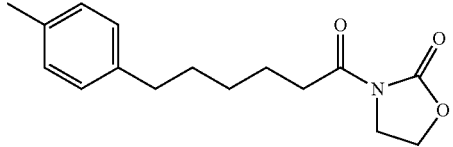 [SMILES: Cc1ccc(CCCCCC(=O)N2CCOC2=O)cc1]

(33)

By the general synthetic method 1 (solvent for purification: ethylacetate:petroleum ether=1:5, the acyl chloride was p-methylphenylhexanoyl chloride), the reaction was carried out to obtain product 33 (148 mg; yield: 72%, amorphous white powder).

IR (film) vmax: 3034, 2921, 2850, 1700, 1458, 1405 cm−1; 1H NMR (400 MHz, CDCl3) δ 1.34-1.41 (m, 2H), 1.58-1.70 (m, 4H), 2.31 (s, 3H), 2.34 (t, J=7.6 Hz, 2H), 2.56 (t, J=7.6 Hz, 2H), 7.05 (d, J=8.4 Hz, 2H), 7.08 (d, J=8.4 Hz, 2H) ppm; 13C NMR (100 MHz, CDCl3) δ 20.9, 24.5, 28.6, 31.1, 34.0, 35.2, 128.2, 128.9, 135.0, 139.3, 153.5, 180.4 ppm; MS (ESI, m/z): 207 (M+H)+; Anal. calcd for C13H18O2:C, 75.69; H, 8.80. Found: C, 75.78; H, 8.82.

Piperidin-3-yl-hexanoyl Oxazolidinone (34)

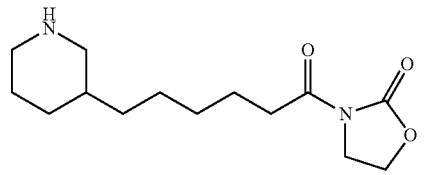 [SMILES: O=C(CCCCCC1CCCNC1)N1CCOC1=O]

(34)

By the general synthetic method 1 (solvent for purification: ethylacetate:petroleum ether=1:3, the acyl chloride was piperidin-3-yl-hexanoyl chloride), the reaction was carried out to obtain product 34 (26 mg; yield: 36%, amorphous white powder).

IR (film) νmax: 3314, 3017, 1577, 1541, 1468, 1023 cm−1; 1H NMR (400 MHz, CDCl3) δ 0.82-0.90 (m, 2H), 1.15-1.23 (m, 6H), 1.63-1.70 (m, 5H), 2.92 (t, J=7.6 Hz, 2H), 3.39 (t, J=7.2 Hz, 2H), 3.54 (t, J=7.2 Hz, 2H), 4.03 (t, J=8.0 Hz, 2H), 4.42 (t, J=8.0 Hz, 2H) ppm; 13C NMR (100 MHz, CDCl3) δ 24.3, 26.4, 29.4, 33.4, 25.0, 37.3, 37.6, 42.5, 42.7, 46.6, 61.9, 153.5, 173.6 ppm; MS (ESI, m/z): 269 (M+H)+; Anal. calcd for C14H24N2O3:C, 62.66; H, 9.01; N, 10.44, O, 17.89.

Phenylvaleryl Oxazolidinone (35)

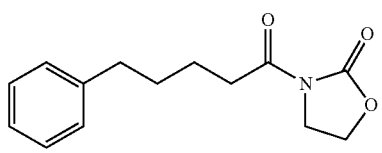 [SMILES: O=C(CCCCc1ccccc1)N1CCOC1=O]

(35)

By the general synthetic method 1 (solvent for purification: ethylacetate:petroleum ether=1:5, the acyl chloride was phenylvaleryl chloride), the reaction was carried out to obtain product 35 (69 mg; yield: 56%, amorphous white powder).

IR (film) νmax: 2924, 2858, 1780, 1700, 1497, 1478, 1453, 1388, 1225, 1111, 1040 cm-1; 1H NMR (400 MHz, CDCl3) δ 1.69-1.71 (m, 4H), 2.64 (t, J=7.2 Hz, 2H), 2.94 (t, J=7.2 Hz, 2H), 3.98 (t, J=8.4 Hz, 2H), 4.37 (t, J=8.4 Hz, 2H), 7.17-7.19 (m, 3H), 7.25-7.29 (m, 2H) ppm; 13C NMR (100 MHz, CDCl3) δ23.8, 30.7, 34.8, 35.5, 42.4, 61.9, 125.7, 128.2, 128.3, 142.1, 153.5, 173.3 ppm; MS (ESI, m/z): 248 (M+H)+; Anal. calcd for C14H17NO3:C, 68.00; H, 6.93; N, 5.66. Found: C, 68.20; H, 6.91; N, 5.67.

3-Chlorophenylvaleryl Oxazolidinone (36)

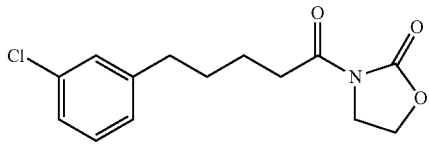 [SMILES: O=C(CCCCc1cccc(Cl)c1)N1CCOC1=O]

(36)

By the general synthetic method 1 (solvent for purification: ethylacetate:petroleum ether=1:4, the acyl chloride was 3-chlorophenylvaleryl chloride), the reaction was carried out to obtain product 36 (32 mg; yield: 43%, amorphous white powder).

IR (film) νmax: 2917, 2849, 1777, 1692, 1573, 1537, 1468, 1383, 1202, 1066, 1036 cm-1; 1H NMR (400 MHz, CDCl3) δ 1.35-1.43 (m, 2H), 1.60-1.73 (m, 2H), 2.59 (t, J=7.6 Hz, 2H), 2.90 (t, J=7.6 Hz, 2H), 3.99 (t, J=8.3 Hz, 2H), 4.39 (t, J=8.3 Hz, 2H), 7.04 (d, J=7.3 Hz, 1H), 7.13-7.20 (m, 3H) ppm; 13C NMR (100 MHz, CDCl3) δ 23.9, 30.8, 34.9, 35.3, 43.4, 61.9, 125.7, 126.6, 128.4, 129.4, 133.4, 144.5, 153.5, 173.5 ppm; MS (ESI, m/z): 282 (M+H)+; Anal. calcd for C14H16ClNO3:C, 59.68; H, 5.72; Cl, 12.58; N, 4.97; O, 17.04.

4-Fluorophenylvaleryl Oxazolidinone (37)

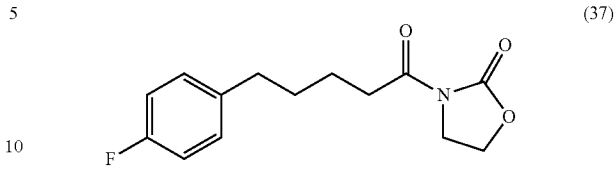

(37)

By the general synthetic method 1 (solvent for purification: ethylacetate:petroleum ether=1:4, the acyl chloride was 4-fluorophenylvaleryl chloride), the reaction was carried out to obtain product 37 (73 mg; yield: 62%, amorphous white powder).

IR (film) νmax: 2926, 2852, 1774, 1709, 1371, 1045 cm−1; 1H NMR (400 MHz, CDCl3) δ 1.35-1.42 (m, 2H), 1.64 (m, 2H), 2.58 (t, J=7.6 Hz, 2H), 2.90 (t, J=7.6 Hz, 2H), 4.04 (t, J=8.0 Hz, 2H), 4.35 (t, J=8.0 Hz, 2H), 7.07 (d, J=8.2 Hz, 2H), 7.23 (d, J=8.2 Hz, 2H) ppm; 13C NMR (100 MHz, CDCl3) δ 23.8, 24.3, 31.4, 34.6, 42.5, 62.6, 128.3, 128.7, 140.9, 153.5, 173.4 ppm; MS (ESI, m/z): 266 (M+H)+; Anal. calcd for C14H16FNO3:C, 63.39; H, 6.08; F, 7.16; N, 5.28; O, 18.09.

2,4-Dichlorophenylheptanoyl Oxazolidinone (38)

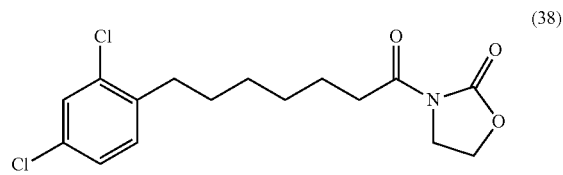

(38)

By the general synthetic method 1 (solvent for purification: ethylacetate:petroleum ether=1:3, the acyl chloride was 2,4-dichlorophenylheptanoyl chloride), the reaction was carried out to obtain product 38 (7.6 mg; yield: 14%, amorphous white powder).

IR (film) νmax: 2928, 2860, 1784, 1706, 1617, 1223, 1067, 986 cm−1; 1H NMR (400 MHz, CDCl3) δ 1.36-1.48 (m, 2H), 1.65-1.78 (m, 6H), 2.67 (t, J=7.6 Hz, 2H), 2.91 (t, J=7.6 Hz, 2H), 4.04 (t, J=8.4 Hz, 2H), 4.42 (t, J=8.4 Hz, 2H), 6.88-6.92 (m, 3H) ppm; 13C NMR (100 MHz, CDCl3) δ 24.2, 24.6, 28.6, 30.5, 35.1, 35.4, 42.5, 61.9, 112.4, 112.6, 116.7, 124.3, 124.6, 145.1, 153.5, 173.4 ppm; MS (ESI, m/z): 344:346 (3:2, M+H)+; Anal. calcd for C16H19Cl2NO3:C, 55.83; H, 5.56; Cl, 20.60; N, 4.07; O, 13.94.

3,4-Dihydroxyphenylhexanoyl Oxazolidinone (39)

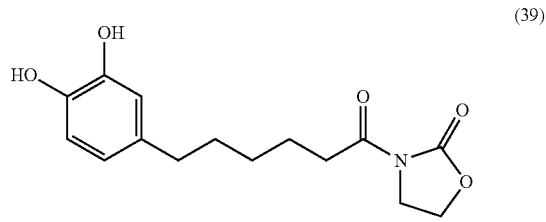

(39)

By the general synthetic method 1 (solvent for purification: ethylacetate:petroleum ether=1:1, the acyl chloride was 3,4-dihydroxyphenylhexanoyl chloride), the reaction was carried out to obtain product 39 (47 mg; yield: 36%, amorphous white powder).

IR (film) vmax: 3130, 3017, 2939, 1785, 1724, 1242, 1085 cm−1; 1H NMR (400 MHz, CDCl3) δ 1.35 (m, 2H), 1.68-1.74 (m, 4H), 2.76 (t, J=7.6 Hz, 2H), 2.87 (t, J=7.6 Hz, 2H), 4.03 (t, J=8.4 Hz, 2H), 4.39 (t, J=8.4 Hz, 2H), 6.90 (s, 1H), 7.07 (d, 1H), 7.46 (d, 1H) ppm; 13C NMR (100 MHz, CDCl3) δ 24.2, 28.3, 31.4, 33.7, 36.4, 42.5, 61.3, 105.3, 114.8, 124.7, 148.4, 153.5, 158.5, 159.7, 173.4 ppm; MS (ESI, m/z): 294 (M+H)+; Anal. calcd for C15H19NO5:C, 61.42; H, 6.53; N, 4.78; O, 27.27.

Palmitoyl Imidazolidinone (40)

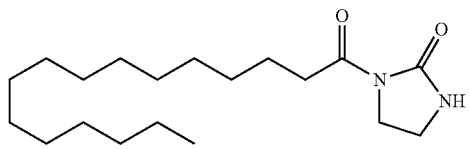 [SMILES: CCCCCCCCCCCCCCCC(=O)N1CCNC1=O]

By a method similar to the general synthetic method 1 (solvent for purification: ethyl acetate:petroleum ether=1:5, the acyl chloride was palmitoyl chloride, the reaction material oxazolidinone was replaced by imidazolidinone), the reaction was carried out to obtain product 40 (37 mg; yield: 54%, amorphous white powder).

IR (film) vmax: 3312, 3017, 1768, 1715, 1388 cm−1; 1H NMR (400 MHz, CDCl3) δ 0.88 (t, J=7.2 Hz, 3H), 1.26-1.32 (m, 24H), 1.62-1.69 (m, 2H), 2.93 (t, J=7.6 Hz, 2H), 4.05 (t, J=8.0 Hz, 2H), 4.38 (t, J=8.0 Hz, 2H) ppm; 13C NMR (100 MHz, CDCl3) δ 14.0, 22.7, 24.1, 28.6, 29.3, 29.4, 29.5, 29.6, 29.6, 31.8, 35.0, 40.3, 45.2, 153.2, 174.8 ppm; MS (ESI, m/z): 325 (M+H)+; Anal. calcd for C19H36N2O2:C, 70.32; H, 11.18; N, 8.63; O, 9.86.

4-Phenoxybenzoyl Oxazolidinone (41)

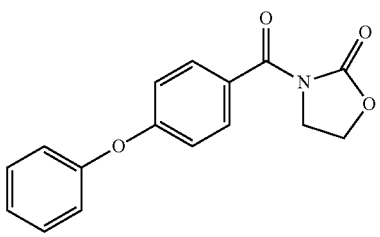 [SMILES: O=C1OCCN1C(=O)c1ccc(Oc2ccccc2)cc1]

By the general synthetic method 1 (solvent for purification: ethylacetate:petroleum ether=1:3, the acyl chloride was 4-phenoxybenzoyl chloride), the reaction was carried out to obtain product 41 (78 mg; yield: 55%, amorphous white powder).

IR (film) vmax: 2915, 2844, 1779, 1681, 1575, 1482, 1445, 1382, 1322 cm−1; 1H NMR (400 MHz, CDCl3) δ 4.17 (t, J=8.0 Hz, 2H), 4.50 (t, J=8.0 Hz, 2H), 6.97 (ddd, J=8.4, 2.8, 2.0 Hz, 2H), 7.08 (dd, J=8.4, 0.8 Hz, 2H), 7.19 (dd, J=7.6 Hz, 1H), 7.37-7.42 (ddd, J=8.4, 7.6, 2.0 Hz 2H), 7.67 (ddd, J=8.4, 2.8, 2.0 Hz, 2H) ppm; 13C NMR (100 MHz, CDCl3) δ 43.9, 62.2, 116.7, 120.3, 124.6, 126.4, 130.0, 131.7, 153.4, 155.5, 161.7, 168.9 ppm; MS (ESI, m/z): 284 (M+H)+; Anal. calcd for C16H13NO4:C, 67.84; H, 4.63; N, 4.94. Found: C, 67.75; H, 4.63; N, 4.95.

3'Chloro-4-phenoxybenzoyl Oxazolidinone (42)

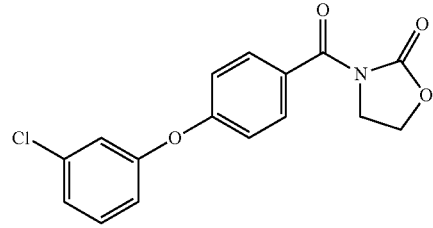

By the general synthetic method 1 (solvent for purification: ethylacetate:petroleum ether=1:3, the acyl chloride was 3'chloro-4-phenoxybenzoyl chloride), the reaction was carried out to obtain product 42 (36 mg; yield: 42%, amorphous white powder).

IR (film) vmax: 2935, 2768, 1765, 1673, 1571 cm−1; 1H NMR (400 MHz, CDCl3) δ 4.11 (t, J=8.0 Hz, 2H), 4.43 (t, J=8.0 Hz, 2H), 6.89 (d, J=72.0 Hz, 1H), 6.97 (ddd, J=8.4, 2.8, 2.0 Hz, 2H), 7.08 (dd, J=8.4, 0.8 Hz, 2H), 7.11 (dd, J=7.6, 2.0 Hz 1H), 7.47-7.50 (m, 2H) ppm; 13C NMR (100 MHz, CDCl3) δ 42.5, 60.4, 116.7, 119.7, 124.6, 126.4, 127.6, 130.3, 132.7, 136.4, 145.3, 153.4, 157.6, 161.7, 168.9 ppm; MS (ESI, m/z): 318:320 (3:1, M+H)+; Anal. calcd for C16H12ClNO4:C, 60.48; H, 3.81; Cl, 11.16; N, 4.41; O, 20.14.

3-Indolyl-n-hexanoyl Oxazolidinone (43)

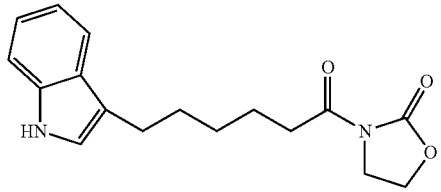

By the general synthetic method 1 (solvent for purification: ethylacetate:petroleum ether=1:2, the acyl chloride was 3-indolyl-n-hexanoyl chloride), the reaction was carried out to obtain product 43 (14 mg; yield: 27%, amorphous white powder).

1H NMR (400 MHz, CDCl3) δ1.35 (m, 2H), 1.62-1.65 (m, 4H), 2.47 (t, J=6.8 Hz, 2H), 2.92 (t, J=7.0 Hz, 2H), 4.73 (m, 2H), 7.26 (m, 2H), 7.56 (d, J=6.6 Hz, 1H), 8.30 (d, J=6.6 Hz, 1H), 8.33 (s, 1H) ppm; MS (ESI, m/z): 301 (M+H)+, C17H20N2O3.

Uracil-1-yl-n-hexanoyl Oxazolidinone (44)

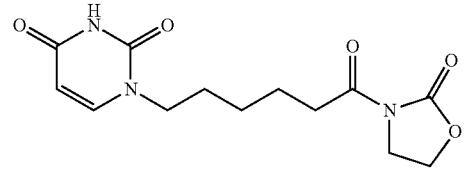

By the general synthetic method 1 (solvent for purification: ethylacetate:petroleum ether=11:1, the acyl chloride was uracil-1-yl-n-hexanoyl chloride), the reaction was carried out to obtain product 44 (18 mg; yield: 38%, amorphous white powder).

1H NMR (400 MHz, CDCl3) δ1.37 (m, 2H), 1.61-1.65 (m, 4H), 2.47 (t, J=6.8 Hz, 2H), 2.90 (t, J=7.0 Hz, 2H), 5.80 (d, J=8.4 Hz, 1H), 8.21 (d, J=8.4 Hz, 1H), 11.72 (br, 1H) ppm; MS (ESI, m/z): 296 (M+H)+, C13H17N3O5.

2-Naphthylhexanoyl Oxazolidinone (45)

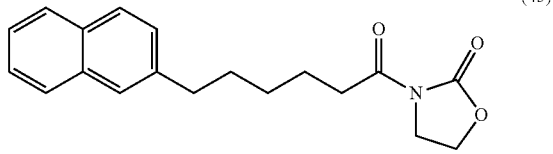

(45)

By the general synthetic method 1 (solvent for purification: ethylacetate:petroleum ether=1:5, the acyl chloride was 2-naphthylhexanoyl chloride), the reaction was carried out to obtain product 45 (27 mg; yield: 32%, amorphous white powder).

$^1$H NMR (400 MHz, CDCl3) δ1.36 (m, 2H), 1.60-1.64 (m, 4H), 2.45 (t, J=6.8 Hz, 2H), 2.91 (t, J=7.0 Hz, 2H), 7.18-7.29 (m, 7H) ppm; MS (ESI, m/z): 312 (M+H)+, C19H21NO3.

7-fluoro-2-naphthylhexanoyl Oxazolidinone (46)

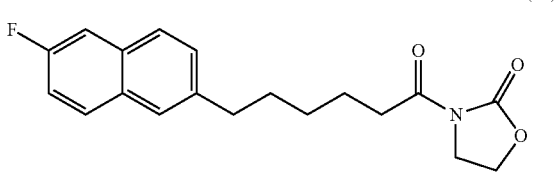

(46)

By the general synthetic method 1 (solvent for purification: ethylacetate:petroleum ether=1:4, the acyl chloride was 7-fluoro-2-naphthylhexanoyl chloride), the reaction was carried out to obtain product 46 (15 mg; yield: 26%, amorphous white powder).

$^1$H NMR (400 MHz, CDCl$_3$) δ1.36 (m, 2H), 1.60-1.64 (m, 4H), 2.47 (t, J=6.8 Hz, 2H), 2.87 (t, J=7.0 Hz, 2H), 7.20-7.31 (m, 6H) ppm; MS (ESI, m/z): 330 (M+H)$^+$, C19H20FNO3.

In Experimental examples according to the invention, compounds to be evaluated or compounds to be tested or test compounds used are the Compounds 1-46 prepared in the Examples according to the invention.

Experimental Example 1: Method for Determining Endocannabinoid Hydrolase Activity In the Experimental example, endocannabinoid hydrolases used were Fatty Acid Amide Hydrolase (FAAH) and N-acylethanolamide hydrolyzing acid amidase (NAAA), which were prepared by the method described in the document (PMCID: PMC3423427, PMC3723234, PMC2692831, PMC3382457). The preparation method was as followed: a plasmid (pCDNA3.1/NAAA or pCDNA3.1/FAAH) carrying a whole NAAA/FAAH gene was constructed, wherein the plasmid carried Cytomegalovirus (CMV) promoter and Neomycin selectable gene; the plasmid was transformed into HEK-293 cell via lipid medium, stable cell lines expressing NAAA/FAAH at a high level were obtained by G418 screening and Western-blot method. HEK-293 recombinant cells were cultured and collected, washed with PBS for 2-3 times, and ultrasonically treated in 20 mM Tris-HCl containing 0.32 M sucrose, then repeatedly frozen and thawed twice, and then centrifuged at 4° C., 800 g for 15 min. The supernatant (i.e., the desired protein) was collected, the protein concentration was determined by BCA method, and the protein was diluted to a concentration of 1 mg/mL, and sub-packaged and stored in a refrigerator at −80° C. for further use.

In the Experimental example, PBS solution used was prepared as followed: 8 g NaCl, 0.2 g KCl, 1.44 g Na$_2$HPO$_4$, and 0.24 g KH$_2$PO$_4$ were dissolved in 1 L ultrapure water, and the resultant solution was subjected to moist heat sterilization and stored at 4° C.

30 μL (1 mg/mL) endocannabinoid hydrolase was added to a sample vial, and 2 μL DMSO (Blank control group) or a different concentration of a test compound (Compounds 1-46 prepared in the Examples according to the invention) was further added. The reaction was carried out at 37° C. for 10 min. 170 μL buffer (the buffer consisted of 50 mM disodium Hydrogen Phosphate, 0.1% Triton X-100, 3 mM DTT, 150 μL) containing enzymatic hydrolysis substrate (the substrate was a heptadecenoyl ethanolamine containing a double bond and 17 carbon atoms, abbreviated as 17:1 FAE) was further added, wherein the concentration of 17:1 FAE was 5 μM. The reaction was carried out at 37° C. for 30 min, and 200 μL methanol solution containing internal standard (the internal standard was margaric acid, at a concentration of 1 nmol) was then added to stop the reaction. LC-MS was used to determine the yield of the hydrolysate 17:1 FA (i.e., a heptadecenoic acid containing a double bond) of 17:1 FAE, then a graph was plotted with Graphpad Prism 5. Thereby, the IC$_{50}$ of the test compound on endocannabinoid hydrolase was determined.

By the method above, the inhibitory effects of the Compounds 1-46 prepared in the invention on NAAA and FAAH were determined. The results were shown in Table 1, wherein $IC_{50}$ (NAAA) represents a concentration that inhibits NAAA activity to 50% of the activity prior to inhibition, $IC_{50}$ (FAAH) represents a concentration that inhibits FAAH activity to 50% of the activity prior to inhibition, and ">100 μM" represents that $IC_{50}$ of a compound on a corresponding enzyme is above 100 μM, indicating that the compound has no inhibitory effect on the enzyme.

TABLE 1

| Compound No. | Compound structure | $IC_{50}$ (NAAA) | $IC_{50}$ (FAAH) |
| --- | --- | --- | --- |
| 1 | 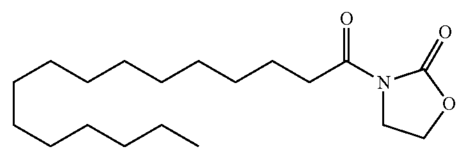 | 46.8 μM | >100 μM |
| 2 | 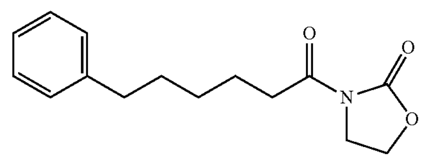 | 0.21 μM | >100 μM |
| 3 | 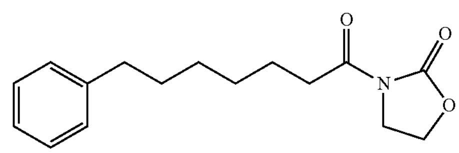 | 9.4 μM | 56 μM |
| 4 | 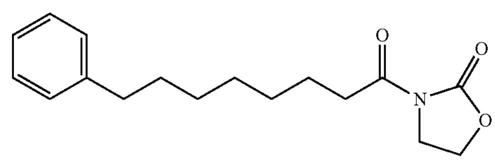 | 21 μM | 33 μM |
| 5 | 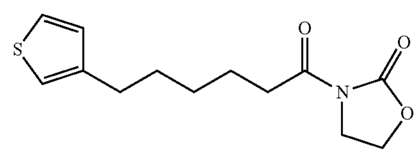 | 0.34 μM | >100 μM |
| 6 | 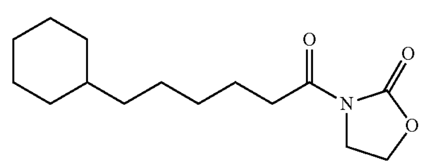 | 0.18 μM | >100 μM |
| 7 | 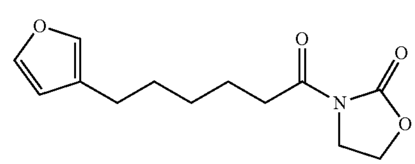 | 0.36 μM | >100 μM |
| 8 | 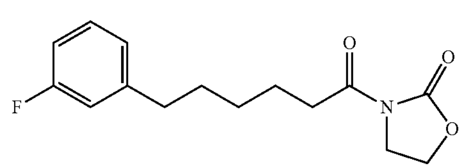 | 0.25 μM | >100 μM |

TABLE 1-continued

| Compound No. | Compound structure | IC$_{50}$ (NAAA) | IC$_{50}$ (FAAH) |
| --- | --- | --- | --- |
| 9 | 3-chlorophenyl-pentyl-oxazolidinone | 0.018 μM | >100 μM |
| 10 | 4-chlorophenyl-pentyl-oxazolidinone | 5.1 μM | >100 μM |
| 11 | 3-methylphenyl-pentyl-(4-oxopropyl)oxazolidinone | 0.38 μM | >100 μM |
| 12 | 4-methylphenyl-pentyl-(4-oxopropyl)oxazolidinone | 0.45 μM | >100 μM |
| 13 | biphenyl-3-carbonyl-oxazolidinone | 9.5 μM | 15 μM |
| 14 | biphenyl-3-acetyl-oxazolidinone | 79.2 μM | 2.8 μM |
| 15 | biphenyl-4-acetyl-oxazolidinone | 55 μM | 9.5 μM |
| 16 | 3-phenoxyphenyl-carbonyl-oxazolidinone | >100 μM | 26.7 μM |

TABLE 1-continued

| Compound No. | Compound structure | IC$_{50}$ (NAAA) | IC$_{50}$ (FAAH) |
| --- | --- | --- | --- |
| 17 | 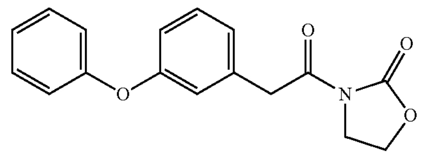 | >100 μM | 34.2 μM |
| 18 | 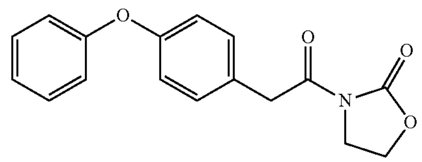 | >100 μM | 26 μM |
| 19 | 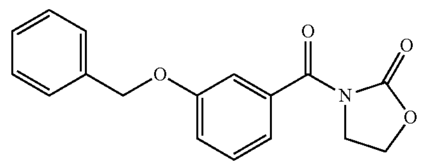 | 78.6 μM | >100 μM |
| 20 | 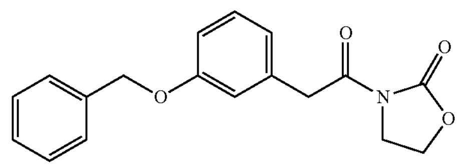 | 65.3 μM | >100 μM |
| 21 | 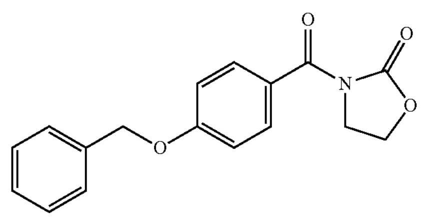 | 3.4 μM | >100 μM |
| 22 | 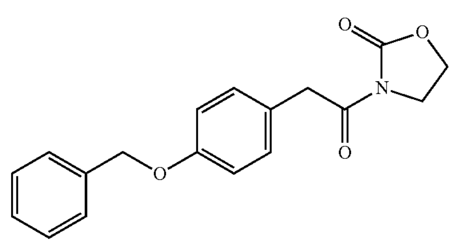 | >100 μM | 11 μM |
| 23 | 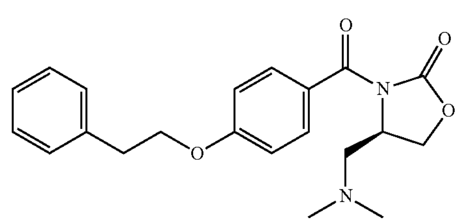 | >100 μM | 12 μM |
| 24 | 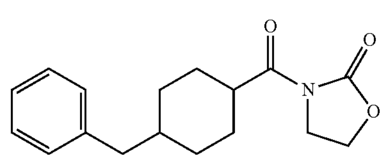 | >100 μM | >100 μM |

TABLE 1-continued

| Compound No. | Compound structure | IC$_{50}$ (NAAA) | IC$_{50}$ (FAAH) |
| --- | --- | --- | --- |
| 25 | benzyl-piperidine-4-carbonyl-oxazolidin-2-one | >100 μM | 4.2 μM |
| 26 | (pyridin-4-ylmethyl)-piperidine-4-carbonyl-oxazolidin-2-one | >100 μM | >100 μM |
| 27 | 5-phenylpentanoyl-(S)-4-methyl-oxazolidin-2-one | 0.91 μM | >100 μM |
| 28 | 5-phenylpentanoyl-5-oxo-pyrrolidine-2-carboxylic acid | >100 μM | >100 μM |
| 29 | 5-phenylpentanoyl-4-amino-pyrrolidin-2-one | >100 μM | >100 μM |
| 30 | 5-phenylpentanoyl-4-amino-pyrrolidin-2-one (other stereo) | >100 μM | >100 μM |
| 31 | 5-(4-hydroxyphenyl)pentanoyl-oxazolidin-2-one | 0.09 μM | 0.26 μM |
| 32 | 5-(3-methylphenyl)pentanoyl-oxazolidin-2-one | 0.35 μM | >100 μM |

TABLE 1-continued
| Compound No. | Compound structure | IC$_{50}$ (NAAA) | IC$_{50}$ (FAAH) |
|---|---|---|---|
| 33 | 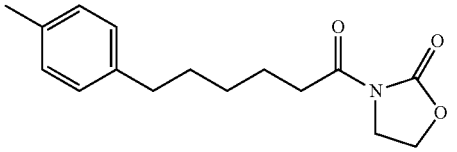 | 0.44 μM | >100 μM |
| 34 | 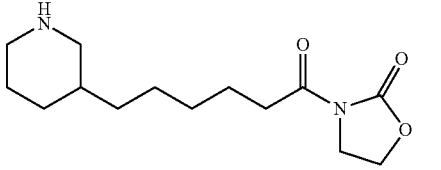 | 0.13 μM | >100 μM |
| 35 | 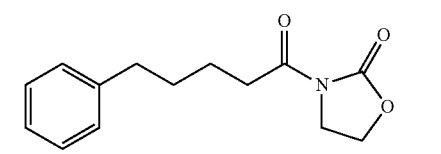 | 11.2 μM | >100 μM |
| 36 | 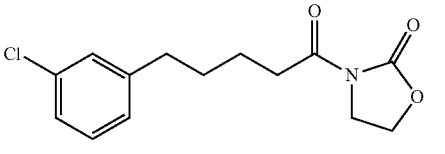 | 0.37 μM | >100 μM |
| 37 | 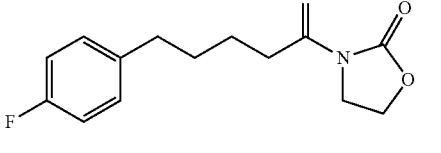 | 0.85 μM | >100 μM |
| 38 | 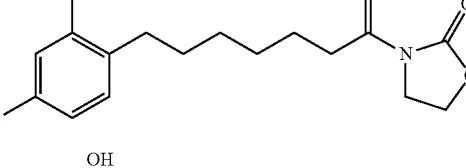 | 2.2 μM | >100 μM |
| 39 | 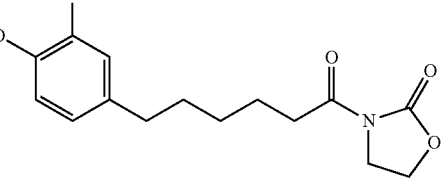 | 0.027 μM | >100 μM |
| 40 | 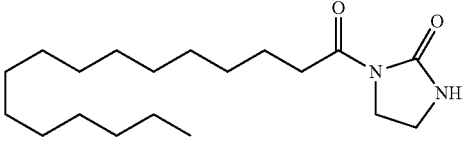 | 5.4 μM | 15.4 μM |
| 41 | 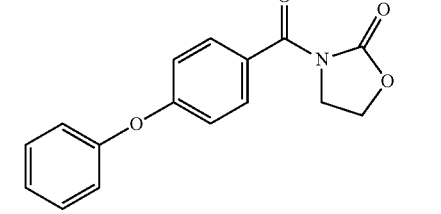 | 0.68 μM | >100 μM |

TABLE 1-continued

| Compound No. | Compound structure | IC$_{50}$ (NAAA) | IC$_{50}$ (FAAH) |
|---|---|---|---|
| 42 | 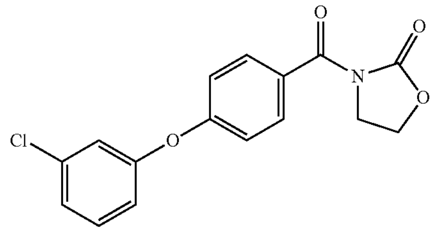 [SMILES: O=C1OCCN1C(=O)c1ccc(Oc2cccc(Cl)c2)cc1] | 0.37 μM | >100 μM |
| 43 | 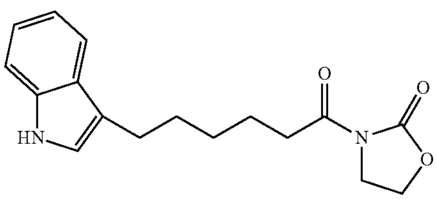 [SMILES: O=C(CCCCCc1c[nH]c2ccccc12)N1CCOC1=O] | 23.5 μM | >100 μM |
| 44 | 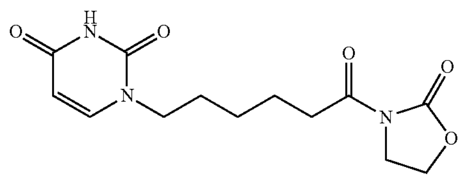 [SMILES: O=C(CCCCCn1ccc(=O)[nH]c1=O)N1CCOC1=O] | 15.8 μM | >100 μM |
| 45 | 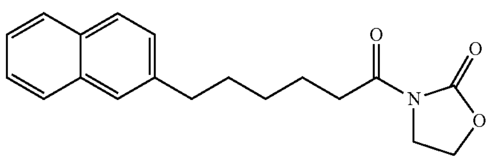 [SMILES: O=C(CCCCCc1ccc2ccccc2c1)N1CCOC1=O] | 0.92 μM | >100 μM |
| 46 | 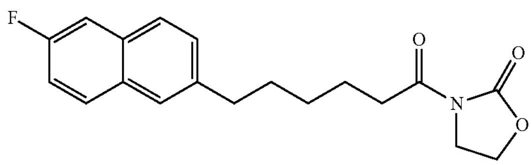 [SMILES: O=C(CCCCCc1ccc2cc(F)ccc2c1)N1CCOC1=O] | 5.7 μM | >100 μM |

Experimental Example 2: Pain Assays

In the Experimental example, compounds to be evaluated or compounds to be tested or test compounds used are the Compounds 1-46 prepared in the Examples according to the invention. In the Experimental example, all the agents for injection, including compounds to be evaluated or compounds to be tested or test compounds, and positive control drug, were dissolved in a mixed solvent of PEG400:Tween 80:normal saline (at a volume ratio of 5:5:90), at a concentration of 5 mg/mL.

1. Experimental Example of Neuropathic Pain

Neuropathic pain mouse model induced by spared nerve injury (SNI) is a common animal model for studying neuropathic pain medically. The invention uses the model to evaluate the therapeutic effects of the compounds on neuropathic pain, wherein the model can represent peripheral neuropathic pain including, but not limited to post-herpetic neuralgia, pain caused by diabetic perineuropathy, neurothlipsis and exudation caused by tumor, lumbar surgery failure syndrome, neuropathic pain caused by lumbar disc protrusion, postpartum neuralgia, trigeminal neuralgia, chemotherapy-induced multiple neuropathic pain, post-radiotherapy plexopathy, and radicular neuralgia.

C57BL/6 mice (purchased from Shanghai SLAC Laboratory Animal Co., Ltd) were anesthetized by intraperitoneal injection with pentobarbital sodium (40 mg/kg), and skin from knee joint to gluteal region was subjected to skin preparation and disinfection. After the mice were fixed, the knee joint part was cut about 1 cm longitudinally with bistoury, and muscle tissues were separated by blunt dissection to expose sciatic nerve. The tibial and common peroneal nerve branches of sciatic nerve stem were cut off carefully, and the cut was then stitched up. The mice was placed in a clean observation cage. In the sham-operation group, only sciatic nerve was exposed without cutting the tibial and common peroneal nerve branches. From the day before the experiment to 24 h after the operation, the plantar edges of the mice were stimulated everyday by Plantar Analgesia Meter for Thermal Paw (Ugo Basile Company (Italy), Product ID: 37450), and data was collected automatically to obtain the threshold value of mice to mechanical stimulation. The compound to be evaluated (10 mg/kg) was administered via intraperitoneal injection at 1 h before the test. The positive control drug gabapentin was administered at a dose of 100 mg/kg. All the agents to be injected were dissolved in a mixed solvent of PEG400:Tween 80:normal saline (at a volume ratio of 5:5:90), at a concentration of 5 mg/mL. By comparing the threshold values (the acting force of when the mouse retracting the paw) at different administration time in different administration groups, the compound was evaluated for its analgesic effect on neuropathic pain.

Figure 2:
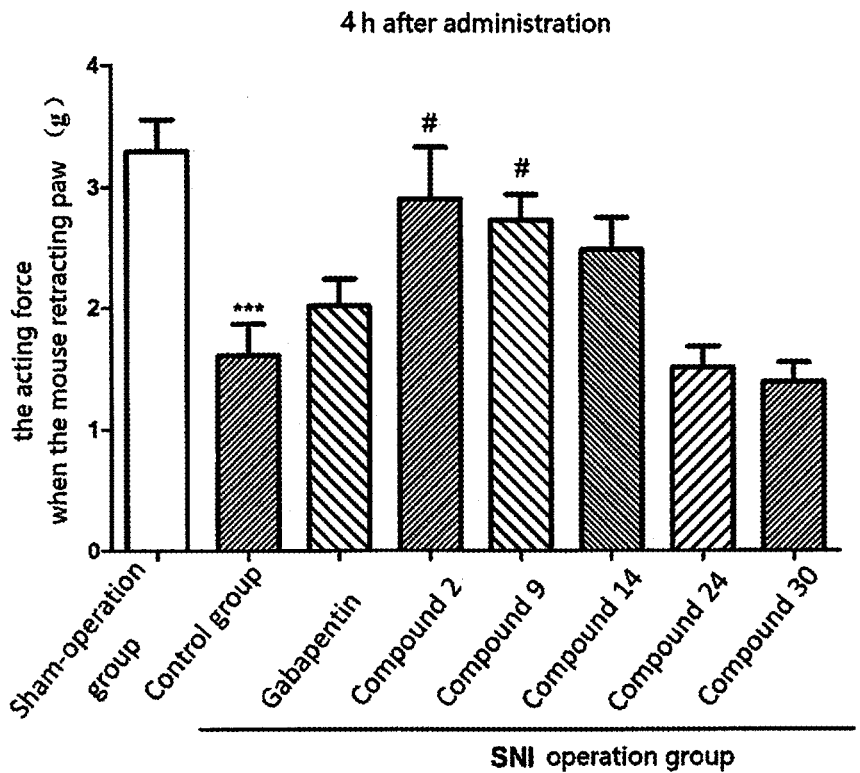
FIG. 2 illustrates the effects of Compounds 2, 9, 14, 24, 30 and the positive control drug gabapentin on SNI neuropathic pain at 4 h after administration.
Figure 3:
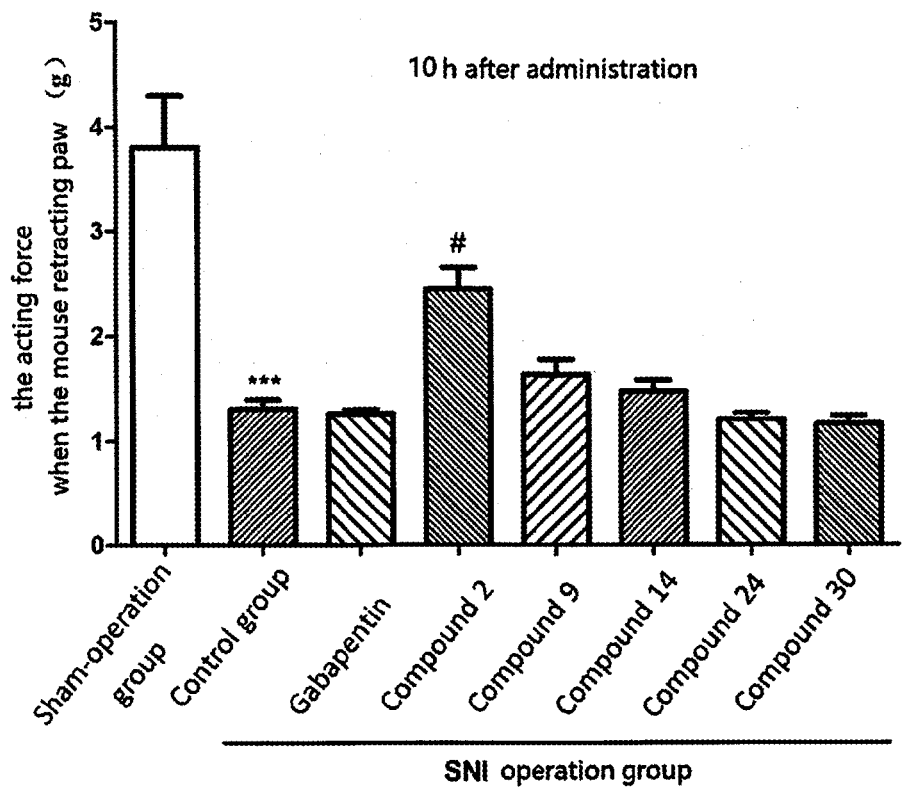
FIG. 3 illustrates the effects of Compounds 2, 9, 14, 24, 30 and the positive control drug gabapentin on SNI neuropathic pain at 10 h after administration.

By the method above, the compounds to be evaluated were determined for their analgesic effects in SNI models, and the results were shown in FIGS. 1-3. As seen from FIGS. 1 and 2, Compounds 2, 9, and 14 exhibited significant effects of inhibiting central neuropathic pain, while Compounds 24 and 30 did not exhibit any effect of inhibiting central neuropathic pain. Compared to the positive control drug gabapentin, Compounds 2, 9, and 14 were not as effective as the control drug at 1 h after administration, but retained a relatively strong effect of inhibiting central neuropathic pain at 4 h after administration. However, the effect of the control drug gabapentin disappeared gradually. As shown in FIG. 3, Compound 2 still had a sustained analgesic effect at 10 h after administration, i.e., had an action period much longer than that of the control drug.

2. Experimental Example of Abdominal Inflammatory Pain

Typical model for studying inflammation-induced visceral pain medically was used to evaluate the therapeutic effects of compounds on inflammatory visceral pain. The model can represent general visceral pain including, but not only limited to appendicitis, gastritis, pancreatitis, prostatitis, myocarditis, interstitial cystitis, pain caused by hepatic, gall or kidney stone, irritable bowel syndrome, and chronic pelvic pain syndrome.

Experimental Kunming mice (purchased by Xiamen University Laboratory Animal Center from Shanghai SLAC Laboratory Animal Co., Ltd) were in an experimental environment with free access to food and water for 1 week. The mice were fasted for 24 h before administration. The compound to be evaluated (10 mg/kg) was administered to the mice by intraperitoneal injection at 1 h before administration of acetic acid, wherein the positive control drug indometacin was administered at a dose of 20 mg/kg, and the blank control was normal saline. Acetic acid (50 µL, acetic acid dissolved in normal saline, at a concentration of 5%) was administered to the mice by intraperitoneal injection, and the mice were then placed in the observation cage. A video camera was used to record the behavior of the mice in the following 20 min. Pain-related behavior was analyzed statistically based on torsion times of the mice in said period.

Figure 4:
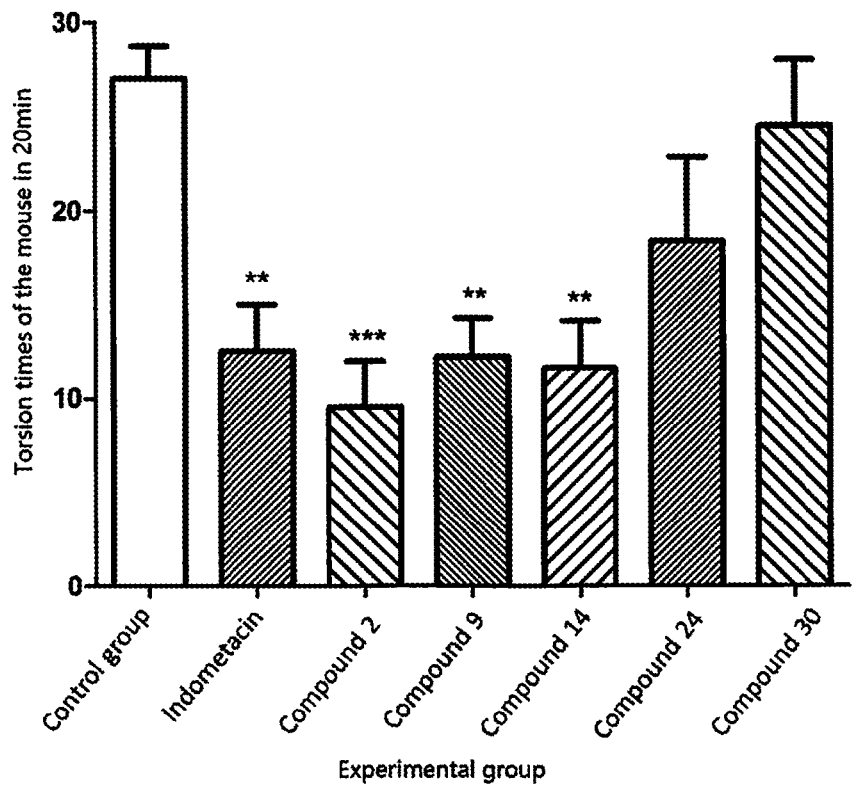
FIG. 4 illustrates the effects of Compounds 2, 9, 14, 24, 30 and the positive control drug indometacin on inflammatory abdominal pain caused by acetic acid.

As seen in FIG. 4, Compounds 2, 9, and 14 all exhibited significant effects of inhibiting abdominal inflammatory pain, while Compounds 24 and 30 did not exhibit any effect of inhibiting abdominal inflammatory pain. Compared to the positive control drug indometacin, a half dose of the effective compound of the invention can achieve the same effect as indometacin.

3. Experimental Example of Headache

Nitroglycerin-induced headache rat model was a common model for studying inflammatory pain medically. The model was used in the invention to evaluate the therapeutic effects of the compounds on headache. The model can represent mixed pain including, but not only limited to: migraine, cluster headache, tension headache syndrome, prosopodynia, lumbodynia, shoulder pain, burning mouth syndrome, and complex regional pain syndrome.

Experimental Wistar rats with a body weight of about 250 g for each (purchased from Shanghai SLAC Laboratory Animal Co., Ltd) were in an experimental environment with free access to food and water for 1 week. The rats were fasted for 24 h before administration. The compound to be evaluated (10 mg/kg) was intraperitoneally injected to the rat at 1 h before the administration of nitroglycerin, wherein the positive control drug was indomethacin and the blank control was normal saline. Nitroglycerin (10 mg/kg, nitroglycerin dissolved in normal saline, at a concentration of 5%) was injected at epidermis of the rat neck, and the rats were then placed in the observation cage. A video camera was used to record the behavior of the rats in the following 60 min. Pain-related behavior was analyzed statistically based on the times that the rat scratched its head in said period.

Figure 5:
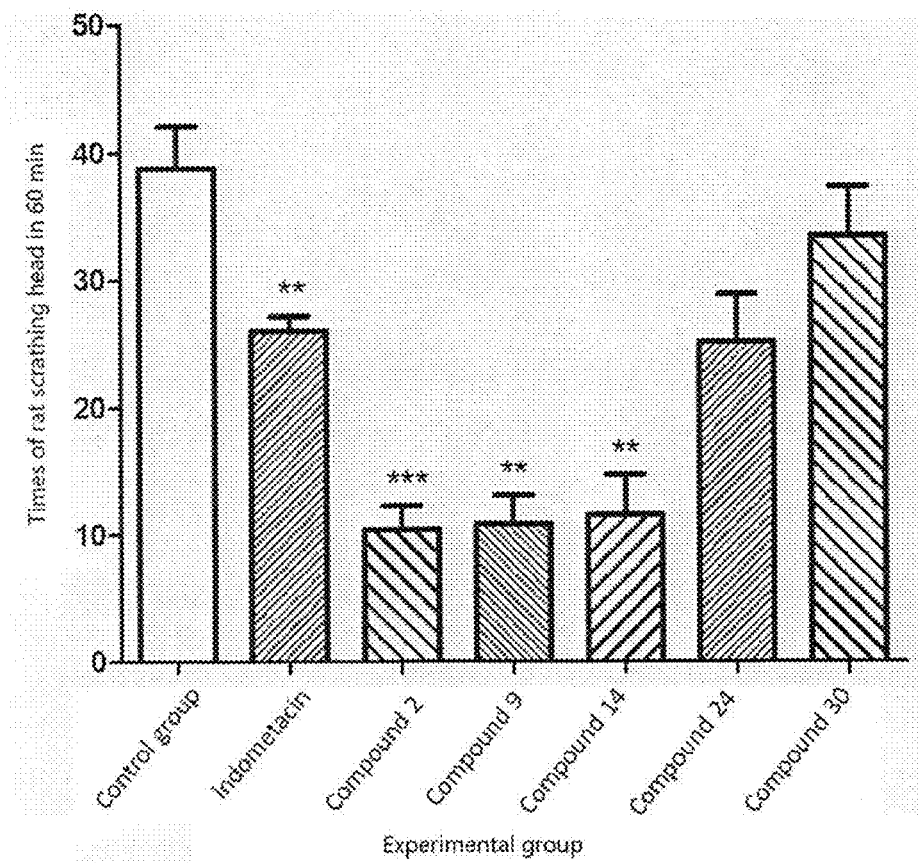
FIG. 5 illustrates the effects of Compounds 2, 9, 14, 24, 30 and the positive control drug indometacin on headache caused by nitroglycerin in rats.

By the method above, the tested Compound 2, 9 and 14 exhibited significant effects of inhibiting nitroglycerin-induced headache in rats, while Compounds 24 and 30 did not exhibit any effect of inhibiting headache in rats (see FIG. 5). The effective compounds of the invention had better effects than the positive control drug indometacin.

4. Experimental Example of Adjuvant-Induced Osteoarthritis Pain

Typical model for studying inflammatory pain medically was used to evaluate the therapeutic effects of compounds on inflammatory pain. 0.1 mL Freund's complete adjuvant was intradermally injected to toe of the left hind foot of the rats in each group to obtain adjuvant-induced arthritis rat models. Foot volume method was used to measure primary and secondary foot swelling degree (swelling degree=volume after inflammation−volume before inflammation), and polyarticular arthritis were scored (5 scoring grades: 0 represents no red swelling; 4 represents red swelling at all the paws including anklebone. The scores are accumulated according to the lesion degree of the rest three limbs not injected with adjuvant, and the highest score is 12). Before inflammation and at 6 h, 12 h, 18 h and 24 h after inflammation, Paw Volume Meter was used to measure the foot volume at the inflammatory side, and the swelling degree was calculated. The model can represent inflammatory pain including, but not only limited to: osteoarthritis pain and fibromyalgia syndrome, inflammatory pain of rheumatic and rheumatoid arthritis, inflammatory pain of endometriosis, inflammatory toothache, ankylosing spondylitis pain, and gouty arthritis pain.

By the method above, the tested Compound 2, 9, and 14 (10 mg/Kg) exhibited significant effects of inhibiting osteoarthritis pain, and the effective compounds of the invention had better effects than the positive control drug indometacin (10 mg/Kg).

Comparison of primary foot swelling degree of rats in each of the groups were shown in Table 2.

TABLE 2

| Group | Foot swelling degree after inflammation (X ± S, n = 10, mL) | | | |
|---|---|---|---|---|
| | 6 h | 12 h | 18 h | 24 h |
| Normal control Group | 0.08 ± 0.01 | 0.07 ± 0.03 | 0.08 ± 0.02 | 0.08 ± 0.03 |
| Adjuvant-induced arthritis model group | 0.98 ± 0.14$^a$ | 1.78 ± 0.21$^a$ | 1.95 ± 0.13$^a$ | 1.87 ± 0.16$^a$ |
| indometacin | 0.57 ± 0.16$^c$ | 0.96 ± 0.21$^c$ | 1.32 ± 0.22$^b$ | 1.08 ± 0.26$^c$ |
| Compound 2 | 0.35 ± 0.07$^c$ | 0.65 ± 0.13$^c$ | 1.06 ± 0.14$^c$ | 0.89 ± 0.21$^c$ |
| Compound 9 | 0.44 ± 0.09$^c$ | 0.75 ± 0.24$^c$ | 1.24 ± 0.24$^b$ | 1.06 ± 0.18$^c$ |
| Compound 14 | 0.75 ± 0.11$^c$ | 1.06 ± 0.19$^c$ | 1.43 ± 0.25$^b$ | 1.36 ± 0.18$^b$ |

Note:
Compared to control group,
$^a$P < 0.01; compared to adjuvant-induced arthritis model group,
$^b$P < 0.05;
$^c$P < 0.01.

Experimental Example 3: Stability Assay

In the Experimental example, PBS solution used was prepared by the following method: 8 g NaCl, 0.2 g KCl, 1.44 g Na$_2$HPO$_4$, and 0.24 g KH$_2$PO$_4$ were dissolved in 1 L ultrapure water, subjected to moist heat sterilization, and stored at 4° C.

1. Stability Assay in Rat Plasma

To each of several tubes sub-packaged with rat plasma, PBS solution was added in a volume equal to a quarter of plasma volume, and the resultant mixture was mixed well. To 1.5 mL diluted rat plasma, the compound to be tested (Compound 2, 8, 9, 11, 31, and 41) was added until the compound was at a final concentration of 2 μM, and the plasma sample containing the compound was incubated in a 37° C. incubator. At different time points (0, 10, 30, 60, 120, 240, 360, 720, 1440 min), 50 μL plasma sample was taken and added to 150 μL precooled methanol (containing the internal standard compound E8, with a structure of

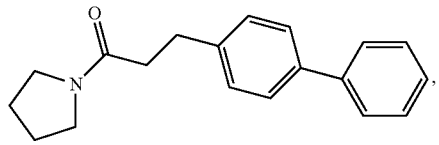 [SMILES: O=C(CCc1ccc(-c2ccccc2)cc1)N1CCCC1]

and a name of 1-(2-Biphenyl-4-yl)ethyl-carbonyl pyrrolidine, 1 nmol/sample), wherein three parallel samples were prepared for each time point. The samples were then vertically mixed well, and centrifuged at 4° C., 12000 g for 10 min. The supernatant was transferred to a sample vial. LC-MS/MS was used to measure the peak area at different time points, Analyst® version 1.4.1. software was used to analyze chromatographic peak, and the content of the target compound was calculated by virtue of the standard curve.

2. Stability Assays at Acidic and Basic Conditions

To the prepared PBS, adjusted with dilute hydrochloric acid to pH 5.0, or adjusted with saturated NaOH to pH=7.4, the compound to be tested (Compound 2, 8, 9, 11, 31, and 41) was added until the compound to be tested was at a final concentration of 1 μM. The sample containing the compound to be tested was then incubated in a constant temperature shaker at 37° C. At different time points (0 min, 10 min, 30 min, 1 h, 2 h, 4 h, 6 h, 12 h, 24 h), 50 μL sample was taken and added to 150 μL precooled methanol (containing the internal standard E8, 1 nmol/sample), wherein three parallel samples were prepared for each time point. The samples were then vertically mixed well, and transferred to a sample vial. LC-MS/MS was used to measure the peak area at different time points, Analyst® version 1.4.1. software was used to analyze chromatographic peak, and the content of the target compound was calculated based on the standard curve.

As seen from Table 3, the effective compounds of the invention had a half-life of more than 24 h at acidic or basic conditions, and a half-life of more than 120 min in rat plasma, i.e., their stability was much higher than the reported β-lactam type NAAA inhibitor (β-lactam type NAAA inhibitor had a half-life of less than 15 min in rat plasma).

3. Assay on Drug Metabolism in Rat

50 SD rats (purchased from Shanghai SLAC Laboratory Animal Co., Ltd) were divided into 5 groups randomly, 10 rats per group. After anesthesia with ether, rat was fixed on the operating table on its back, and was shaved at the operative site of neck. After disinfection with 75% alcohol, the neck was cut about 1.5 cm longitudinally, muscle tissues and nervi vascularis surrounding trachea were separated by blunt dissection, and carotid artery was separated by blunt dissection. Ligation was performed at distal end, an artery clamp was used at proximal part, and the distance between them was about 1 cm. A small cut was made with a pair of ophthalmic scissors at proximal part close to the ligated site, and arterial duct was introduced from the small cut to the proximal part, the artery clamp was loosened, the arterial ostium was clamped with smooth forceps, whilst the arterial duct was delivered to heart ventricle. Upon the introduction of the arterial duct into heart ventricle, the blood vessel was ligated. By using the same intubation method for artery, intubation was applied to jugular veins. After intubation, a tubule filled with heparin sodium was drawn out from artery and vein, which passed through the skin under the ear of the rat and drawn out from the dorsal part skin of the neck of the rat, and the tubule was fixed well. The muscles and skin were sutured at the surgical site of the rat, and normal saline containing heparin sodium was injected from time to time via the tubule connecting the artery and the vein to prevent tubule obstruction due to blood coagulation. The rat was placed in a warm and clean cage provided with water and food, waiting for the rat to wake up naturally.

After the rat regained consciousness and acted normally, assay on metabolic stability of compounds was performed in the rat. All the agents to be injected (including compounds to be tested and control drug) were dissolved in a mixed solvent of PEG400:Tween 80:normal saline (at a volume ratio of 5:5:90), at a concentration of 5 mg/mL. The agent was injected slowly at a dose of 30 mg/Kg via the tubule drawn out from the jugular vein. After administration, the time was recorded, and blood was collected from the tubule drawn out from carotid artery at 2, 5, 10, 20, 30, 60, 240, 360, and 720 min, in an amount of 200 μL for each time. The whole blood was placed in commercially available heparin sodium blood-collecting tube (Jiangxi Jingzhi Medical Equipment Co., Ltd.), centrifuged at 1800 g for 15 min. To the supernatant plasma, 150 μL pre-cooled methanol stopping buffer (containing internal standard E8, 1 nmol/sample) was added, vertically mixed well, and then centrifuged at 4° C., 12000 g for 10 min. The supernatant was transferred to a sample vial, the target compound was detected by LC-MS/MS, and the content of the compound was calculated by virtue of standard curve.

As seen from Table 3, the effective compounds of the invention had a half-life of 60-300 min in rat, i.e., their stability was much higher than the reported β-lactam type NAAA inhibitor (β-lactam type NAAA inhibitor had a half-life of less than 5 min in rat).

TABLE 3

| | Half-life (min) | | | |
|---|---|---|---|---|
| Compound | pH 5.0 | pH 7.4 | Rat plasma | Metabolism in rat |
| 2 | >1440(100) | >1440(100) | 188 | 144 |
| 8 | >1440(100) | >1440(100) | 165 | 93 |
| 9 | >1440(80) | >1440(100) | 163 | 117 |
| 11 | >1440(100) | >1440(100) | 267 | 184 |
| 31 | >1440(92) | >1440(100) | 132 | 74 |
| 41 | >1440(100) | >1440(100) | 320 | 175 |

Experimental Example 4: Assay on Cytotoxicity

In the Experimental example, PBS solution used was prepared by the following method: 8 g NaCl, 0.2 g KCl, 1.44 g $Na_2HPO_4$, 0.24 g $KH_2PO_4$ were dissolved in 1 L ultrapure water, subjected to moist heat sterilization, and stored at 4° C.

RAW264.7 cells in good growing state (purchased from American Type Culture Collection, ATCC, Beijing), at a density of about 80%-90%, were scraped off with a cell scraper to prepare a cell suspension. After counting, the cells were accurately seeded in a 96-well plate, at 100 μL per well, wherein the total number of cells retained the same, at about 20000 cells/well, and the same amount of culture medium (which was DMEM (Gibco, Shanghai) medium containing 10% fetal bovine serum (PAA), 1% penicillin-streptomycin (PAA)) was added. The 96-well plate was placed in an incubator to preincubate for 24 h (37° C., 5% $CO_2$). The marginal wells of the plate were filled with an equal amount of PBS, but were not seeded with cells, so as to prevent evaporation of the culture medium in the experimental group. The old medium was removed with a pipette at 12 h after plating cells, 100 μL compound 2, 9 at a different concentration (at a concentration of 3, 10, 30, 100 μM, respectively) diluted with culture medium was added to the plate, and an equal amount of DMSO was added as control in control group, and three wells in parallel were used for each concentration. After incubating the plate in the incubator for a period of time (24 or 48 h), 10 μL CCK8 solution was added to each well, and then the plate was incubated in incubator for 1.5 h. the absorbance OD value was determined at 450 nm by microplate reader, and the OD value was proportional to the number of living cells. The cell survival rate was obtained by comparing the OD value in each group with the OD value in blank group. Cell viability× 100%=[OD value (Administration group)–OD value (Blank group)]/[OD value (Control group)–OD value (Blank group)]×100%.

Figure 6A:
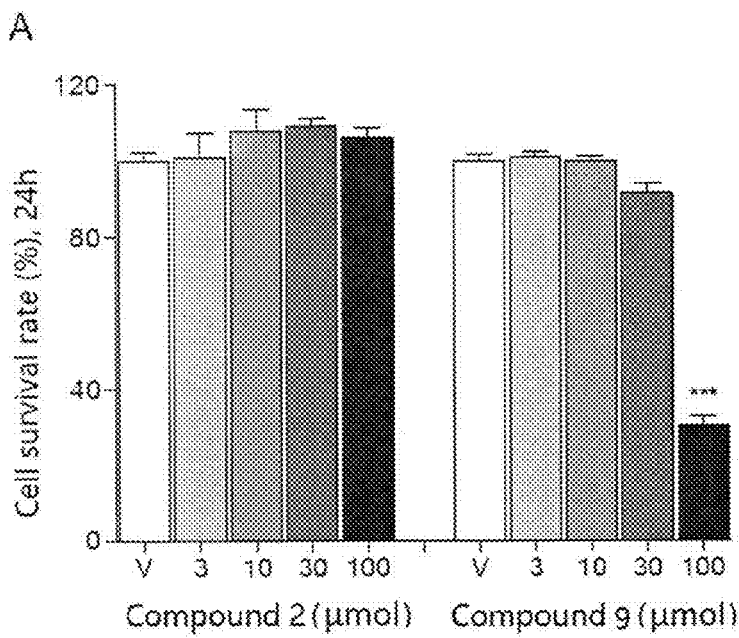
FIG. 6A illustrates the effects of compounds 2 and 9 at different concentrations on cell vitality after incubation with RAW264.7 cells for 24 h.
Figure 6B:
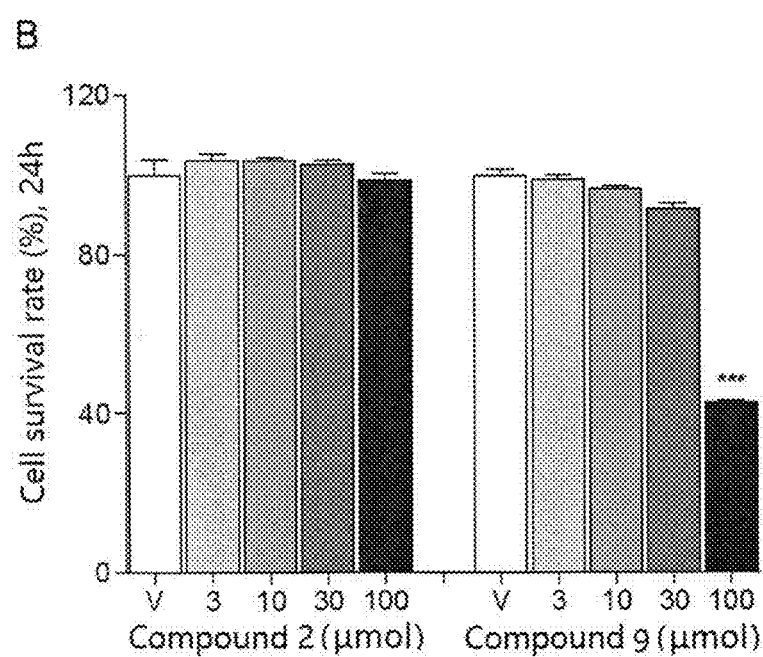
FIG. 6B illustrates the effects of compounds 2 and 9 at different concentrations on cell vitality after incubation with RAW264.7 cells for 48 h.

The experimental results showed that except for compound 9 at a high concentration of 100 μM, compound 2, 9 at other different concentrations had no effect on cell viability after incubation with cells for 24 h (see FIG. 6A) and 48 h (see FIG. 6B).

Experimental Example 5: Assay on Toxicity to Early Development of Zebrafish Embryos Fertilized eggs (donated by Zebrafish Research Group, School of Life Sciences, Xiamen University) were incubated in freshly prepared zebrafish embryo culture medium, which was replaced by fresh culture medium every day, and cultured in 28.5° C. incubator. Pure water was placed in the incubator to ensure a certain humidity in the culture environment. The formulation for zebrafish embryo culture medium was following: 5 mM NaCl, 0.17 mM KCl, 0.33 mM $CaCl_2$, 0.33 mM $MgSO_4$, 10-5% methylene blue. The culture medium was prepared with pure water. For example, NaCl: 292.2 mg, KCl: 12.68 mg, $CaCl_2$: 36.63 mg, $MgSO_4$: 39.72 mg, and methylene blue: 0.1 μL were needed for the preparation of 1 L culture medium.

7 Groups were set for each test compound, including 5 experimental groups relating to the test compound at different concentrations (solutions containing the test compound at different concentrations were prepared by using zebrafish embryo culture medium, wherein the concentrations were 10 mg/L, 3 mg/L, 1 mg/L, 0.3 mg/L, 0.1 mg/L), 1 solvent control group (DMSO) and 1 blank control group. The positive control drug was OTC analgesic ibuprofen at concentrations as described above. A 96-well cell culture plate was used to perform the experiment, three wells in parallel were used for each experimental group, and 10 fish eggs were contained in each well.

Culture medium containing a test compound was prepared, and the culture medium was added to a 96-well plate in advance, and each fertilized egg (by reference to the experimental method in OECD No. 212 document, fertilized eggs, which developed normally within 2 h after fertilization, were selected and subjected to exposure. Transparent fish eggs visible to naked eye were normally fertilized, while white fish eggs were dead and discarded. After the selection, the normally fertilized eggs had begun to divide as observed under microscope) was then independently placed in a different well, and cultured in the culture medium containing a test compound at a different concentration. Embryo development status at different stages was observed and photographed with invert microscope, including:

I. Morphological observation: the developmental states of fertilized eggs (yolk being coagulated or not, eye spot, pericardial sac being edematous or not, bloodstream being existing or not, tail development status, and the like) were observed and photographed at 2 h, 4 h, 8 h, 12 h, 24 h, 48 h, 72 h, and 96 h;

II. Hatching number and death number were counted at 72 h after fertilization, and hatching rate and mortality were calculated;

III. Body length of the hatched young fishes at 72 h was measured (measured after photographing with invert microscope);

IV. Embryonic abnormalities after 72 h (manifestations of abnormalities: no formation of melanin, yolk sac disease, campylorrhachia, eye defect, tail defect, reduced heart rate, reduced hatching rate, etc.)

V. Heartbeat of young fishes (times/min) was recorded at 72 h and 96 h after fertilization (Recording method: heartbeat of young fishes could be clearly observed under microscope, and the number of heartbeats was recorded for 30 s).

Experimental results showed that at a concentration of 1 mg/L, the hatching rate for the group of Compound 2 and the group of Compound 9 reached up to 96.67% and 90% at 72 h, respectively, while the hatching rate for the ibuprofen group was only 56.67%; at concentrations of 0.3 mg/L and 0.1 mg/L, the hatching rate for the groups of Compound 2 and Compound 9 was significantly higher than that of the ibuprofen group at 72 h, while the mortality was much lower than that of the ibuprofen group (see Table 4). The research results above showed that at a dose lower than 3 mg/L, the toxicity of Compound 2 and Compound 9 on zebrafish embryo development was significantly lower than that of ibuprofen.

independently placed in a different well, and cultured in the culture medium containing a test compound at a different concentration. Embryo development status at different stages were observed and photographed with invert microscope, including:

I. Morphological observation: the developmental states of fertilized eggs (yolk being coagulated or not, eye spot, pericardial sac being edematous or not, bloodstream being existing or not, tail development status, and the like) were observed and photographed at 48 h, 72 h, and 96 h;

II. Hatching number and death number were counted at 72 h after fertilization, and hatching rate and mortality were calculated;

III. Body length of the hatched young fishes at 72 h was measured (measured after photographing with invert microscope);

TABLE 4

The effects of compound 2, 9 and ibuprofen on zebrafish with respect to parameters such as hatch, heartbeat, and body length

| Group | Death number (72 h) Compound | | | Unhatching number (72 h) Compound | | | Hatching number (72 h) Compound | | |
|---|---|---|---|---|---|---|---|---|---|
| (n = 30) | 2 | 9 | ibuprofen | 2 | 9 | ibuprofen | 2 | 9 | ibuprofen |
| Blank | 1 | 0 | 4 | 0 | 0 | 0 | 29 | 30 | 26 |
| Control | 0 | 0 | 4 | 0 | 0 | 0 | 30 | 30 | 26 |
| 0.1 mg/L | 3 | 2 | 8 | 0 | 0 | 0 | 27 | 28 | 22 |
| 0.3 mg/L | 2 | 2 | 8 | 0 | 0 | 2 | 28 | 28 | 20 |
| 1 mg/L | 1 | 3 | 13 | 0 | 0 | 0 | 29 | 27 | 17 |
| 3 mg/L | 30 | 30 | 28 | 0 | 0 | 2 | 0 | 0 | 0 |
| 10 mg/L | 30 | 30 | 30 | 0 | 0 | 0 | 0 | 0 | 0 |

| Group | Body length (mm, 72 h) Compound | | | Heartbeat (per min, 72 h) Compound | | |
|---|---|---|---|---|---|---|
| (n = 30) | 2 | 9 | ibuprofen | 2 | 9 | ibuprofen |
| Blank | 3.83 ± 0.02 | 3.87 ± 0.03 | 3.90 ± 0.06 | 124 ± 2.61 | 125 ± 1.23 | 124 ± 2.61 |
| Control | 3.90 ± 0.08 | 3.86 ± 0.02 | 3.98 ± 0.06 | 125 ± 1.10 | 126 ± 2.54 | 125 ± 2.74 |
| 0.1 mg/L | 3.86 ± 0.05 | 3.90 ± 0.05 | 3.94 ± 0.14 | 130 ± 3.00 | 129 ± 2.73 | 125 ± 2.40 |
| 0.3 mg/L | 3.87 ± 0.05 | 3.86 ± 0.03 | 3.95 ± 0.09 | 130 ± 3.58 | 130 ± 3.22 | 125 ± 2.48 |
| 1 mg/L | 3.85 ± 0.06 | 3.88 ± 0.04 | 3.77 ± 0.18 | 128 ± 3.29 | 130 ± 2.76 | 126 ± 2.56 |
| 3 mg/L | — | — | — | — | — | — |
| 10 mg/L | — | — | — | — | — | — |

Experimental Example 6: Assay on Short-Term Acute Toxicity to Development of Zebrafish Embryos By the same method described above, zebrafish fertilized eggs were cultured. 7 Groups were set for each test compound, including 5 experimental groups relating to the test compound at different concentrations (solutions containing the test compound at different concentrations were prepared by using zebrafish embryo culture medium, wherein the concentrations were 100 mg/L, 10 mg/L, 1 mg/L, 0.1 mg/L, 0.01 mg/L), 1 solvent control group (DMSO) and 1 blank control group. The fertilized eggs were placed and cultured in a 28.5° C. incubator, a certain humidity was ensured in the culture environment. Culture medium containing a test compound was prepared, and the culture medium was added to a 96-well plate in advance, and each fertilized egg (by reference to the experimental method in OECD No. 212 document, fertilized eggs, which developed normally within 24 h after fertilization, were selected and subjected to exposure. Transparent fish eggs visible to naked eye were normally fertilized, while white fish eggs were dead and discarded. After the selection, the normally fertilized eggs had begun to divide as observed under microscope) was then IV. Embryonic abnormalities after 72 h (manifestations of abnormalities: no formation of melanin, Yolk Sac disease, campylorrhachia, eye defect, tail defect, reduced heart rate, reduced hatching rate, etc.)

V. Heartbeat of young fishes (times/min) was recorded at 72 h and 96 h after fertilization (Recording method: heartbeat of young fishes could be clearly observed under microscope, and the number of heartbeats was recorded for 30 s).

The experimental results showed that in the solvent control group and the blank group, zebrafish developed normally. Zebrafish embryos exposed to 10 mg/L ibuprofen had a hatching rate of 0 and a mortality of 100% at 72 h, and in the ibuprofen group, the hatching rate decreased with the increase of dose at 72 h; at the same dose, the hatching rate of zebrafish embryos for compound 2 and compound 9 was 93.3%, and compound 2 and compound 9 had little effect on the hatching rate at a dose lower than 10 mg/L (See Table 5). Only when the F96 concentration was above 10 mg/L, it had a significant effect on hatching rate and mortality of zebrafish embryos at 72 h; while ibuprofen had an effect on hatching rate of zebrafish at 72 h even at a low concentration of 0.01 mg/L, and reduced the hatching rate of zebrafish by about half at 1 mg/L, and the effect was more significant with the increase of the concentration of ibuprofen.

TABLE 5

The effects of compound 2, 9 and ibuprofen on zebrafish with respect to parameters such as hatch, heartbeat, and body length

| Group | Death number (72 h) Compound | | | Unhatching number (72 h) Compound | | | Hatching number (72 h) Compound | | |
|---|---|---|---|---|---|---|---|---|---|
| (n = 30) | 2 | 9 | ibuprofen | 2 | 9 | ibuprofen | 2 | 9 | ibuprofen |
| Blank | 0 | 0 | 0 | 0 | 0 | 0 | 30 | 30 | 30 |
| Control | 0 | 0 | 0 | 0 | 0 | 0 | 30 | 30 | 30 |
| 0.01 mg/L | 0 | 0 | 0 | 0 | 0 | 5 | 30 | 30 | 25 |
| 0.1 mg/L | 0 | 0 | 0 | 0 | 0 | 8 | 30 | 30 | 22 |
| 1 mg/L | 0 | 0 | 2 | 0 | 0 | 11 | 30 | 30 | 17 |
| 10 mg/L | 0 | 0 | 30 | 2 | 2 | 0 | 28 | 28 | 0 |
| 100 mg/L | 30 | 30 | 30 | 30 | 30 | 0 | 0 | 0 | 0 |

| Group | Body length (mm, 72 h) Compound | | | Heartbeat (per min, 72 h) Compound | | |
|---|---|---|---|---|---|---|
| (n = 30) | 2 | 9 | ibuprofen | 2 | 9 | ibuprofen |
| Blank | 4.01 ± 0.51 | 4.02 ± 0.42 | 3.94 ± 0.15 | 126 ± 1.41 | 125 ± 0.76 | 125 ± 1.60 |
| Control | 4.02 ± 0.01 | 4.02 ± 0.17 | 3.94 ± 0.08 | 124 ± 0.89 | 124 ± 1.42 | 125 ± 1.97 |
| 0.01 mg/L | 3.90 ± 0.93 | 4.01 ± 0.24 | 3.97 ± 0.06 | 124 ± 1.67 | 124 ± 0.27 | 125 ± 2.16 |
| 0.1 mg/L | 4.08 ± 0.09 | 4.03 ± 0.62 | 3.88 ± 0.15 | 123 ± 2.45 | 124 ± 1.17 | 124 ± 2.25 |
| 1 mg/L | 3.92 ± 0.10 | 4.01 ± 0.26 | 3.97 ± 0.08 | 123 ± 3.03 | 124 ± 1.08 | 124 ± 1.67 |
| 10 mg/L | 3.78 ± 0.05 | 3.82 ± 0.44 | — | 117 ± 3.90 | 117 ± 2.24 | — |
| 100 mg/L | — | — | — | — | — | — |

It was found by further observation of the whole process of zebrafish embryo development that at 100 mg/L, 48 h, in the groups of Compound 2 and Compound 9, no zebrafish embryos died, but phenomena such as pericardial cyst, no heartbeat, no bloodstream, no tail development and the like occurred in embryos; in the ibuprofen group at the same dose, all the zebrafish embryos died. At 10 mg/L, 48 h, in the groups of Compound 2 and 9, the development of zebrafish embryos was basically normal; while in the ibuprofen group, phenomena such as pericardial cyst, no heartbeat, no bloodstream, and no tail development occurred in zebrafish. In the ibuprofen group at 1 mg/L, 72 h, embryos development delayed, with a hatching rate of only 56.7%, and mild edema occurred in pericardial sac of some zebrafishes, while Compound 2 and 9 at the same dose had no impact.

Experimental Example 7: Assay on Effects of Compounds 2, 9, 34 and COX2 Selective Inhibitor Celecoxib on hERG Potassium Channel CHO-hERG cells (purchased from ATCC) were incubated in a culture flask. When the cell density reached 60~80%, the culture medium (Glutamax DMEM/F12 medium (Gibco, Shanghai) containing 10% fetal bovine serum) was removed. The cells were washed with 7 mL PBS once, and then digested by adding 3 mL Detachin cell dissociation buffer. After complete digestion, the resultant mixture was neutralized by adding 7 mL culture medium, and centrifuged. The supernatant was removed with a pipette, 5 mL culture medium was added to re-suspend the cells to ensure a cell density of 2~5×10$^6$/mL.

Intracellular fluid and extracellular fluid were prepared as described in the following table.

| Reagent | Extracellular fluid (mM) | Intracellular fluid (mM) |
|---|---|---|
| CaCl$_2$ | 2 | 5.374 |
| MgCl$_2$ | 1 | 1.75 |
| KCl | 4 | 120 |
| NaCl | 145 | — |
| Glucose | 10 | — |
| HEPES | 10 | 10 |
| EGTA | — | 5 |
| Na-ATP | — | 4 |
| pH | 7.40 | 7.25 |

A certain amount of compound was dissolved in extracellular fluid at the following concentrations, to prepare the stock solution of compound. 2 µL stock solution of compound was added to 998 µL extracellular fluid, and was subjected to 5-fold serial dilution in extracellular fluid containing 0.2% DMSO to get the final concentrates to be tested. The highest test concentration for a test compound was 40 µM, followed by six concentrations, i.e., 40M, 8 µM, 1.6 µM, 0.32 µM, 0.064 µM, and 0.0128 M. The highest test concentration of the positive compound, cisapride was 3 µM, followed by six concentrations, i.e., 3 µM, 0.6 µM, 0.12 µM, 0.024 µM, 0.0048 µM, and 0.00096 µM. In the final test concentration, the amount of DMSO was not more than 0.2%, as DMSO at the concentration had no effect on hERG potassium channel.

Single cell giga-seal and formation of whole-cell mode were automatically performed by Sophion Qpatch HT fully automated cell patch clamp systems. After obtaining the whole-cell recording mode, the cell was clamped at −80 mV. The cell first underwent pre-voltage of −50 mV for 50 msec, then underwent depolarization stimulation at 20 mV for 5 sec, and then underwent repolarization at −50 mV for 5 sec, and then the voltage return to −80 mv. The cell underwent the stimulation at the voltage every 15 sec, and the data were recorded for 2 min, then extracellular fluid was administered, and then the data were recorded for 2 min. Then, the administration process begun. The concentration of a test compound started from the lowest concentration, each test concentration was administered for 2 min. After continuous administration of the test compound at all the concentrations, the positive control compound Cisapride was administered. At least three cells were tested for each concentration (n≥3). The experimental data was analyzed by XLFit software.

The experimental results showed that the median inhibitory concentration of Cisapride is 0.1 μM to hERG potassium channel, and the median inhibitory concentration of celecoxib is 6.4 μM to hERG potassium channel, while Compound 2, 9 and 34, at the highest concentration of 40 μM for evaluation, had maximal inhibition rate of 38.30%, 31.42%, 44.67% (See Table 6) for hERG potassium channel, respectively. These results showed that Compound 2, 9 and 34 had low inhibition rate for hERG potassium channel at high concentration, and had better cardiac safety than the commercially available analgesics $COX_2$ selective inhibitor celecoxib.

TABLE 6

Inhibitory effects of Compounds 2, 9, 34 and celecoxib, Cisapride on hERG potassium channel.

| Compound | Maximum concentration-inhibition rate (%) | median inhibitory concentration (μM) |
| --- | --- | --- |
| 2 | 38.30 | >40 |
| 9 | 31.42 | >40 |
| 34 | 44.67 | >40 |
| celecoxib | 74.81 | 6.4 |
| Cisapride | 98.46 | 0.10 |

Although the embodiments of the invention are described in detail, a person skilled in the art would understand that according to all the already disclosed teachings, these details can be modified and replaced, and these alterations all fall in the protection scope of the invention. The scope of the invention is defined by the claims and any equivalent thereof.

The invention claimed is:

1. A compound, or a pharmaceutically acceptable salt, a hydrate or a solvate thereof, wherein the compound is selected from the group consisting of:

Compound 1

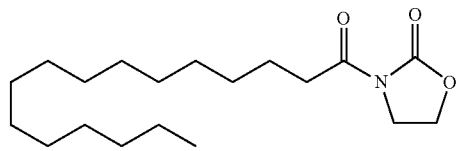

Compound 2

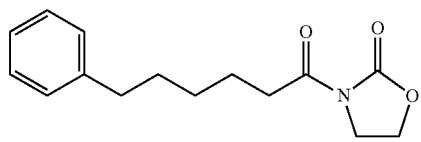

Compound 3

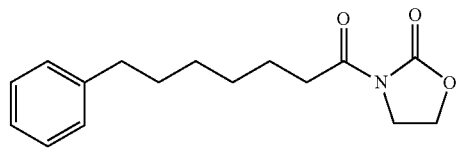

Compound 4

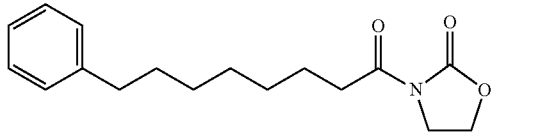

Compound 5

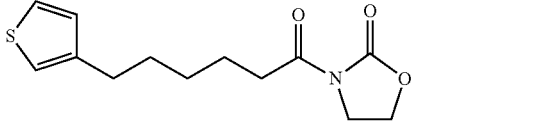

Compound 6

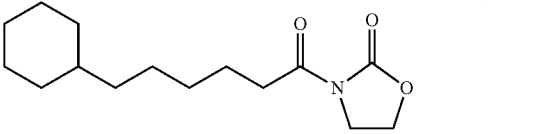

Compound 7

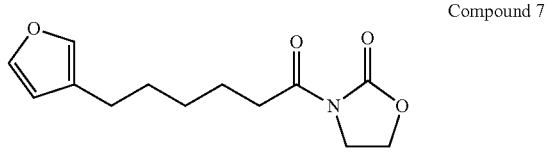

Compound 8

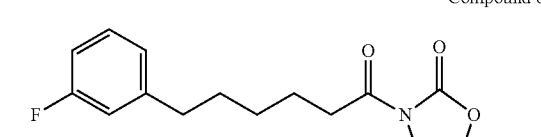

Compound 9

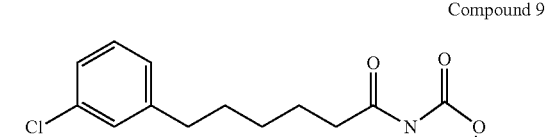

Compound 10

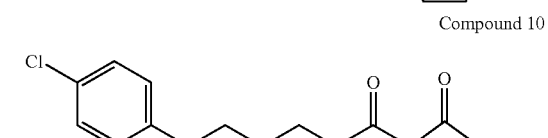

Compound 11

Compound 12

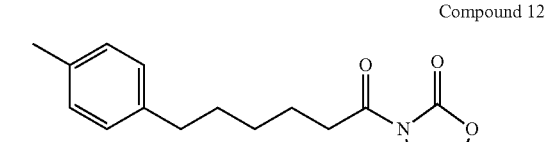

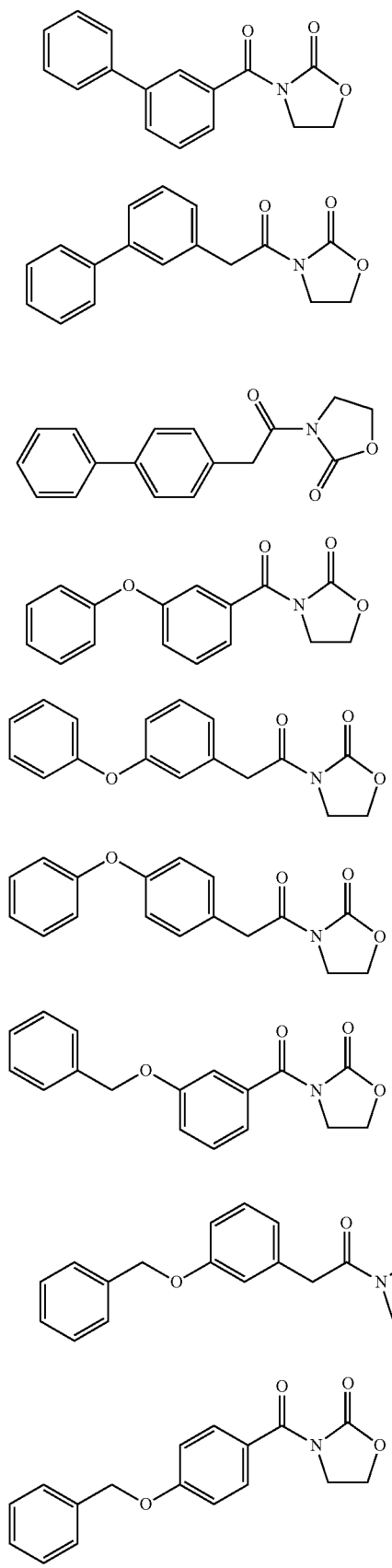

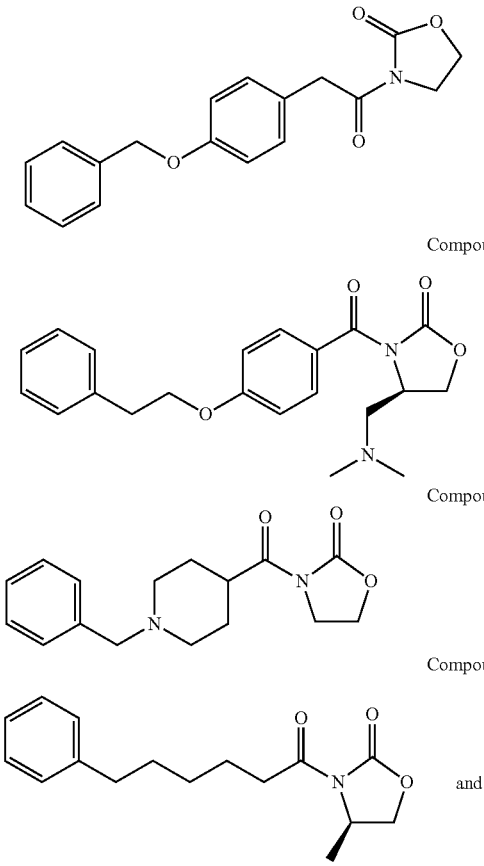

2. A pharmaceutical composition, comprising at least the compound, or a pharmaceutically acceptable salt, a hydrate or a solvate thereof according to claim 1, and a pharmaceutically acceptable adjuvant.

3. A method for treating a pain, or alleviating severity of said pain, comprising administering to a patient in need of the treatment a therapeutically effective amount of at least one compound, or a pharmaceutically acceptable salt, a hydrate or a solvate thereof according to claim 1.

4. The method according to claim 3, wherein said pain is selected from the group consisting of: neuropathic pain, inflammatory pain, and mixed pain.

5. The method according to claim 4, wherein said neuropathic pain is selected from the group consisting of central neuropathic pain, and peripheral neuropathic pain, and/or
wherein said inflammatory pain is selected from the group consisting of: osteoarthritis pain, fibromyalgia syndrome, inflammatory pain of rheumatic and rheumatoid arthritis, inflammatory pain of endometriosis, inflammatory toothache, ankylosing spondylitis pain, gouty arthritis pain, and visceral inflammatory pain, and/or
wherein said mixed pain is selected from the group consisting of lumbodynia, shoulder pain, burning mouth syndrome, complex regional pain syndrome, migraine, cluster headache, and tension headache syndrome, and prosopodynia.

6. The method according to claim 5, wherein said peripheral neuropathic pain is selected from the group consisting of: postherpetic neuralgia, pain caused by diabetic perineuropathy, neurothlipsis and exudation caused by tumor, lumbar surgery failure syndrome, neuropathic pain caused by lumbar disc protrusion, postpartum neuralgia, trigeminal neuralgia, chemotherapy-induced multiple neuropathic pain, post-radiotherapy plexopathy, and radicular neuralgia.

7. The method according to claim 5, wherein said central neuropathic pain is selected from the group consisting of: compression pain caused by spinal sclerosis, multiple sclerosis related pain, Parkinsonism related pain, dementia related pain, post-stroke pain, and pain following spinal cord injury.

8. The method according to claim 5, wherein said visceral inflammatory pain is selected from the group consisting of: appendicitis, gastritis, pancreatitis, prostatitis, myocarditis, interstitial cystitis, pain caused by hepatic, gall or kidney stone, irritable bowel syndrome, and chronic pelvic pain syndrome.

* * * * *